(12) United States Patent
Kawakami et al.

(10) Patent No.: US 7,838,128 B2
(45) Date of Patent: Nov. 23, 2010

(54) CARBAZOLE DERIVATIVE, AND LIGHT EMITTING ELEMENT MATERIAL, LIGHT EMITTING ELEMENT, AND ELECTRONIC APPLIANCE OBTAINED USING THE SAME

(75) Inventors: Sachiko Kawakami, Kanagawa (JP); Nobuharu Ohsawa, Kanagawa (JP); Harue Nakashima, Kanagawa (JP); Kumi Kojima, Tokyo (JP); Masakazu Egawa, Kanagawa (JP); Ryoji Nomura, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 82 days.

(21) Appl. No.: 11/574,117
(22) PCT Filed: Jul. 10, 2006
(86) PCT No.: PCT/JP2006/314116
§ 371 (c)(1),
(2), (4) Date: Feb. 22, 2007
(87) PCT Pub. No.: WO2007/007885
PCT Pub. Date: Jan. 18, 2007

(65) Prior Publication Data
US 2009/0058261 A1    Mar. 5, 2009

(30) Foreign Application Priority Data
Jul. 14, 2005    (JP) .............................. 2005-205386

(51) Int. Cl.
*H01J 1/02* (2006.01)
(52) U.S. Cl. .................. 428/690; 313/503; 544/141
(58) Field of Classification Search ................ None
See application file for complete search history.

(56) References Cited
U.S. PATENT DOCUMENTS
5,811,834 A    9/1998    Tamano et al.
(Continued)

FOREIGN PATENT DOCUMENTS
JP    09157643    6/1997
(Continued)

OTHER PUBLICATIONS
Kawakami, WO2007/013537, Feb. 2007, pp. 1-137.*
(Continued)

*Primary Examiner*—D. Lawrence Tarazano
*Assistant Examiner*—Gregory Clark
(74) *Attorney, Agent, or Firm*—Fish & Richardson P.C.

(57) ABSTRACT

An object is to provide a carbazole derivative that is useful as a raw material in manufacturing a light emitting element material having resistance to repetition of an oxidation reaction. The carbazole derivative is represented by General Formula (1) in the following. In General Formula (1), $R^1$ represents any one selected from an alkyl group having 1 to 4 carbon atoms such as methyl, ethyl, and tert-butyl, and an aryl group having 1 to 12 carbon atoms such as phenyl, biphenyl, and naphthyl.

(1)

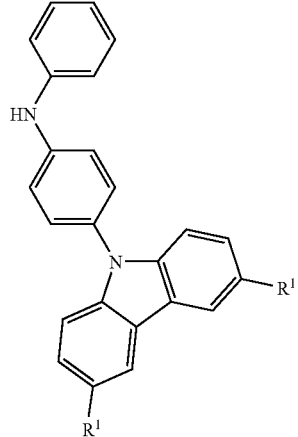

12 Claims, 49 Drawing Sheets

U.S. PATENT DOCUMENTS

| | | |
|---|---|---|
| 6,743,948 B1 | 6/2004 | Hosokawa et al. |
| 6,951,693 B2 | 10/2005 | Hosokawa et al. |
| 2004/0161633 A1* | 8/2004 | Seo et al. .................. 428/690 |
| 2005/0038296 A1 | 2/2005 | Hosokawa et al. |
| 2005/0225235 A1 | 10/2005 | Kim et al. |
| 2006/0068221 A1 | 3/2006 | Saitoh et al. |
| 2006/0189828 A1 | 8/2006 | Hosokawa et al. |
| 2008/0114178 A1 | 5/2008 | Kawakami et al. |
| 2009/0102360 A1 | 4/2009 | Kawakami et al. |

FOREIGN PATENT DOCUMENTS

| | | | |
|---|---|---|---|
| JP | 09-249876 | * | 9/1997 |
| JP | 2001-131541 | | 5/2001 |
| JP | 2003031371 | | 1/2003 |
| JP | 2004-103467 | | 4/2004 |
| JP | 2004-178896 | | 6/2004 |
| WO | WO 03/050201 A1 | | 6/2003 |
| WO | WO 2005/090512 A1 | | 9/2005 |
| WO | WO 2006/070897 A1 | | 7/2006 |

OTHER PUBLICATIONS

English Translation of JP 09-249876.*

Catalog: Chemicals for Xerography and OLED Fine Chemicals Custom Synthesis; p. 77; 2003.

Andrew Kung et al.; "Diphenylnitrenium Ion: Cyclization, Electron Transfer, and Polymerization Reactions"; *Journal of Organic Chemistry*, vol. 70, No. 13; pp. 5283-5290; Mar. 24, 2005.

PCT Written Opinion (Application No. PCT/JP2006/314116) dated Oct. 3, 2006.

PCT International Search Report (Application No. PCT/JP2006/314116) dated Oct. 3, 2006.

European Search Report & Written Opinion for Application No. 06781141.4; PCT/JP2006314116; dated Jun. 29, 2009; 7 pages.

* cited by examiner

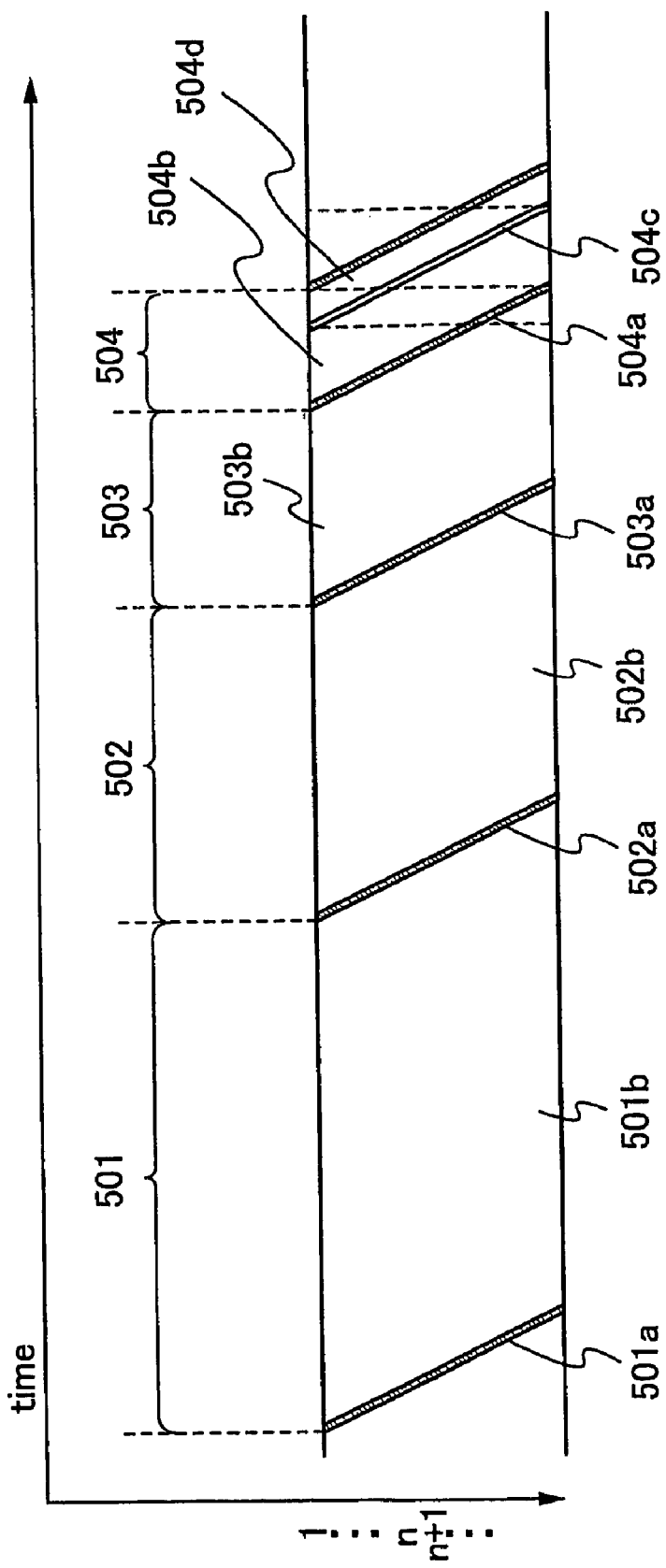

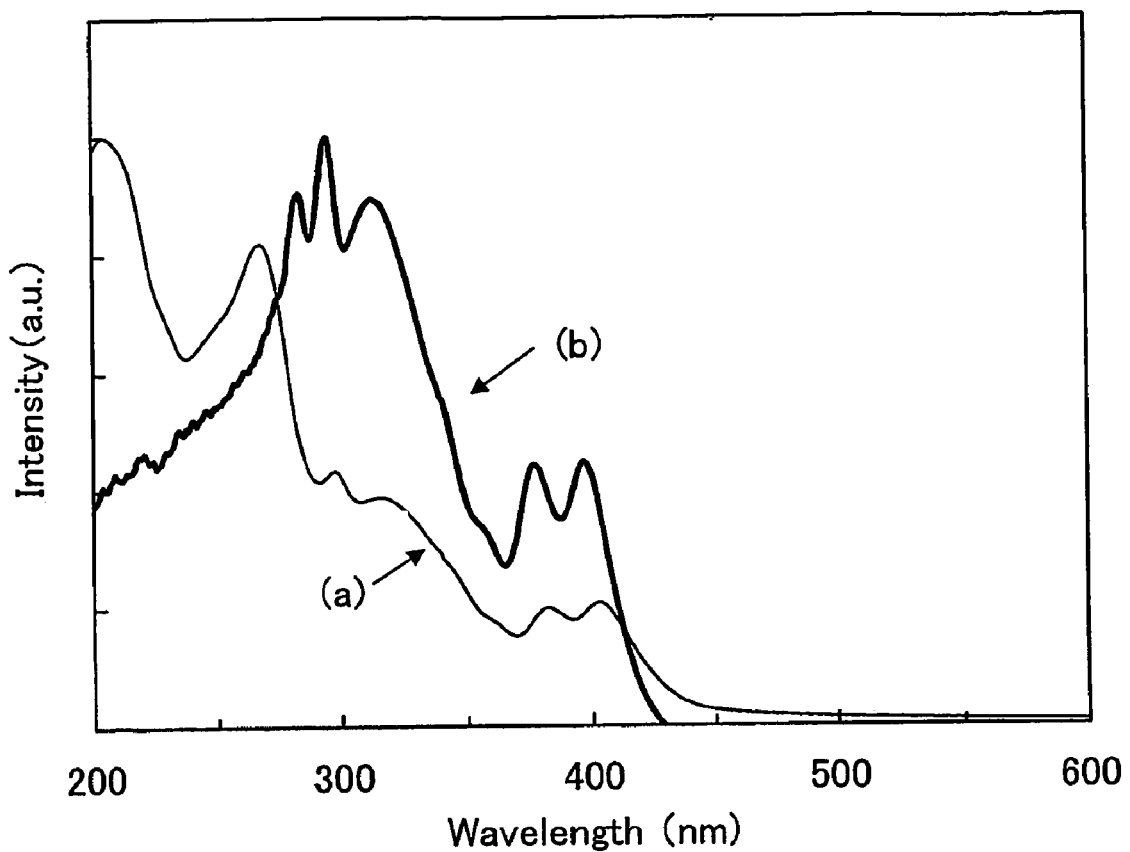

CARBAZOLE DERIVATIVE, AND LIGHT EMITTING ELEMENT MATERIAL, LIGHT EMITTING ELEMENT, AND ELECTRONIC APPLIANCE OBTAINED USING THE SAME

TECHNICAL FIELD

The present invention relates to a carbazole derivative, and particularly relates to a carbazole derivative that can be used as a raw material in obtaining a light emitting element material. Further, the present invention relates to a light emitting material obtained using the carbazole derivative, as well as a light emitting element and an electronic appliance manufactured using the light emitting element material.

BACKGROUND ART

In recent years, light emitting elements are beginning to be used as pixels for displays and the like. Such light emitting elements generally have a structure in which a layer containing a light emitting substance is interposed between a pair of electrodes.

In the field of light emitting elements, in order to obtain a light emitting element with favorable light emission efficiency and chromaticity, or for which quenching of light can be prevented, various researches are carried out for a substance for a material for manufacturing a light emitting element. Among them, a substance used as a light emitting substance (a substance exhibiting light emission when a light emitting element is driven) is generally termed a "guest," and development of a guest which emits light with better efficiency is being advanced. For example, Patent Document 1: Japanese Patent Laid-Open No. 2001-131541 discloses a technique relating to an organic EL element material with a long light emission life span with high light emission efficiency.

DISCLOSURE OF INVENTION

In regards to a light emitting element, current flows by a transfer of holes or electrons, and in a light emitting layer, these carriers are trapped by a guest and recombine. In other words, the guest comes to an excited state after a state of being oxidized or reduced. Subsequently, the guest that has come to an excited state emits light when returning to a ground state. The guest that has returned to a ground state, after coming to an excited state again by a recombination of carriers, emits light when returning to a ground state. A guest for which such excitation and light emission are repeated, in other words, a guest for which oxidation or reduction is repeated, may come to have a different property as it goes through oxidation or reduction. When a property of the guest changes while repeating excitation and light emission, desired light emission may not be able to be obtained, or it could become a cause of element deterioration due to a change in transporting property of the carrier. Therefore, a guest is not only demanded to emit light efficiency, but also to have resistance to oxidation or reduction.

In order for a light emitting element to emit light efficiently, it is demanded that recombination efficiency of carriers is improved by making a guest to efficiently trap carriers. In many light emitting elements, a light emitting layer has a structure in which a guest is dispersed in a substrate termed "host," and by combining the host and the guest so that a HOMO level of the guest is higher than a HOMO level of the host, or so that a LUMO level of the guest is lower than a LUMO level of the host, carries are easier to trap. However, while carriers are easier to trap, an energy gap between the HOMO level and the LUMO level becomes small, and there is a case of not being able to obtain a light emitting element exhibiting light emission with a desired chromaticity. Such, a problem is especially apparent in a light emitting element exhibiting blue light emission.

Consequently, an object of the present invention is to provide a carbazole derivative that is useful as a raw material in manufacturing a light emitting element material having resistance to repetition of an oxidation reaction.

Also, an object of the present invention is to provide a light emitting material having resistance to repetition of an oxidation reaction.

An object of the present invention is to provide a light emitting element having resistance to repetition of an oxidation reaction, and by which favorable light emission can be obtained for a long period of time. Note that "repetition of an oxidation reaction" in this specification means repeating an oxidation process of electrically oxidizing a neutral substance and then returning it to a neutral state.

Further, an object of the present invention is to provide a light emitting element, a light emitting device, and an electronic appliance which exhibit blue light emission with favorable chromaticity.

One feature of the present invention is a carbazole derivative represented by the following General Formula (1).

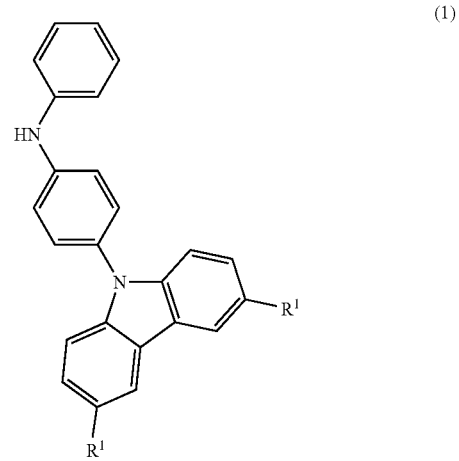

(1)

In General Formula (1), $R^1$ represents any one selected from hydrogen, an alkyl group having 1 to 4 carbon atoms such as methyl, ethyl, and tert-butyl, and an aryl group having 1 to 12 carbon atoms such as phenyl, biphenyl, and naphthyl.

One feature of the present invention is a light emitting element material represented by General Formula (2) of the following.

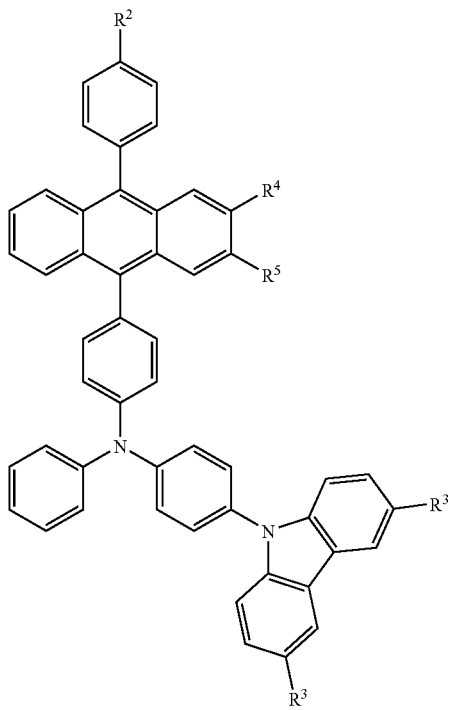

(2)

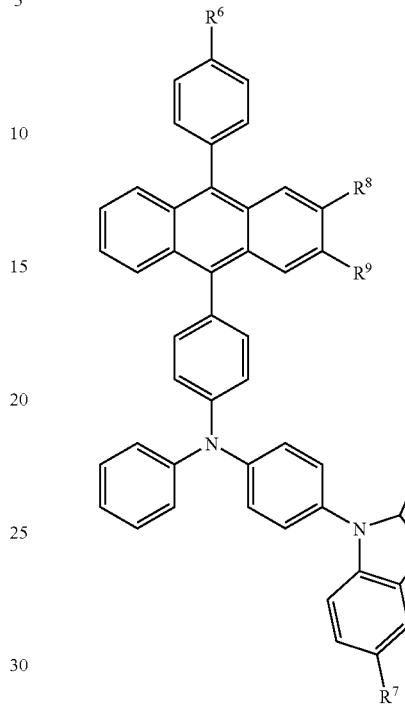

(4)

preferably a substance with a higher electron transporting property than a hole transporting property.

In General Formula (2), $R^2$ represents hydrogen or a group represented by the following General Formula (3). Also, $R^4$ and $R^5$ represent any of hydrogen, methyl, or tert-butyl, and at least one of them represents hydrogen. Further, in General Formulas (2) and (3), $R^3$ represents any one selected from hydrogen, an alkyl group having 1 to 4 carbon atoms such as methyl, ethyl, and tert-butyl, and an aryl group having 1 to 12 carbon atoms such as phenyl, biphenyl, and naphthyl.

In General Formula (4), $R^6$ represents hydrogen or a group represented by the following General Formula (5). Also, $R^8$ and $R^9$ represent any of hydrogen, methyl, or tert-butyl, and at least one of them represents hydrogen. Further, in General Formulas (4) and (5), $R^7$ represents any one selected from hydrogen, an alkyl group having 1 to 4 carbon atoms such as methyl, ethyl, or tert-butyl, or an aryl group having 1 to 12 carbon atoms such as phenyl, biphenyl, or naphthyl.

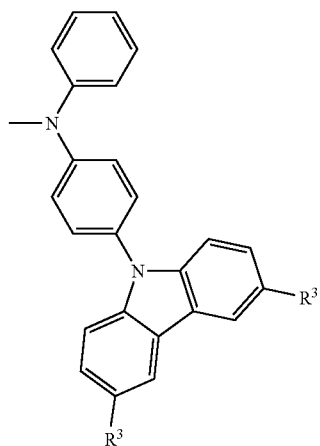

(3)

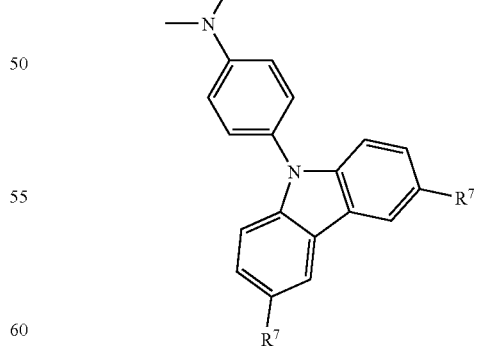

(5)

One feature of the present invention is a light emitting element that has a light emitting layer between electrodes, and the light emitting layer contains a light emitting substance represented by the following General Formula (4) and a host having a higher ionization potential and a larger energy gap than those of the light emitting substance. The host is One feature of the present invention is a light emitting element that has a light emitting layer between electrodes, and the light emitting layer contains a light emitting substance represented by the foregoing General Formula (4) and a host having a higher ionization potential and a larger energy gap than those of the light emitting substance. The host is preferably a substance with a higher electron transporting property than a hole transporting property.

One feature of the present invention is an electronic appliance using a light emitting device of the present invention in a display portion or in a lighting portion.

By implementing the present invention, a carbazole derivative that is useful in manufacturing a light emitting element material having excellent resistance with respect to repetition of an oxidation reaction can be obtained. Also, by implementing the present invention, a light emitting element material having excellent resistance with respect to repetition of an oxidation reaction can be obtained. Further, by implementing the present invention, a light emitting device having resistance to repetition of an oxidation reaction that is capable of light emission for a long period of time in a favorable state can be obtained. Furthermore, by implementing the present invention, an electronic appliance capable of favorable display operation or lighting, for a long period of time, can be obtained.

By implementing the present invention, a carbazole derivative that is useful in manufacturing a light emitting element material used as a light emitting substance capable of exhibiting blue light emission with favorable chromaticity can be obtained. Also, by implementing the present invention, a light emitting element material capable of exhibiting blue light emission with favorable chromaticity can be obtained. By implementing the present invention, a light emitting device that exhibits blue light emission with good chromaticity that displays an image having excellent colors can be obtained. Further, by implementing the present invention, an electronic appliance that exhibits blue light emission with good chromaticity that displays an image having excellent colors can be obtained.

BRIEF DESCRIPTION OF DRAWINGS

In the accompanying drawings:

FIG. 5 is a view describing a mode of frame operation of a light emitting device of the present invention;

FIG. 16 is an absorption spectrum of a light emitting element material manufactured in Embodiment 3;

BEST MODE FOR CARRYING OUT THE INVENTION

Embodiment Modes

Figure 1:
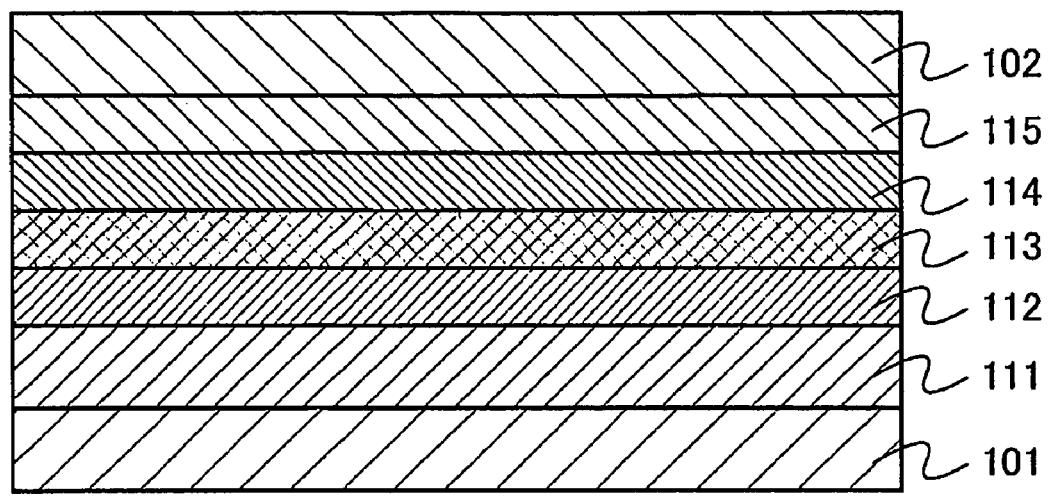
FIG. 1 is a view describing a mode of a light emitting element of the present invention.

The embodiment modes according to the present invention will hereinafter be described. It is easily understood by those skilled in the art that the embodiment modes and details herein disclosed can be modified in various ways without departing from the purpose and the scope of the present invention. The present invention should not be interpreted as being limited to the description of the embodiment modes to be given below.

Embodiment Mode 1

One mode of a carbazole derivative of the present invention and a manufacturing method thereof will be described.

As specific modes of a carbazole derivative of the present invention, carbazole derivatives represented by the following Structural Formulas (1) to (9) can be given.

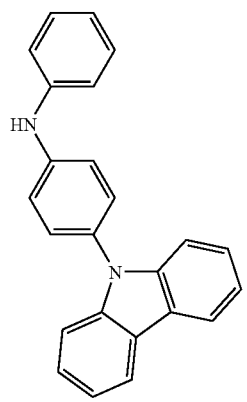

(1)

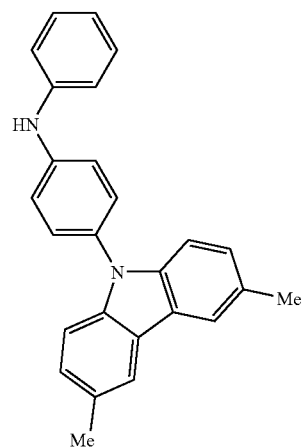

(2)

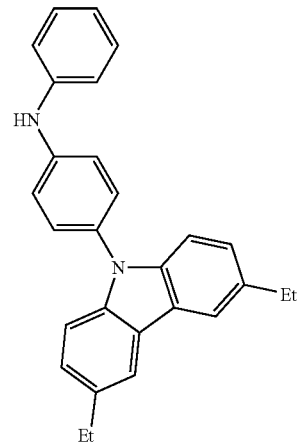

(3)

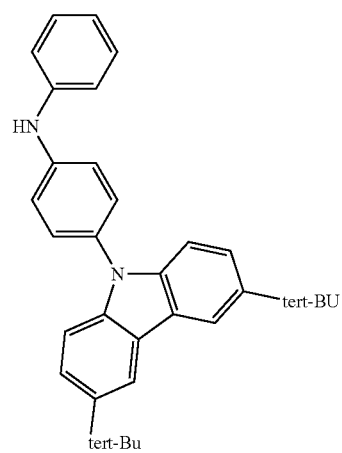

(4)

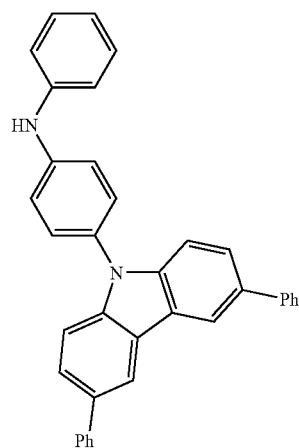

(5)

-continued

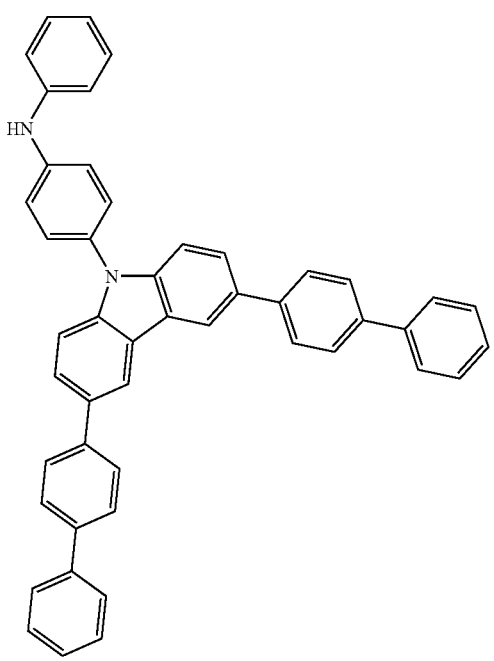
(6)

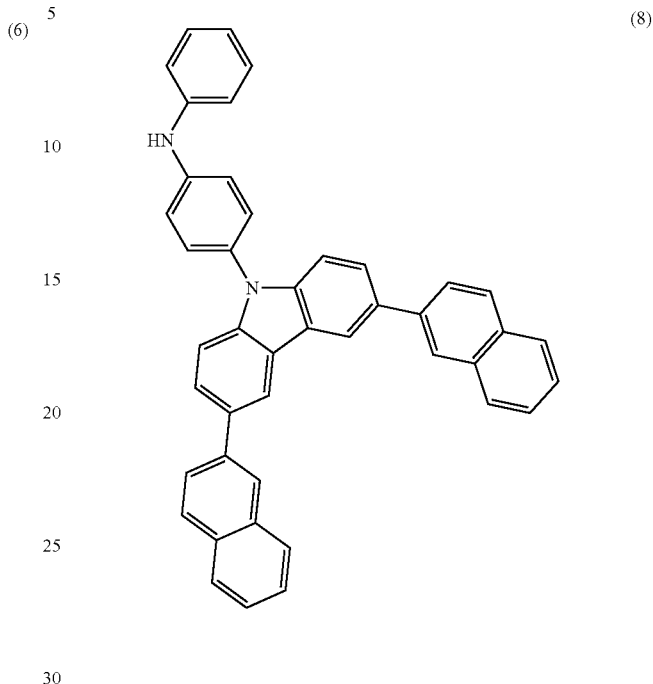
(8)

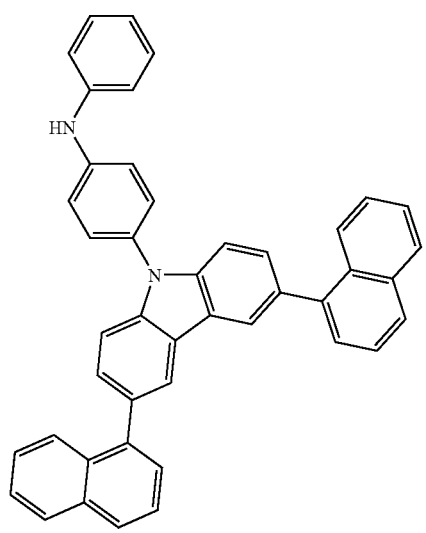
(7)

(9)

A carbazole derivative of the present invention represented by the following General Formula (6), more specifically, represented by Structural Formulas (1) to (9), is obtained as represented by Synthesis Scheme (a-1) by reacting a compound (compound A) containing carbazole in its skeleton with 1,4-dibromobenzene to synthesize a compound B containing N-(4-bromophenyl) carbazole in its skeleton, and then carrying out a coupling reaction with aniline that uses a palladium catalyst.

(6)

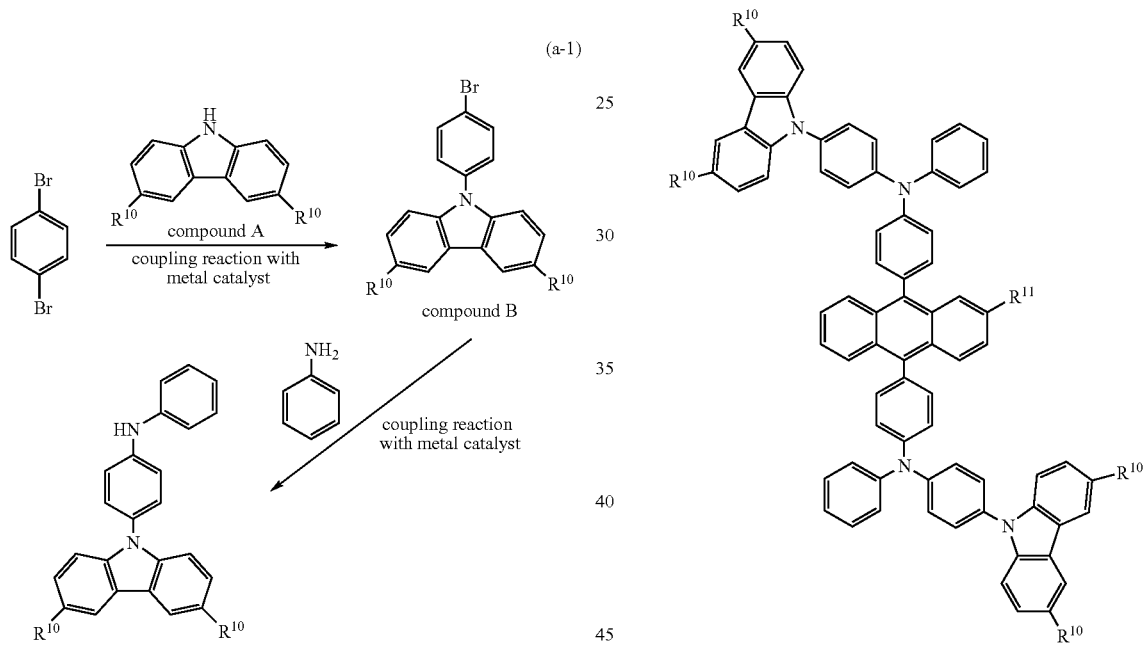

(a-1)

is also useful as a raw material in manufacturing a light emitting substance exhibiting blue light emission with good chromaticity.

Embodiment Mode 2

One mode of a manufacturing method of an anthracene derivative using a carbazole derivative of the present invention will be described.

As represented by the following Synthesis Scheme (b-1), by causing a coupling reaction between the carbazole derivative represented by General Formula (6) and a compound C having a diphenyl anthracene skeleton, using a metal catalyst such as a palladium catalyst, an anthracene derivative represented by the following General Formula (7) that is useful as a light emitting element material can be obtained.

(7)

In General Formula (6) and Synthesis Scheme (a-1), $R^{10}$ represents any one selected from hydrogen, an alkyl group having 1 to 4 carbon atoms such as methyl, ethyl, and tert-butyl, and an aryl group having 1 to 12 carbon atoms such as phenyl, biphenyl, and naphthyl. Note that the aryl group may or may not have a substituent group.

A synthesis method of a carbazole derivative of the present invention is not limited to the synthesis method represented by Synthesis Scheme (a-1), and a carbazole derivative of the present invention may be synthesized by another synthesis method.

The carbazole derivative of the present invention described above is extremely useful as a raw material in manufacturing a light emitting element material having excellent resistance with respect to repetition of an oxidation reaction. Also, the carbazole derivative of the present invention described above (b-1)

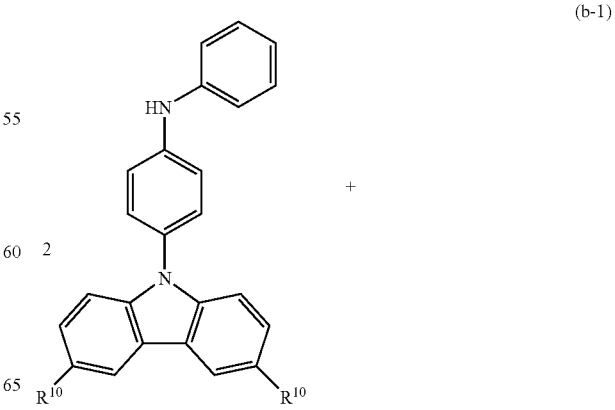

-continued

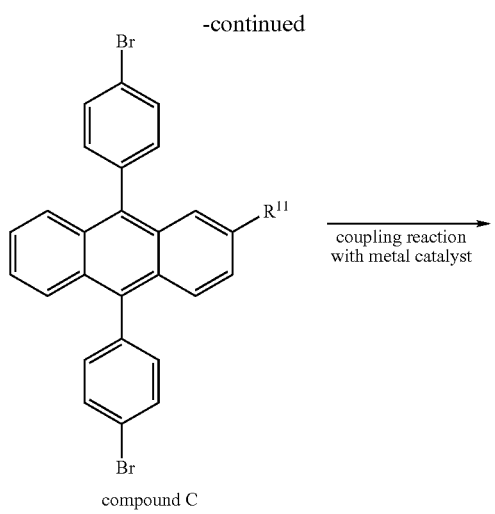

compound C

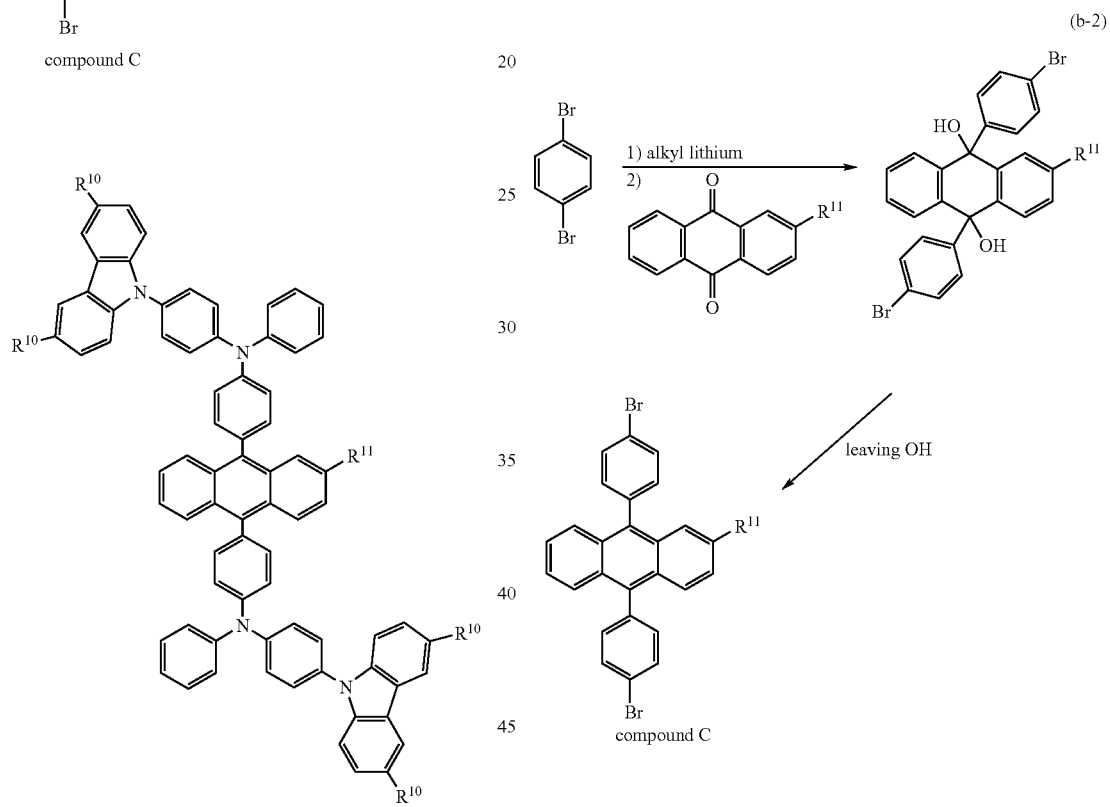

In General Formula (7) and Synthesis Scheme (b-1), $R^{10}$ represents any one selected from hydrogen, an alkyl group having 1 to 4 carbon atoms such as methyl, ethyl, and tert-butyl, and an aryl group having 1 to 12 carbon atoms such as phenyl, biphenyl, and naphthyl. $R^{11}$ represents any of hydrogen, methyl, or tert-butyl.

An anthracene derivative obtained in the above manner has resistance to repetition of an oxidation reaction, and can exhibit blue light emission. For this reason, it is particularly useful as a light emitting element material serving as a light emitting substance (also termed "guest"). Further, the anthracene derivative represented by General Formula (7) is extremely suitable to be used in combination with an organic compound that is effective as a host to a light emitting substance with an excellent electron transporting property and a wide energy gap that exhibits blue light emission, such as 2-tert-butyl-9,10-di(2-naphthyl)anthracene (abbreviation: t-BuDNA), 9-[4-(N-carbazolyl)]phenyl-10-phenylanthracene (abbreviation: CzPA), or diphenyl anthracene. By using the anthracene derivative represented by General Formula (7) in combination with t-BuDNA, CzPA, diphenyl anthracene, or the like, an appropriate amount of holes can be trapped and penetration of holes from a light emitting layer to another layer can be reduced, as well as a light emitting element that can exhibit blue light emission with good chromaticity can be manufactured.

Note that the compound C used in Synthesis Scheme (b-1) is obtained for example by a synthesis like the one represented by the following Synthesis Scheme (b-2).

In Synthesis Scheme (b-2), $R^{11}$ represents hydrogen or tert-butyl.

Embodiment Mode 3

One mode of a synthesis of an anthracene derivative using a carbazole derivative of the present invention will be described.

As represented by the following Synthesis Scheme (c-1), by causing a coupling reaction between a carbazole derivative represented by General Formula (6) and a compound D having a diphenyl anthracene skeleton, using a metal catalyst such as a palladium catalyst, an anthracene derivative represented by the following General Formula (8) that is useful as a light emitting element material can be obtained.

(8)

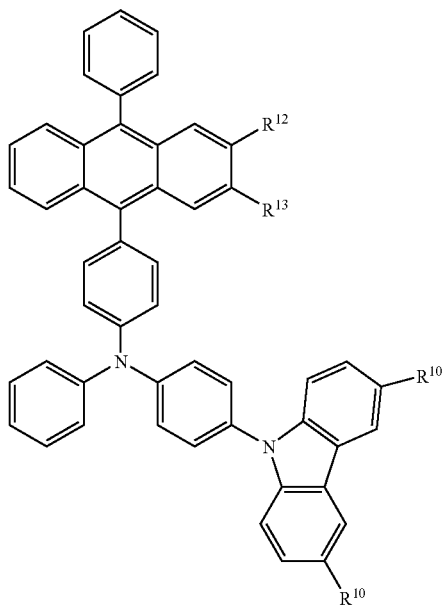

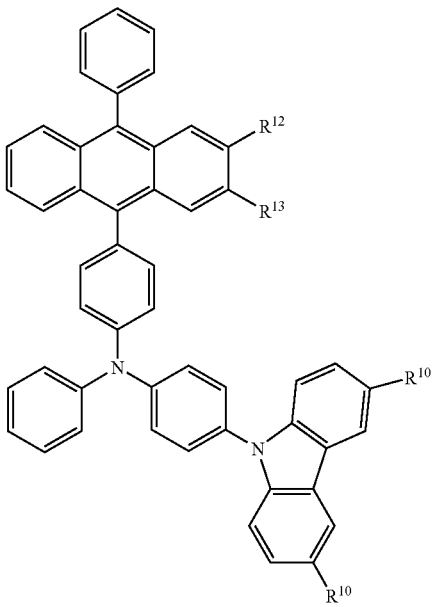
-continued (c-1)

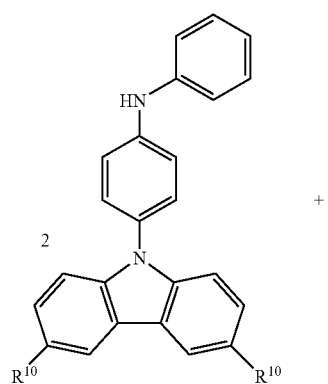

+

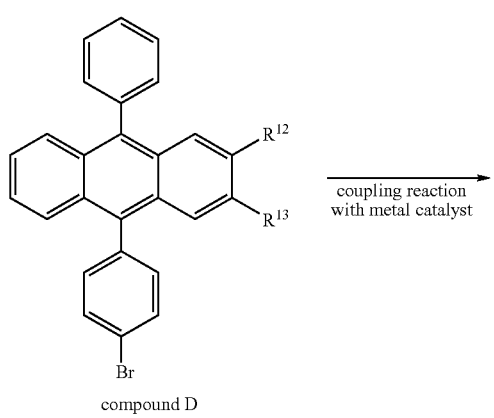

coupling reaction with metal catalyst
→

In General Formula (8) and Synthesis Scheme (c-1), $R^{10}$ represents any one selected from hydrogen, an alkyl group having 1 to 4 carbon atoms such as methyl, ethyl, and tert-butyl, and an aryl group having 1 to 12 carbon atoms such as phenyl, biphenyl, and naphthyl. $R^{12}$ and $R^{13}$ represent any of hydrogen, methyl, or tert-butyl, and at least one of them represents hydrogen.

An anthracene derivative obtained in the above manner has resistance to repetition of an oxidation reaction, and can exhibit blue light emission. For this reason, it is particularly useful as a light emitting element material serving as a light emitting substance. Further, the anthracene derivative represented by General Formula (8) is extremely suitable to be used in combination with an organic compound that is effective as a host to a light emitting substance with an excellent electron transporting property and a wide energy gap that exhibits blue light emission, such as t-BuDNA, or CzPA. By using the anthracene derivative represented by General Formula (8) in combination with t-BuDNA, CzPA, diphenyl anthracene, or the like, an appropriate amount of holes can be trapped and penetration of holes from a light emitting layer to another layer can be reduced, as well as a light emitting element that can exhibit blue light emission with good chromaticity can be manufactured.

Note that the compound D used in Synthesis Scheme (c-1) is obtained for example by a synthesis like the one represented by the following Synthesis Scheme (c-2).

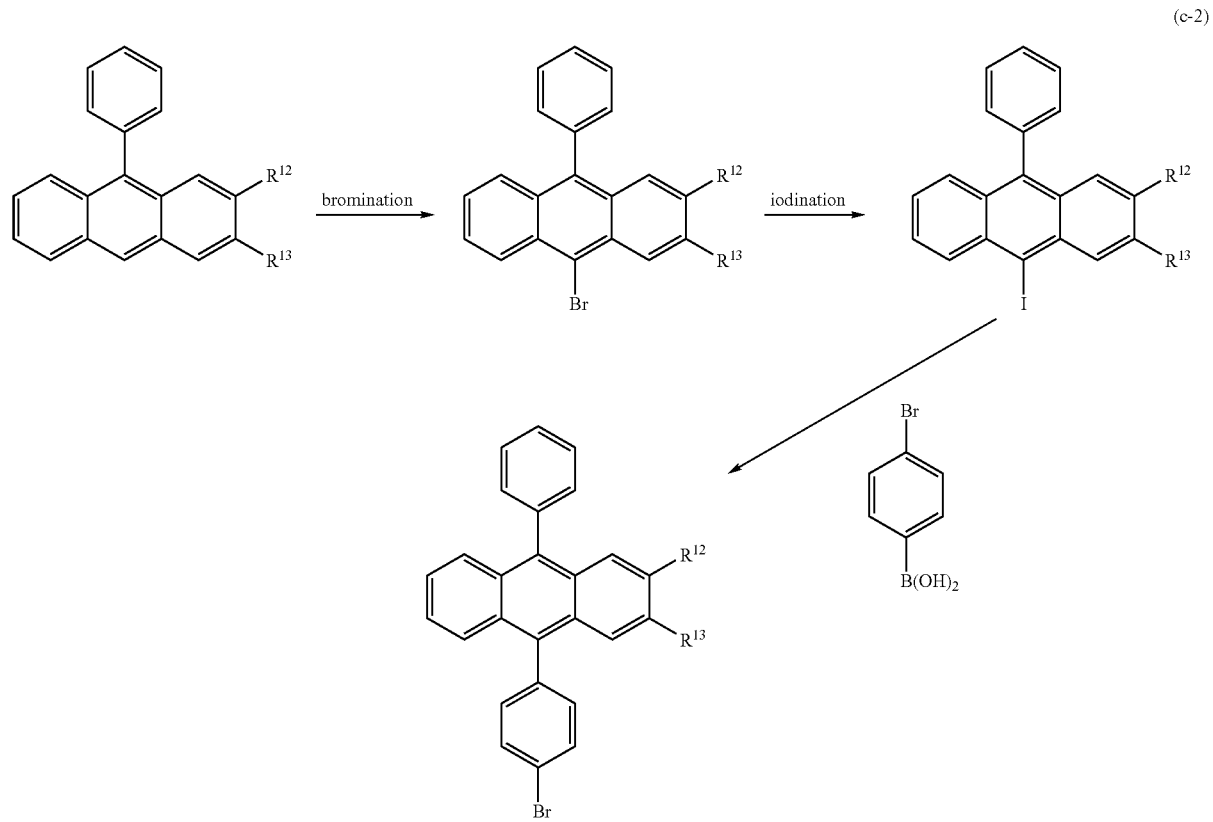

(c-2)

In Synthesis Scheme (c-2), $R^{12}$ and $R^{13}$ represent any of hydrogen, methyl, or tert-butyl, and at least one of them represents hydrogen.

In Embodiment Modes 2 and 3, modes of manufacturing a light emitting element material by a coupling reaction between a carbazole derivative of the present invention and an anthracene derivative is described; however, a light emitting element material may be manufactured by a coupling reaction not only between an anthracene derivative and a carbazole derivative of the present invention, but also between a perylene derivative or a phenanthrene derivative and the carbazole derivative of the present invention.

Embodiment Mode 4

One mode of a light emitting element manufactured by using a light emitting element material synthesized by using a carbazole derivative of the present invention will be described with reference to FIG. 1.

FIG. 1 represents a light emitting element that has a light emitting layer 113 between a first electrode 101 and a second electrode 102. In the light emitting layer 113, an anthracene derivative represented by General Formula (7) or (8) is contained. Also, in the light emitting element of FIG. 1, a hole injecting layer 111 and a hole transporting layer 112 are laminated and provided in this order between the first electrode 101 and the light emitting layer 113, and an electron injecting layer 115 and an electron transporting layer 114 are laminated and provided in this order between the second electrode 102 and the light emitting layer 113.

In such a light emitting element, holes injected from a first electrode 101 side and electrons injected from a second electrode 102 side recombine in the light emitting layer 113, and the anthracene derivative represented by General Formula (7) or (8) comes to an excited state. Then, the anthracene derivative in an excited state emits light when returning to a ground state. In this manner, the anthracene derivative represented by General Formula (7) or (8) serves as a light emitting substance.

In the following, the first electrode 101, the second electrode 102, and each layer provided between the first electrode 101 and the second electrode 102 are described specifically.

The first electrode 101 and the second electrode 102 are not particularly limited. They can be formed by using gold (Au), platinum (Pt), nickel (Ni), tungsten (W), chromium (Cr), molybdenum (Mo), iron (Fe), cobalt (Co), copper (Cu), palladium (Pd) or the like, in addition to indium tin oxide (ITO), indium tin oxide containing silicon oxide, or indium oxide containing 2 to 20% by weight of zinc oxide. The first electrode 101 can also be formed using an alloy of magnesium and silver, an alloy of aluminum and lithium, or the like, in addition to aluminum. Further, a formation method of the first electrode 101 and the second electrode 102 is not particularly limited. For example, the first electrode 101 and the second electrode 102 can be formed by using a sputtering method, an evaporation method, or the like. To extract light to the outside, one or both of the first electrode 101 and the second electrode 102 is/are preferably formed by using indium tin oxide or the like, or using silver, aluminum, or the like to have a thickness of several nm to several tens of nm so that visible light passes therethrough.

The hole injecting layer 111 is a layer having a function of helping injection of holes into the hole transporting layer 112 from the first electrode 101. Providing the hole injecting layer 111 makes it possible to alleviate the difference in ionization potential between the first electrode 101 and the hole transporting layer 112 so that holes are easily injected. The hole injecting layer 111 is preferably formed by using a substance of which the ionization potential is lower than that of a substance which forms the hole transporting layer 112 and higher than that of a substance which forms the first electrode 101, or a substance in which an energy band is bent when being provided as a thin film with a thickness of 1 to 2 nm between the hole transporting layer 112 and the first electrode 101. As a specific example of a substance that can be used for forming the hole injecting layer 111, phthalocyanine (abbreviation: $H_2Pc$) and a phthalocyanine-based compound such as copper phthalocyanine (abbreviation: CuPc), a high molecular compound such as a poly(ethylene dioxythiophene)/poly(styrene sulfonate) aqueous solution (abbreviation: PEDOT/PSS), or the like can be given. That is, the hole injecting layer 111 can be formed by selecting a substance by which the ionization potential of the hole injecting layer 111 is relatively lower than the ionization potential of the hole transporting layer 112 from among hole transporting substances. Further, in the case of providing the hole injecting layer 111, the first electrode 101 is preferably formed using a substance having a high work function such as indium tin oxide.

The hole transporting layer 112 is a layer having a function of transporting holes injected from the first electrode 101 side to the light emitting layer 113. Thus, providing the hole transporting layer 112 makes it possible to isolate the first electrode 101 from the light emitting layer 113. Consequently, it is possible to prevent light emission from being quenched due to a metal contained in the first electrode 101 and the like. The hole transporting layer is preferably formed using a hole transporting substance. In particular, a substance having a hole mobility of $1 \times 10^{-6}$ cm$^2$/Vs or more is preferably used for forming the hole transporting layer. The hole transporting substance is a substance of which the hole mobility is higher than the electron mobility and a ratio of the hole mobility to the electron mobility (i.e., the hole mobility/the electron mobility) is preferably more than 100. As a specific example of a substance that can be used for forming the hole transporting layer 112, 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4"-tris(N-carbazolyl)triphenylamine (abbreviation: TCTA), phthalocyanine (abbreviation: $H_2Pc$), copper phthalocyanine (abbreviation: CuPc), vanadyl phthalocyanine (abbreviation: VOPc), 4,4'-bis[N-(4-biphenylyl)-N-phenylamino]biphenyl (abbreviation: BBPB), and the like can be given. Note that it is more preferable to form the hole transporting layer 112 by selecting from among hole transporting substances a substance in particular having a larger energy gap than a substance used as a host. Further, the hole transporting layer 112 may be a layer having a multilayer structure that is formed by combining two or more layers including the above mentioned substances.

It is preferable that the light emitting layer 113 is a layer in which the anthracene derivative represented by General Formula (7) or (8) is dispersed in a layer containing a substance (termed "host") having a larger energy gap than that of the anthracene derivative, as well as a higher ionization potential than that of the anthracene derivative. This can prevent light emission from the anthracene derivative from being quenched due to a concentration of the anthracene derivative itself. Note that the energy gap refers to an energy gap between a LUMO level and a HOMO level.

More specifically, a substance used as a host is preferably a substance that has an ionization potential higher than 5.4 eV and an energy gap larger than 2.8 eV, and has a higher electron transporting property than a hole transporting property. As such a substance, for example, an anthracene derivative such as t-BuDNA, CzPA, and diphenyl anthracene; a phenanthroline derivative such as BCP; an oxadiazole derivative; and a triazine derivative can be given. One substance or two or more substances selected from these substances may be mixed with the anthracene derivative represented by General Formula (7) or (8), so that the anthracene derivative is in a dispersed state. By the light emitting layer 113 having such structure, the anthracene derivative represented by General Formula (7) or (8) can efficiently trap holes, and as a result, a light emitting element with good light emission efficiency can be obtained. The electron transporting layer 114 is often formed of a substance having a small energy gap, and it is easy for excitation energy from the light emitting layer 113 to move; however, by the light emitting layer 113 having a structure such as that above, a recombination region (light emission region) of holes and electrons in the light emitting layer 113 is formed on a hole transporting layer 112 side, and moving of excitation energy to the electron transporting layer 114 can be prevented. As a result, degradation of chromaticity due to light emission occurring in a layer that is not the light emitting layer 113 can be prevented. Note that a layer in which a plurality of compounds are mixed, such as the light emitting layer 113, can be formed using a co-evaporation method. Here, the co-evaporation method refers to an evaporation method in which raw materials from a plurality of evaporation sources provided in a single treatment chamber are each vaporized, the vaporized raw materials are mixed in a gaseous state, and then deposited over a treatment object.

The electron transporting layer is a layer having a function of transporting electrons injected from the second electrode 102 to the light emitting layer 113. Thus, providing the electron transporting layer 114 makes it possible to isolate the second electrode 102 from the light emitting layer 113. Consequently, it is possible to prevent light emission from being quenched due to a metal contained in the second electrode 102 and the like. The electron transporting layer is preferably formed using an electron transporting substance. In particular, a substance having an electron mobility of $1 \times 10^{-6}$ cm$^2$/Vs or more is preferably used for forming the electron transporting layer. The electron transporting substance is a substance of which the electron mobility is higher than the hole mobility and a ratio of the electron mobility to the hole mobility (i.e., the electron mobility/the hole mobility) is preferably more than 100. As a specific example of a substance that can be used for forming the electron transporting layer 114, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]-quinolinato)beryllium (abbreviation: BeBq$_2$), bis(2-methyl-8-quinolinolato)-4-phenylphenolato-aluminum (abbreviation: BAlq), bis[2-(2-hydroxyphenyl)benzoxazolato]zinc (abbreviation: Zn(BOX)$_2$), and bis[2-(2-hydroxyphenyl)benzothiazolato]zinc (abbreviation: Zn(BTZ)$_2$) can be given. In addition, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ),3-(4-tert-butylphenyl)-4-(4-ethylphenyl)-5-(4-biphenylyl)-1,2,4-triazole (abbreviation: p-Et-TAZ), bathophenanthroline (abbreviation: BPhen), bathocuproine (abbreviation: BCP), 4,4-bis(5-methylbenzoxazole-2-yl) stilbene (abbreviation: BzOs), and the like can be given. Note that it is more preferable to form the electron transporting layer 114 by selecting from among electron transporting substances a substance in particular having a larger energy gap than a substance used as a host. Further, the electron transporting layer 114 may be a layer having a multilayer structure that is formed by combining two or more layers including the above mentioned substances.

The electron injecting layer 115 is a layer having a function of helping injection of electrons to the electron transporting layer 114 from the second electrode 102. The electron injecting layer 115 can be formed using a substance selected from among substances that can be used to form the electron transporting layer 114 such as BPhen, BCP, p-EtTAZ, TAZ, and BzOs, that has a relatively high electron affinity than a substance used to form the electron transporting layer 114. By forming the electron injecting layer 115 in this manner, a difference in electron affinity between the second electrode 102 and the electron transporting layer 114 is alleviated, and electrons are easily injected. Also, the electron injecting layer 115 may include an inorganic substance such as an alkali metal like Li or Cs; an oxide of an alkali metal such as lithium oxide ($Li_2O$), potassium oxide ($K_2O$), or sodium oxide ($Na_2O$); an oxide of an alkali earth metal such as calcium oxide (CaO) or magnesium oxide (MgO); a fluoride of an alkali metal such as lithium fluoride (LiF) or cesium fluoride (CsF); a fluoride of an alkali earth metal such as calcium fluoride ($CaF_2$); or an alkali earth metal such as Mg or Ca. Further, the electron injecting layer 115 may have a structure of containing an organic substance as in the above, or a structure of containing an inorganic substance such as a fluoride of an alkali metal such as LiF, or a fluoride of an alkali earth metal such as $CaF_2$. In this manner, by providing the electron injecting layer 115 as a thin film of 1 to 2 nm using an inorganic substance such as a fluoride of an alkali metal such as LiF, or a fluoride of an alkali earth metal such as $CaF_2$, an energy band of the electron injecting layer 115 becomes bent, or a tunnel current flows through the electron injecting layer 115, and injection of electrons from the second electrode 102 to the electron transporting layer 114 becomes easy.

Note that a hole generating layer may be provided instead of the hole injecting layer 111, or an electron generating layer may be provided instead of the electron injecting layer 115.

Here, the hole generating layer refers to a layer that generates holes. The hole generating layer can be formed by mixing at least one substance selected from among hole transporting substances and a substance showing an electron accepting property with respect to the hole transporting substance. Here, as the hole transporting substance, a similar substance to a substance that can be used to form the hole transporting layer 112 can be used. Also, as the substance showing an electron accepting property, a metal oxide such as molybdenum oxide, vanadium oxide, ruthenium oxide, or rhenium oxide is preferably used.

Further, an electron generating layer refers to a layer that generates electrons. The electron generating layer can be formed by mixing at least one substance selected from among electron transporting substances and a substance showing an electron donating property with respect to the electron transporting substance. Here, as the electron transporting substance, a similar substance to a substance that can be used to form the electron transporting layer 114 can be used. Also, as the substance showing electron donating property, a substance selected from among alkali metals and alkali earth metals, specifically, lithium (Li), calcium (Ca), sodium (Na), potassium (K), magnesium (Mg) or the like can be used.

A mode of a light emitting element such as that above can be manufactured by a manufacturing method of forming the first electrode 101; laminating and forming the hole injecting layer 111, the hole transporting layer 112, the light emitting layer 113, the electron transporting layer 114, and the electron injecting layer 115 in this order thereover; and then forming the second electrode 102. Alternatively, it can be manufactured by a manufacturing method of forming the second electrode 102; laminating and forming the electron injecting layer 115, the electron transporting layer 114, the light emitting layer 113, the hole transporting layer 112, and the hole injecting layer 111 in this order thereover; and then forming the first electrode 101. Note that the hole injecting layer 111, the hole transporting layer 112, the light emitting layer 113, the electron transporting layer 114, and the electron injecting layer 115 may each be formed by any method of an evaporation method, an inkjet method, a coating method, or the like. Further, the first electrode 101 or the second electrode 102 may be formed using any method of a sputtering method, an evaporation method, or the like.

Since the light emitting element of the present invention having the above described structure is manufactured using a compound containing an anthracene skeleton or an amine skeleton like an anthracene derivative of the present invention, there are few changes in characteristic of the light emitting element due to changes in property of a light emitting substance caused by repetition of an oxidation reaction. As a result, the light emitting element can emit light stably for a long period of time. Further, since it is manufactured using the anthracene derivative of the present invention, blue light emission with good chromaticity can be exhibited.

Embodiment Mode 5

Since the light emitting element of the present invention described in Embodiment Mode 4 has resistance to repetition of an oxidation reaction and can emit light in a favorable state for a long period of time, by using a light emitting element of the present invention, a light emitting device that can provide a favorable displayed image and the like for a long period of time can be obtained. Further, since the light emitting element of the present invention described in Embodiment Mode 4 can exhibit blue light emission with good chromaticity, a light emitting device that exhibits blue light emission with good chromaticity that displays an image having excellent colors can be obtained.

In this embodiment mode, a circuit structure and a driving method of a light emitting device having a display function are described with reference to FIGS. 2 to 5.

Figure 2:
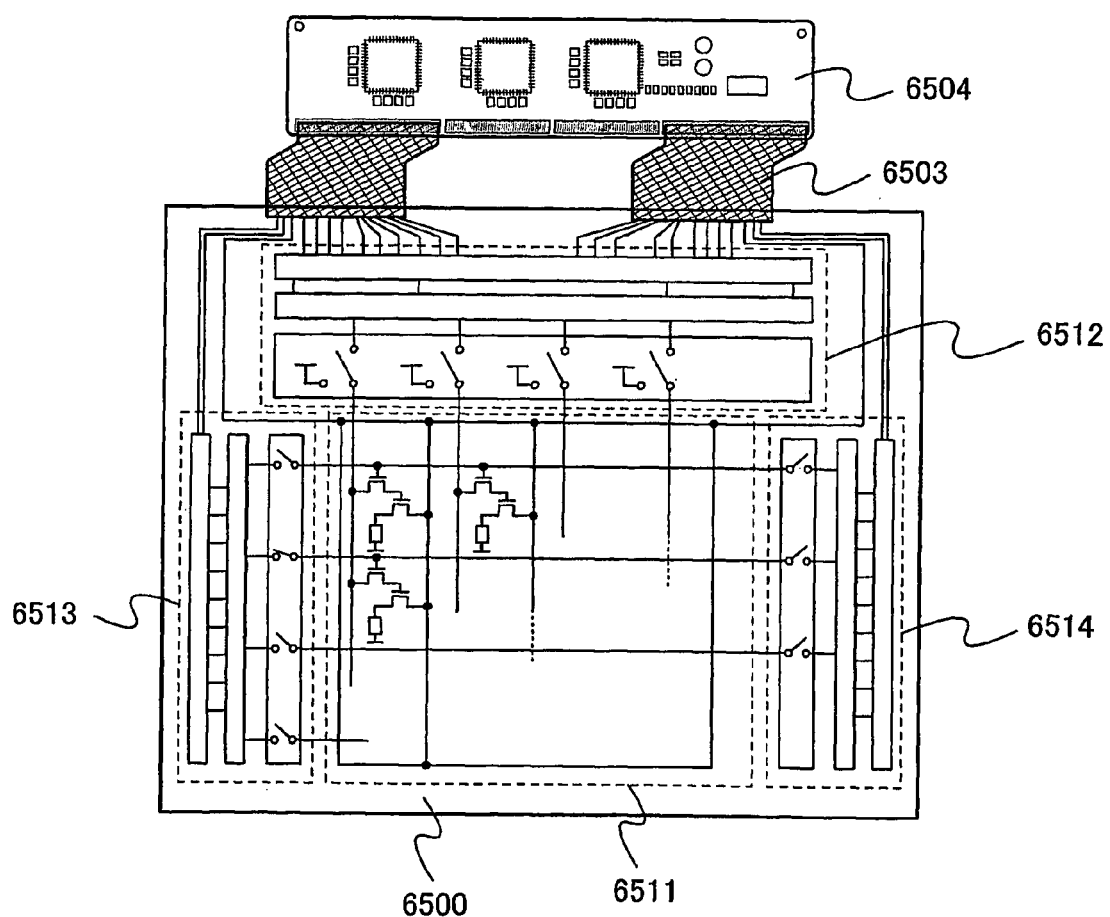
FIG. 2 is a view describing a mode of a light emitting device of the present invention.

FIG. 2 is a schematic top view of a light emitting device to which the present invention is applied. In FIG. 2, a pixel portion 6511, a source signal line driving circuit 6512, a writing gate signal line driving circuit 6513, and an erasing gate signal line driving circuit 6514 are provided over a substrate 6500. Each of the source signal line driving circuit 6512, the writing gate signal line driving circuit 6513, and the erasing gate signal line driving circuit 6514 is connected to FPCs (flexible printed circuits) 6503 that are external input terminals through a group of wirings. Further, each of the source signal line driving circuit 6512, the writing gate signal line driving circuit 6513, and the erasing gate signal line driving circuit 6514 receives signals such as a video signal, a clock signal, a start signal, and a reset signal from the FPCs 6503. In addition, a printed wiring board (PWB) 6504 is attached to the FPCs 6503. It is not always necessary to provide the driving circuit portion over the same substrate as the pixel portion 6511 as described above. For example, the driving circuit portion may be provided outside the substrate by using a TCP (Tape Carrier Package) in which an IC chip is mounted over an FPC where a wiring pattern is formed, or the like.

In the pixel portion 6511, a plurality of source signal lines extending in columns are arranged in rows. In addition, current-supply lines are arranged in rows, and a plurality of gate signal lines extending in rows are arranged in columns in the pixel portion 6511. Further, a plurality of pairs of circuits each containing a light emitting element are arranged in the pixel portion 6511.

Figure 3:
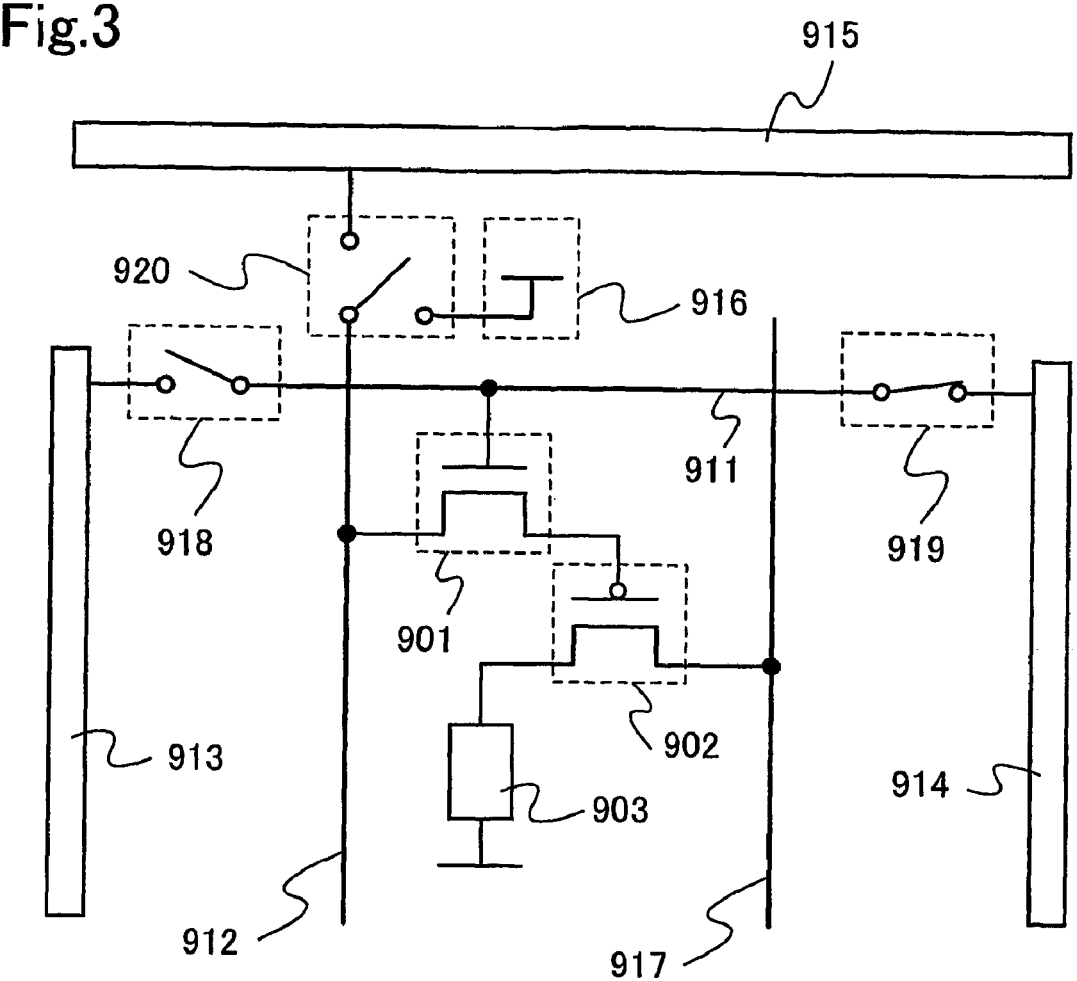
FIG. 3 is a view describing a circuit-contained in a light emitting device of the present invention.

FIG. 3 shows a circuit for operating one pixel. The circuit shown in FIG. 3 contains a first transistor 901, a second transistor 902, and a light emitting element 903.

Each of the first transistor 901 and the second transistor 902 is a three-terminal element containing a gate electrode, a drain region, and a source region, and includes a channel region between the drain region and the source region. Here, since a source region and a drain region are switched with each other in accordance with a structure or operating conditions of a transistor, it is difficult to identify which one is the drain region or the source region. Therefore, in this embodiment mode, regions that serve as a source or a drain are referred to as a first electrode and a second electrode, respectively.

A gate signal line 911 and a writing gate signal line driving circuit 913 are provided so as to be electrically connected or disconnected by a switch 918. The gate signal line 911 and an erasing gate signal line driving circuit 914 are provided so as to be electrically connected or disconnected by a switch 919. Further, a source signal line 912 is provided so as to be electrically connected to any of a source signal line driving circuit 915 and a power source 916 by a switch 920. A gate of the first transistor 901 is electrically connected to the gate signal line 911, a first electrode of the first transistor is electrically connected to the source signal line 912, and a second electrode is electrically connected to a gate electrode of the second transistor 902. A first electrode of the second transistor 902 is electrically connected to a current-supply line 917 and a second electrode is electrically connected to one electrode contained in the light emitting element 903. It is to be noted that the switch 918 may be contained in the writing gate signal line driving circuit 913, the switch 919 may be contained in the erasing gate signal line driving circuit 914, and the switch 920 may be contained in the source signal line driving circuit 915.

Figure 4:
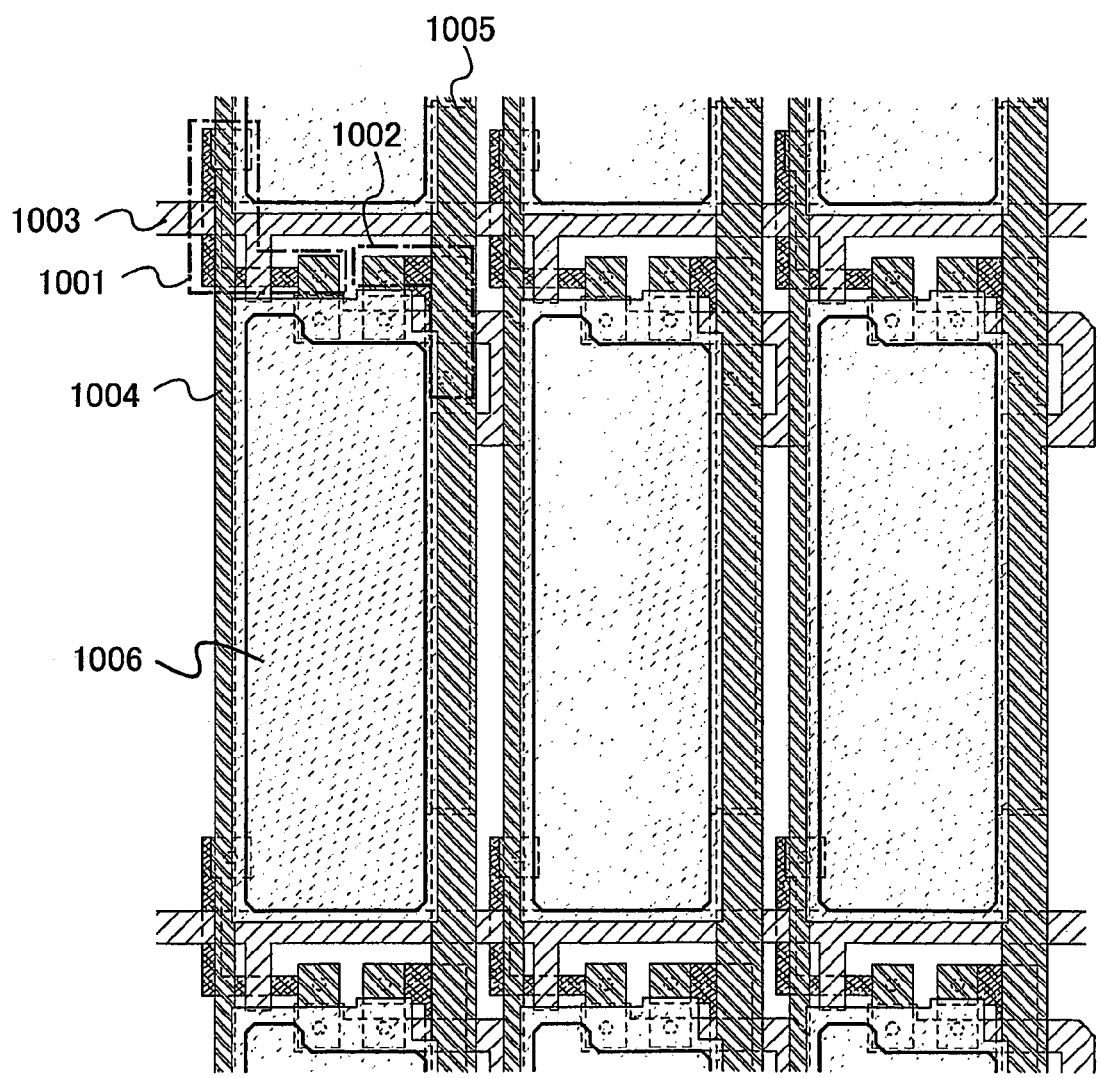
FIG. 4 is a top view describing a mode of a light emitting device of the present invention.

In addition, an arrangement of a transistor, a light emitting element, and the like in a pixel portion is not particularly limited. For example, the arrangement shown in a top view of FIG. 4 can be employed. In FIG. 4, a first electrode of a first transistor 1001 is connected to a source signal line 1004 and a second electrode is connected to a gate electrode of a second transistor 1002. Moreover, a first electrode of the second transistor 1002 is connected to a current-supply line 1005 and a second electrode is connected to an electrode 1006 of a light emitting element. A part of a gate signal line 1003 serves as a gate electrode of the first transistor 1001.

Next, a driving method will be explained. FIG. 5 is a diagram illustrating an operation per frame in accordance with passage of time. In FIG. 5, the horizontal direction indicates passage of time, and the vertical direction indicates the number of scanning stages of gate signal lines.

When a light emitting device of the present invention is used to display images, a rewrite operation and a display operation for a screen are repeated in a display period. Although the number of rewrites is not particularly limited, it is preferable that the number of rewrites be at least about 60 times per second so as not to make a viewer notice flickers. Here, a period in which a rewrite operation and a display operation are performed for a screen (one frame) is referred to as one frame period.

As shown in FIG. 5, one frame period is divided into four sub-frames 501, 502, 503, and 504 containing writing periods 501*a*, 502*a*, 503*a*, and 504*a*, and retention periods 501*b*, 502*b*, 503*b*, and 504*b*, respectively. A light emitting element to which a signal for emitting light is given is made to be in an emitting state in a retention period. The ratio of the length of the retention period in each sub-frame is, the first sub-frame 501: the second sub-frame 502: the third sub-frame 503: the fourth sub-frame $504 = 2^3 : 2^2 : 2^1 : 2^0 = 8:4:2:1$. This makes 4-bit gradation possible. However, the number of bits and the number of gradations are not limited to the ones described here. For example, eight sub-frames may be provided so as to perform 8-bit gradation.

An operation in one frame period will be explained. First, in the sub-frame 501, writing operations are sequentially performed for a first row to a last row. Consequently, the start time of writing period is different depending on the rows. In rows for which the writing period 501*a* is completed, the state is shifted sequentially into the retention period 501*b*. In the retention periods, a light emitting element to which a signal for emitting light is given is made to be in an emitting state. In addition, in rows for which the retention period 501*b* is completed, the state is shifted sequentially into the next sub-frame 502, and writing operations are sequentially performed for the first row to the last row as in the case of the sub-frame 501. Such operations as described above are repeated until the retention period 504*b* of the sub-frame 504 is completed. When the operation in the sub-frame 504 is completed, the next frame begins. Thus, a total of the time for which light is emitted in each sub-frame is emission time for each light emitting element in one frame. By varying this emission time for each light emitting element to have various combinations in one pixel, various display colors with different luminosity and chromaticity can be made.

As in the sub-frame 504, when forcible termination of a retention period of a row for which writing has been already completed and which is moved into the retention period is required before writing for the last row is completed, it is preferable that an erasing period 504*c* be provided after the retention period 504*b* and a row be controlled so as to be in a non-emitting state forcibly. Then, the row forcibly made to be in the non-emitting state is kept in the non-emitting state for a certain period of time (this period is referred to as a non-emission period 504*d*). Then, immediately after the writing period of the last row is completed, the state is shifted sequentially into the writing period (or the next frame), starting from the first row. This makes it possible to prevent the writing period of the sub-frame 504 from overlapping with the writing period of the next sub-frame.

Although the sub-frames 501 to 504 are arranged in the order from the longest retention period to the shortest in this embodiment mode, the arrangement as in this embodiment mode is not always necessary. For example, the sub-frames 501 to 504 may be arranged in the order from the shortest retention period to the longest, or may be arranged in random order. In addition, the sub-frames may be further divided into a plurality of frames. In other words, scanning of the gate signal lines may be performed plural times while giving the same video signal.

Now, an operation of the circuit shown in FIG. 3 in a writing period and an erasing period will be explained.

First, an operation in a writing period will be explained. In the writing period, the gate signal line 911 in an n-th row (n is a natural number) is electrically connected to the writing gate signal line driving circuit 913 through the switch 918, and disconnected to the erasing gate signal line driving circuit 914. In addition, the source signal line 912 is electrically connected to the source signal line driving circuit 915 through the switch 920. Here, a signal is inputted to the gate of the first transistor 901 connected to the gate signal line 911 in the n-th row (n is a natural number) to turn on the first transistor 901. Then, at this time, video signals are inputted at the same time to the source signal lines 912 in the first to the last columns. It is to be noted that the video signals inputted from the source signal lines 912 to the respective columns are independent of each other. The video signal inputted from the source signal line 912 is inputted to the gate electrode of the second transistor 902 through the first transistor 901 connected to each of the source signal lines 912. At this time, whether the light emitting element 903 emits light or not is determined depending on the signal inputted to the second transistor 902. For example, when the second transistor 902 is a p-channel transistor, the light emitting element 903 emits light by inputting a Low Level signal to the gate electrode of the second transistor 902. On the other hand, when the second transistor 902 is an n-channel transistor, the light emitting element 903 emits light by inputting a High Level signal to the gate electrode of the second transistor 902.

Next, an operation in an erasing period will be explained. In the erasing period, the gate signal line 911 in an n-th row (n is a natural number) is electrically connected to the erasing gate signal line driving circuit 914 through the switch 919 and disconnected to the wiring gate signal line driving circuit 913. In addition, the source signal line 912 is electrically connected to the power source 916 through the switch 920. Here, a signal is inputted to the gate of the first transistor 901 connected to the gate signal line 911 in the n-th row to turn on the first transistor 901. Then, at this moment, erasing signals are inputted at the same time to the source signal lines 912 in the first to last columns. The erasing signal inputted from the source signal lines 912 is inputted to the gate electrode of the second transistor 902 through the first transistor 901 connected to each of the source signal lines. At this moment, current supply from the current-supply line 917 to the light emitting element 903 is stopped by the signal inputted to the second transistor 902. Then, the light emitting element 903 is forcibly made to emit no light. For example, when the second transistor 902 is a p-channel transistor, the light emitting element 903 emits no light by inputting a High Level signal to the gate electrode of the second transistor 902. On the other hand, when the second transistor 902 is an n-channel transistor, the light emitting element 903 emits no light by inputting a Low Level signal to the gate electrode of the second transistor 902.

It is to be noted that, as for an n-th row (n is a natural number), signals for erasing are inputted by the operation as described above in an erasing period. However, as described above, another row (referred to as an m-th row (m is a natural number)) may be in a writing period while the n-th row is in an erasing period. In such a case, it is necessary to input a signal for erasing to the n-th row and input a signal for writing to the m-th row by using the source signal line in the same column. Therefore, an operation that will be explained below is preferable.

Immediately after the light emitting element 903 in the n-th row is made to emit no light by the operation in the erasing period as explained above, the gate signal line 911 and the erasing gate signal line driving circuit 914 are made to be disconnected to each other, and the switch 920 is switched to connect the source signal line 912 and the source signal line driving circuit 915. Then, in addition to connecting the source signal line 912 to the source signal line driving circuit 915, the gate signal line 911 is connected to the writing gate signal line driving circuit 913. Then, a signal is inputted selectively to the gate signal line 911 in the m-th row from the writing gate signal line driving circuit 913 to turn on the first transistor 901, and signals for writing are inputted to the source signal line 912 in the first to last columns from the source signal line driving circuit 915. This signal makes the light emitting element 903 in the m-th row be in an emitting or non-emitting state.

Immediately after the writing period for the m-th row is completed as described above, an erasing period for an (n+1) th row is started. For that purpose, the gate signal line 911 and the writing gate signal line driving circuit 913 are made to be disconnected to each other, and the switch 920 is switched to connect the source signal line 912 and the power source 916. Further, the gate signal line 911 is made to be disconnected to the writing gate signal line driving circuit 913, and to be connected to the erasing gate signal line driving circuit 914. Then, a signal is inputted selectively to the gate signal line in the (n+1)th row from the erasing gate signal line driving circuit 914 to turn on the first transistor 901, and an erasing signal is inputted from the power source 916. Immediately after the erasing period for the (n+1)th row is thus completed, a writing period for the (m+1)th row is started. Then, an erasing period and a writing period may be repeated in the same way until an erasing period for the last row is completed.

Although a mode in which the writing period for the m-th row is provided between the erasing period for the n-th row and the erasing period for the (n+1)th row is explained in this embodiment mode, the present invention is not limited thereto. The writing period for the m-th row may be provided between an erasing period for an (n−1)th row and an erasing period for the n-th row as well.

In addition, in this embodiment mode, an operation is repeated in which the erasing gate signal line driving circuit 914 and one gate signal line are made to be disconnected to each other as well as the writing gate signal line driving circuit 913 and another gate signal line are made to be connected to each other when the non-emission period 504d is provided as in the sub-frame 504. This type of operation may also be performed in a frame in which a non-emission period is not particularly provided.

Embodiment Mode 6

One mode of a light emitting device containing a light emitting element of the present invention will be described with reference to cross-sectional views in FIGS. 6A to 6C.

Figure 6A:
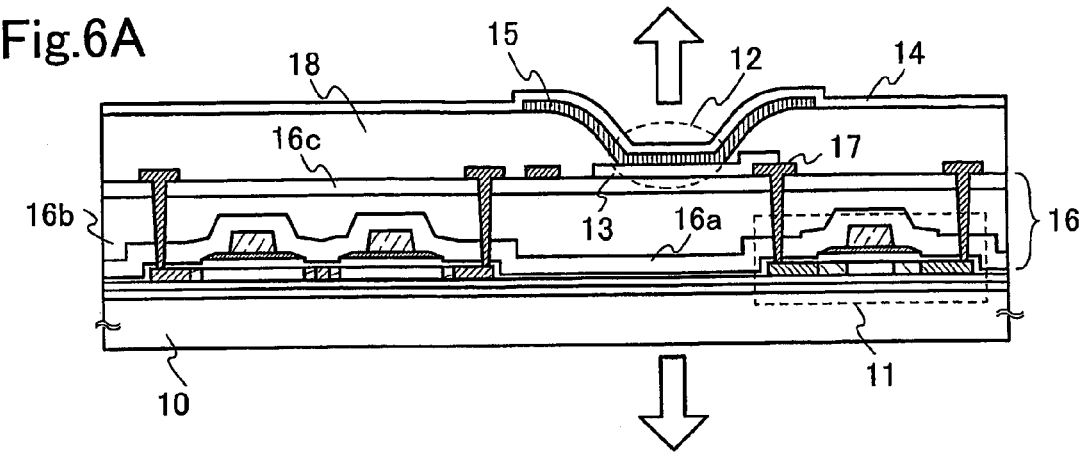
FIGS. 6A to 6C are views each describing a mode of a circuit contained in a light emitting device of the present invention.
Figure 6B:
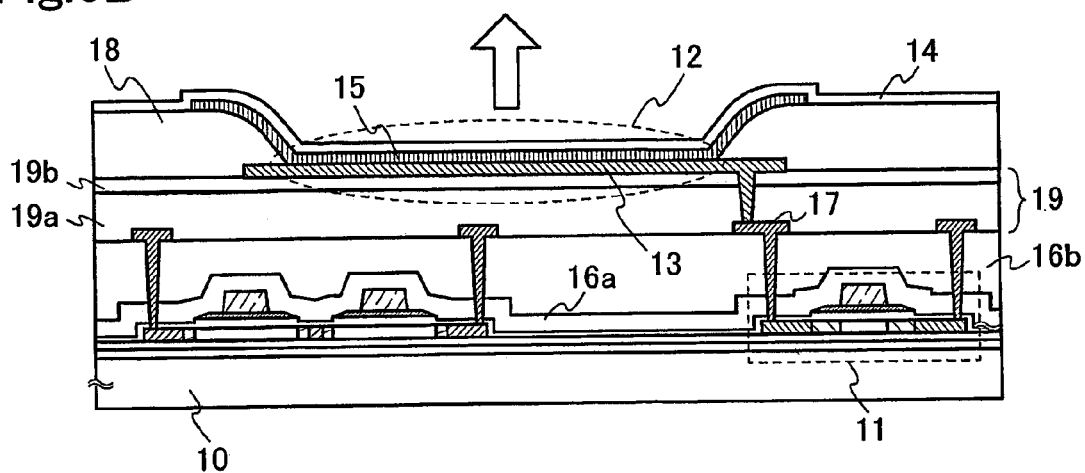
Figure 6C:
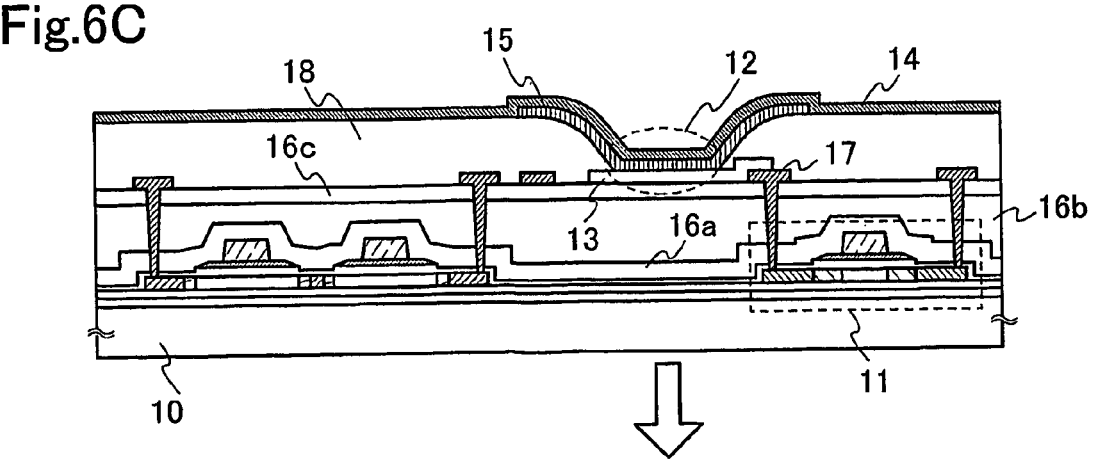

In each of FIGS. 6A to 6C, a box-shaped portion surrounded by a dotted line is a transistor 11 provided for driving a light emitting element 12 of the present invention. The light emitting element 12 is a light emitting element like the light emitting element described in Embodiment Mode 4 which has a light emitting layer 15 between a first electrode 13 and a second electrode 14, in which the light emitting layer 15 contains as a light emitting substance an anthracene derivative of the present invention manufactured using a carbazole derivative of the present invention. A drain of the transistor 11 and the first electrode 13 are electrically connected to each other by a wiring 17 penetrating through a first interlayer insulating film 16 (16a, 16b, and 16c). In addition, the light emitting element 12 is separated by a partition layer 18 from another light emitting element that is provided adjacently. A light emitting device having such a structure of the present invention is provided over a substrate 10 in this embodiment mode.

It is to be noted that the transistor 11 shown in each of FIGS. 6A to 6C is a top-gate TFT in which a gate electrode is provided on an opposite side of a substrate with a semiconductor layer as a center. However, a structure of the transistor 11 is not particularly limited. For example, a bottom-gate TFT may be used. In the case of a bottom-gate TFT, a TFT where a protective film is formed over a semiconductor layer that forms a channel (a channel-protected TFT) may be employed, or a TFT where a part of a semiconductor layer that forms a channel is depressed (a channel-etched TFT) may be employed.

In addition, a semiconductor layer which forms the transistor 11 may be either crystalline or amorphous, or alternatively, semi-amorphous or the like.

The following will describe a semi-amorphous semiconductor. The semi-amorphous semiconductor is a semiconductor that has an intermediate structure between amorphous and crystalline (including single-crystal or polycrystalline) structures and has a third state that is stable in terms of free energy, which contains a crystalline region that, has short range order and lattice distortion. Further, a crystal grain of 0.5 to 20 nm is included in at least a region in a film of the semi-amorphous semiconductor. Raman spectrum is shifted to a wave number side lower than 520 cm$^{-1}$. The diffraction peaks of (111) and (220), which are believed to be derived from silicon crystal lattice, are observed by the X-ray diffraction. The semi-amorphous semiconductor contains hydrogen or halogen of at least 1 atomic % or more for terminating dangling bonds. The semi-amorphous semiconductor is also referred to as a so-called microcrystalline semiconductor. A microcrystalline semiconductor can be formed by glow discharge decomposition (plasma CVD) with a gas selected from $SiH_4$, $Si_2H_6$, $SiH_2Cl_2$, $SiHCl_3$, $SiCl_4$, and $SiF_4$. Such a gas may also be diluted with $H_2$, or a mixture of $H_2$ and one or more of rare gas elements of He, Ar, Kr, and Ne. The dilution ratio is set to be in a range of 1:2 to 1:1000. The pressure is set to be approximately in the range of 0.1 to 133 Pa. The power frequency is set to be 1 to 120 MHz, preferably, 13 to 60 MHz. The substrate heating temperature may be set to be 300° C. or lower, more preferably, 100 to 250° C. As for impurity elements contained in the film, each concentration of impurities for atmospheric constituents such as oxygen, nitrogen and carbon is preferably set to be $1\times10^{20}$ cm$^3$ or lower. In particular, the oxygen concentration is set to be $5\times10^{19}$/cm$^3$ or lower, preferably, $1\times10^{19}$ cm$^3$ or lower.

Further, as specific examples of a crystalline semiconductor layer, a semiconductor layer including a single-crystal or polycrystalline silicon, or silicon-germanium is given, which may be formed by laser crystallization or may be formed by crystallization with a solid-phase growth method using an element such as nickel.

In the case of using an amorphous substance, for example, amorphous silicon to form the semiconductor layer, it is preferable that the light emitting device have a circuit in which the transistor 11 and other transistors (transistors constituting a circuit for driving the light emitting element) are all n-channel transistors. Other than that case, the light emitting device may have a circuit including either n-channel transistors or p-channel transistors, or may have a circuit including both n-channel transistors and p-channel transistors.

Further, the first interlayer insulating film 16 may be multilayered as shown in FIGS. 6A to 6C, or may be a single layer. It is to be noted that the first interlayer insulating film 16a contains an inorganic substance such as silicon oxide or silicon nitride, and the first interlayer insulating film 16b contains acrylic, siloxane (siloxane is a compound which its skeleton structure is structured by a bond between silicon (Si) and oxygen (O), and has a fluoro group, hydrogen, or an organic group (for example, an alkyl group or an aromatic hydrocarbon as a substituent), or a substance such as silicon oxide that can be formed by coating. In addition, the first interlayer insulating film 16c includes a silicon nitride film containing argon (Ar). The substances constituting each of the layers are not particularly limited; therefore, substances other than the substances mentioned here may also be used. Moreover, a layer containing a substance other than these substances may also be combined. In this way, both of an inorganic film and an organic film, or one of an inorganic film and an organic film may be used to form the first interlayer insulating film 16.

As for the partition layer 18, it is preferable that an edge portion has a shape varying continuously in curvature radius. In addition, acrylic, siloxane, resist, silicon oxide or the like is used to form the partition layer 18. One or both of an inorganic film and an organic film may be used to form the partition layer 18.

In each of FIGS. 6A and 6C, only the first interlayer insulating film 16 is provided between the transistor 11 and the light emitting element 12. However, as shown in FIG. 6B, a second interlayer insulating film 19 (19a and 19b) may be provided in addition to the first interlayer insulating film 16 (16a, 16b). In the light emitting device shown in FIG. 6B, the first electrode 13 is connected to the wiring 17, by penetrating through the second interlayer insulating film 19.

The second interlayer insulating film 19 may be multilayered or a single layer as in the case of the first interlayer insulating film 16. The second interlayer insulating film 19a contains a substance such as acrylic, siloxane, or silicon oxide that can be formed by coating. In addition, the second interlayer insulating film 19b includes a silicon nitride film containing argon (Ar). The substances constituting the respective layers are not particularly limited; therefore, substances other than the substances mentioned here may also be used. Moreover, a layer containing a substance other than these substances may also be combined. In this way, both of an inorganic film and an organic film, or a film made of one of an inorganic film and an organic film may be used to form the second interlayer insulating film 19.

In the light emitting element 12, in a case where both the first electrode and the second electrode are formed by using a light transmitting substance, emitted light can be extracted from both the first electrode 13 side and the second electrode 14 side as indicated by outline arrows of FIG. 6A. In the case where only the second electrode 14 is formed by using a light transmitting substance, emitted light can be extracted from only the second electrode 14 side as indicated by an outline arrow of FIG. 6B. In this case, it is preferable that the first electrode 13 is formed by using a highly reflective material, or a film composed of a highly reflective material (a reflective film) be provided below the first electrode 13. Further, in the case where only the first electrode 13 is formed by using a light transmitting substance, emitted light can be extracted from only the first electrode 13 side as indicated by an outline arrow of FIG. 6C. In this case, it is preferable that the second electrode 14 is formed by using a highly reflective material, or a reflective film be provided above the second electrode 14.

In addition, the light emitting layer 15 may be stacked so that the light emitting element 12 is operated when a voltage is applied so as to make the potential of the second electrode 14 higher than that of the first electrode 13. Alternatively, the light emitting layer 15 may be stacked so that the light emitting element 12 is operated when a voltage is applied so as to make the potential of the second electrode 14 lower than that of the first electrode 13. The transistor 11 is an n-channel transistor in the former case, and the transistor 11 is a p-channel transistor in the latter case.

Figure 7:
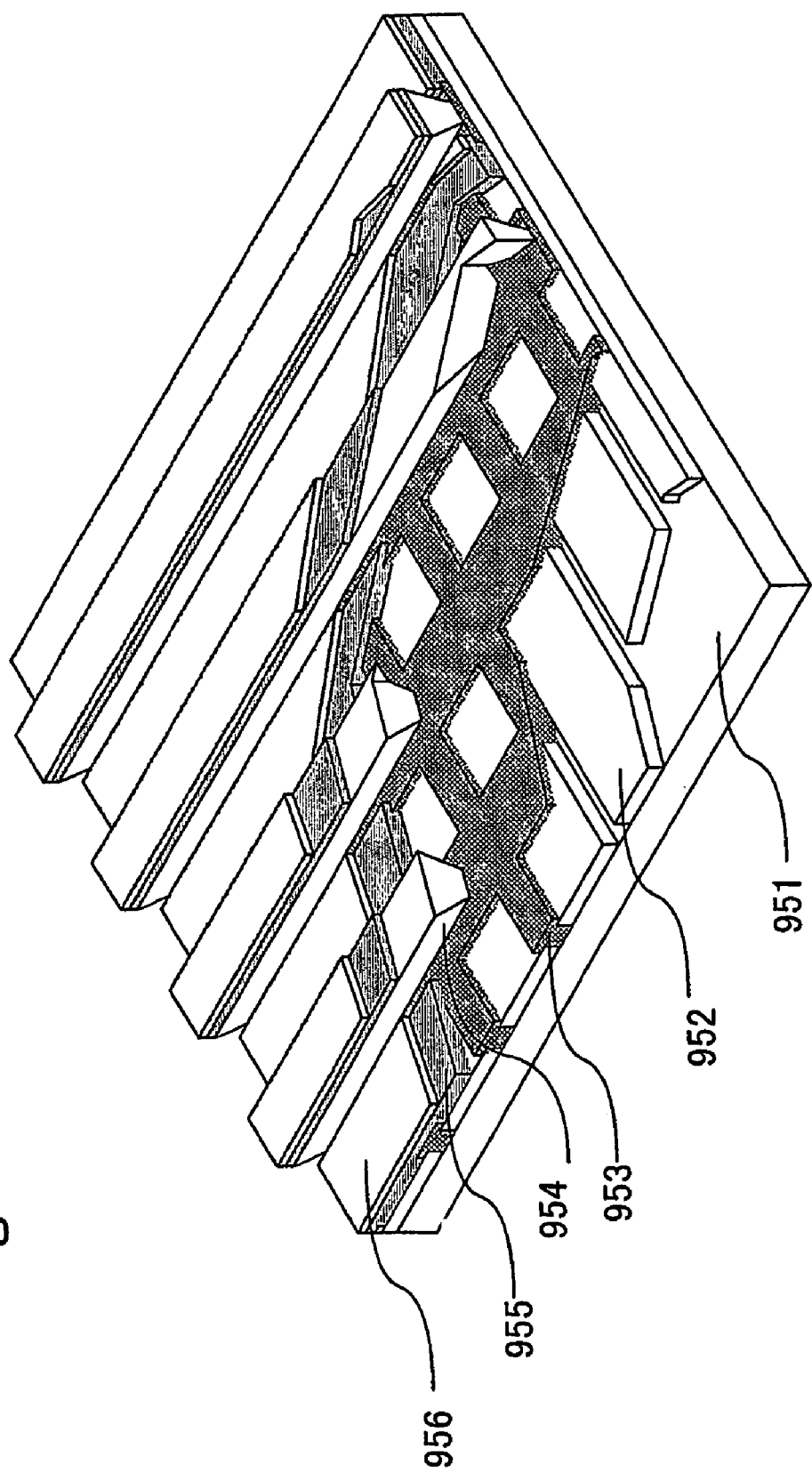
FIG. 7 is a cross-sectional view describing a mode of a light emitting device of the present invention.

In this embodiment mode, an active type light emitting device that controls driving of a light emitting element by a transistor has been described as in the above. However, the light emitting device may also be a passive type that drives a light emitting element without particularly providing an element for driving such as a transistor. FIG. 7 is a perspective view of a passive type light emitting device manufactured by applying the present invention. In FIG. 7, over a substrate 951, a layer 955 having a multilayered structure containing a light emitting layer, a layer containing an aromatic hydrocarbon and a metal oxide, and the like, is provided between an electrode 952 and an electrode 956. End portions of the electrode 952 are covered with an insulating layer 953. Further, a partition layer 954 is provided over the insulating layer 953. Side walls of the partition layer 954 are sloped so that a distance between one side wall and the other becomes shorter towards a substrate surface. In other words, a cross-section in a short side direction of the partition layer 954 has a trapezoidal shape, for which a bottom side (a side in the same direction as a plane direction of the insulating layer 953, and is in contact with the insulating layer 953) is shorter than an upper side (a side in the same direction as the plane direction of the insulating layer 953, and is not in contact with the insulating layer 953). In this manner, by providing the partition layer 954, malfunctioning of a light emitting element due to electrostatic discharge and the like can be prevented. Also, in a passive type light emitting device, by containing a light emitting element of the present invention that operates with low driving voltage, driving with low power consumption is possible.

Embodiment Mode 7

A light emitting device having a light emitting element manufactured using a light emitting element material of the present invention has resistance to repetition of an oxidation reaction, and can operate light emission in a favorable state for a long period of time. Therefore, by using such a light emitting device of the present invention for a display portion or a lighting portion, an electronic appliance that can provide a favorable displayed image for a long period of time, or an electronic appliance that can carry out favorable lighting for a long period of time can be obtained.

Figure 8A:
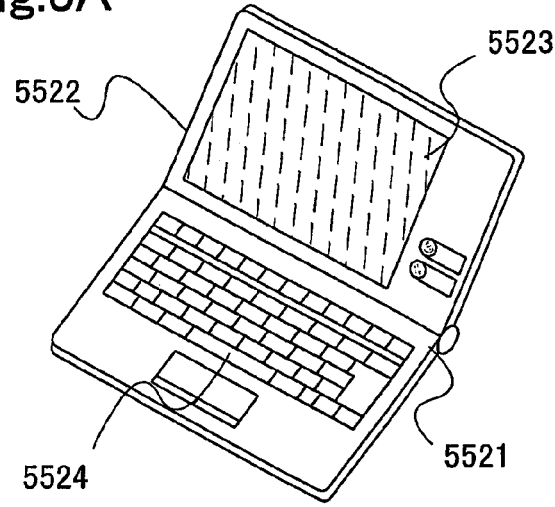
FIGS. 8A to 8C are views each describing a mode of an electronic appliance of the present invention.
Figure 8B:
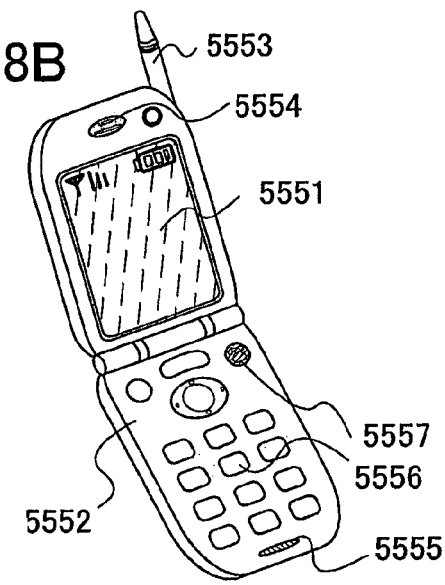
Figure 8C:
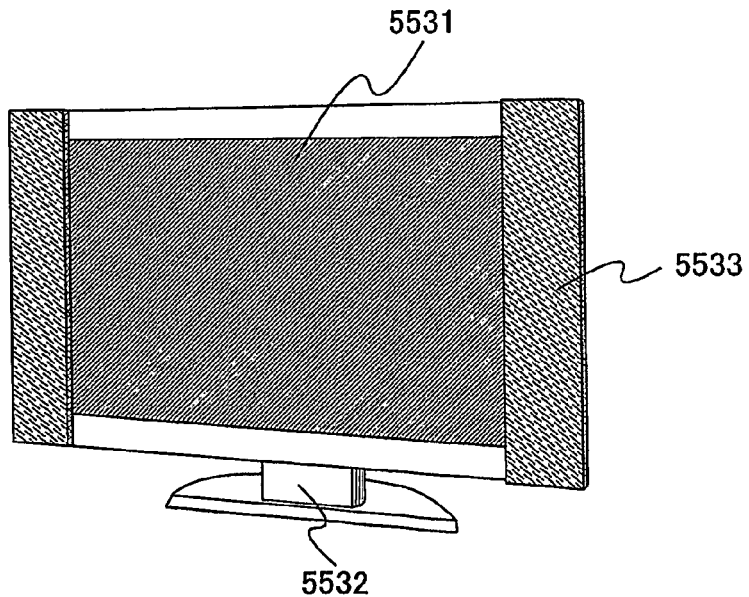

An example of an electronic appliance mounted with a light emitting device to which the present invention is applied, is shown in each of FIGS. 8A to 8C.

Figure 9:
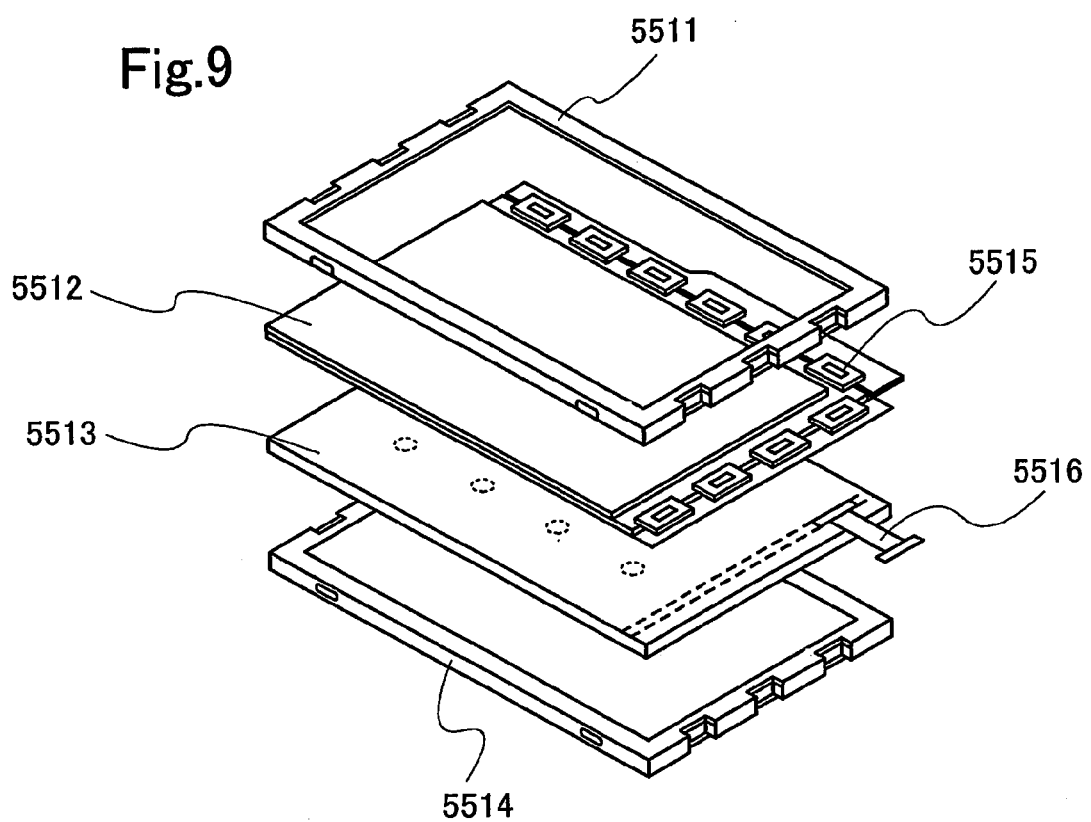
FIG. 9 is a view describing a mode of an electronic appliance of the present invention.

FIG. 8A is a personal computer manufactured by applying the present invention, which includes a main body 5521, a housing 5522, a display portion 5523, a keyboard 5524, and the like. By incorporating in the display portion a light emitting device (for example, a light emitting device including a structure such as those described in Embodiment Modes 3 and 4) using a light emitting element of the present invention such as those described in Embodiment Modes 1 and 2 as a pixel, a personal computer that can provide a displayed image with little defects in the display portion and no false recognition of the displayed image, having excellent colors, can be completed. Further, the personal computer can also be completed by incorporating as a backlight a light emitting device using the light emitting element of the present invention as a light source. Specifically, a lighting device in which a liquid crystal device 5512 and a light emitting device 5513 are fit into a housing 5511 and a housing 5514, may be incorporated as a display portion as shown in FIG. 9. Note that in FIG. 9, an external input terminal 5515 is attached to the liquid crystal device 5512, and an external input terminal 5516 is attached to the light emitting device 5513.

FIG. 8B is a telephone set manufactured by applying the present invention, which includes a main body 5552, a display portion 5551, an audio output portion 5554, an audio input portion 5555, operation switches 5556 and 5557, an antenna 5553, and the like. By incorporating a light emitting device including a light emitting element of the present invention as the display portion, a telephone set that can provide a displayed image with little defects in the display portion and no false recognition of the displayed image, having excellent colors, can be completed.

FIG. 8C is a television set manufactured by applying the present invention, which includes a display portion 5531, a housing 5532, a speaker 5533, and the like. By incorporating a light emitting device including a light emitting element of the present invention as the display portion, a television set that can provide a displayed image with little defects in the display portion and no false recognition of the displayed image, having excellent colors, can be completed.

As in the above, the light emitting device of the present invention is extremely suitable to be used in display portions for various electronic appliances. Note that the electronic appliance is not limited to those mentioned in this embodiment mode, and may be other electronic appliances as a navigation device and the like.

The present invention will be described in further detail below by embodiments. However, the present invention is not limited to these examples in any way.

EMBODIMENT 1

As one embodiment of a carbazole derivative of the present invention, a synthesis of the carbazole derivative represented by Structural Formula (1) will be described.

First, a method for synthesizing N-(4-bromophenyl)carbazole will be described. In a three-necked flask of 300 mL capacity, 56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were mixed and the atmosphere of the flask was substituted with nitrogen. Then, 8 mL of DMPU was added and stirred for 6 hours at 180° C. After the reaction mixture was cooled down to room temperature, a sediment was removed by suction filtration. The filtrate was washed with diluted hydrochloric acid, a saturated sodium hydrogen carbonate aqueous solution, and saturated saline in this order and then dried with magnesium sulfate. After the drying, the reaction mixture was naturally filtered and condensed, and then the obtained oil-like substance was purified by silica gel column chromatography (hexane:ethyl acetate=9:1) and recrystallized by chloroform and hexane. Then, a target substance, or, light-brown plate-like crystals were obtained in an amount of 20.7 g at a yield of 35%.

The $^1$H-NMR of the compound is shown below. $^1$H-NMR (300 MHz, DMSO-$d_6$) δ ppm: 8.14 (d, δ=7.8 Hz, 2H), 7.73 (d, δ=8.7 Hz, 2H), 7.46 (d, δ=8.4 Hz, 2H), 7.42-7.26 (m, 6H).

Further, a Synthesis Scheme (d-1) of N-(4-bromophenyl) carbazole is shown below.

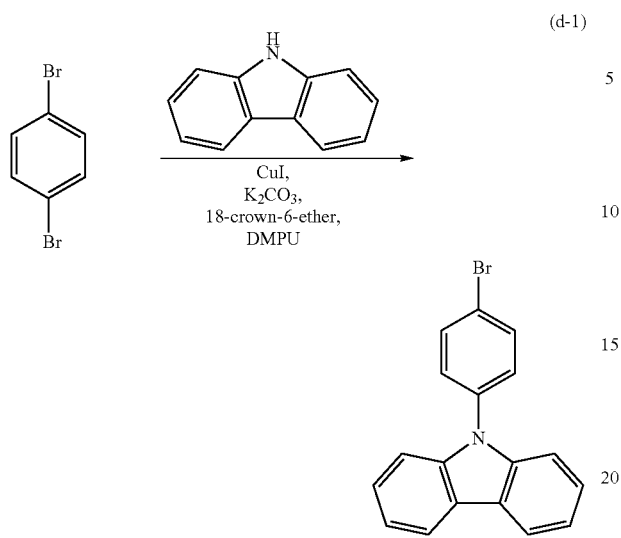

(d-1)

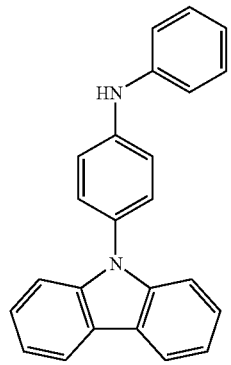

In a three-necked flask of 200 mL capacity, 5.4 g (17.0 mmol) of N-(4-bromophenyl)carbazole, 1.8 mL (20.0 mmol) of aniline, and 100 mg (0.17 mmol) of bis(dibenzylideneacetone)palladium (0) (abbreviation: Pd(dba)$_2$), and 3.9 g (40 mmol) of sodium-tert-butoxide (abbreviation: tert-BuONa) were mixed and the atmosphere of the flask was substituted with nitrogen. Then, 0.1 mL of tri-tert-butylphosphine (abbreviation: P(tert-Bu)$_3$) and 50 mL of toluene were added and stirred for 6 hours at 80° C. After the reaction mixture was filtered through Florisil®, celite, and alumina and the filtrate was washed with water and saturated saline, it was dried with magnesium sulfate. The reaction mixture was naturally filtered and condensed, and then the obtained oil-like substance was purified by silica gel column chromatography (hexane:ethyl acetate=9:1), whereby a target substance was obtained in an amount of 4.1 g at a yield of 73%. By using a nuclear magnetic resonance spectrometry ($^1$H-NMR), it was confirmed that this compound was 9-[4-(N-phenylamino)phenyl]carbazole (abbreviation: YGA).

Figure 10A:
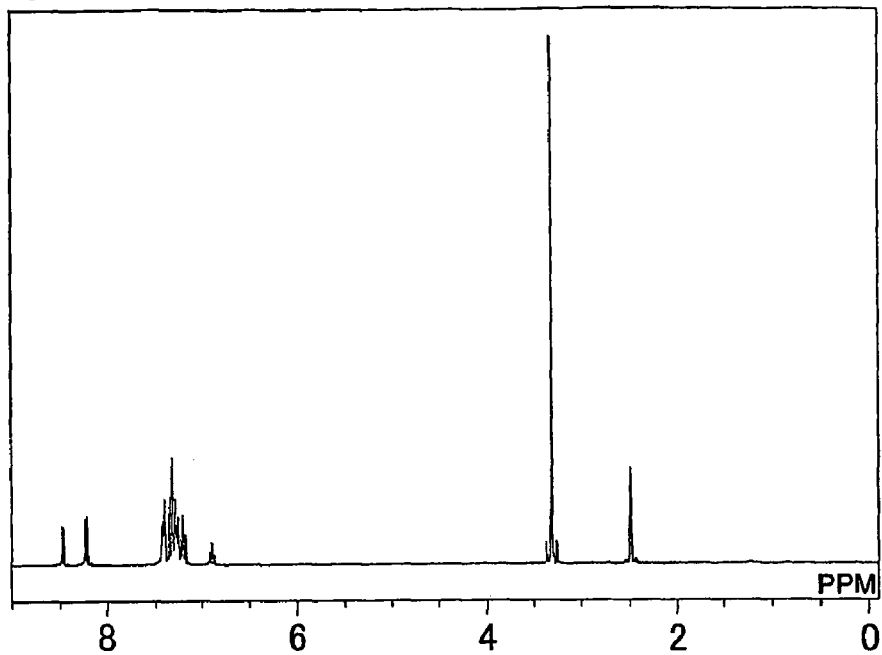
FIGS. 10A and 10B are each a $^1$H-NMR chart of a light emitting element material manufactured in Embodiment 1.
Figure 10B:
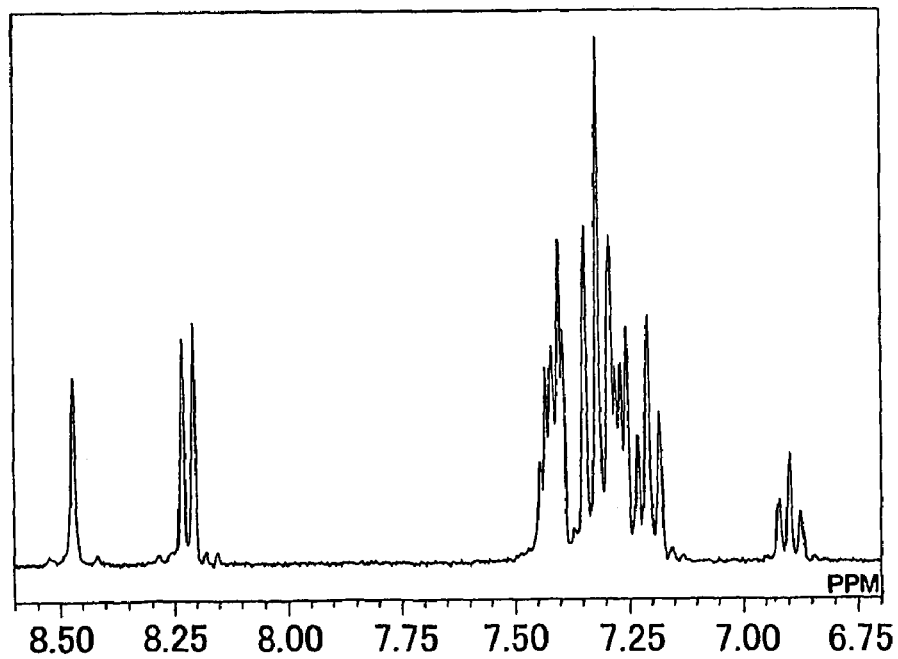

The $^1$H-NMR of the compound is shown below. A $^1$H-NMR chart is also shown in FIGS. 10A and 10B. Further, FIG. 10B is a chart showing an enlarged part in the range of 6.7 ppm to 8.6 ppm of FIG. 10A.

$^1$H-NMR (300 MHz, DMSO-d$_6$) δ ppm: 8.47 (s, 1H), 8.22 (d, δ=7.8 Hz, 2H), 7.44-7.16 (m, 14H), 6.92-6.87 (m, 1H).

Further, a synthesis scheme (d-2) of 9-[4-(N-phenylamino) phenyl]carbazole is shown below.

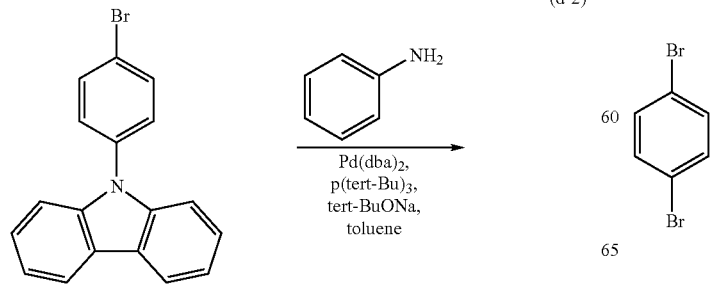

(d-2)

EMBODIMENT 2

A synthesis of an anthracene derivative of the present invention using the carbazole derivative obtained by Embodiment 1 will be described.

[Step 1: Synthesis of 9,10-bis(4-bromophenyl)-2-tert-butylanthracene]

Under nitrogen gas stream, 1.58 mol/L (13.4 mL) of a butyllithium hexane solution was dropped in a dried ether solution (200 mL) containing 5.0 g of 1,4-dibromobenzene at temperature of −78° C. After dropping the butyllithium hexane solution, the mixture was stirred for one hour at the same temperature. At a temperature of −78° C., a dried ether solution (40 mL) containing 2-tert-butyl anthraquinone (2.80 g) was dropped in the mixture, and then the reaction solution was heated slowly up to room temperature. After the reaction solution was stirred for about 12 hours at room temperature, water was added thereto, and an organic layer was extracted with ethyl acetate. The organic layer was washed with saturated saline and dried with magnesium sulfate. The dried matter was filtered and condensed. Then, the residue was purified by silica gel chromatography (developing solvent, hexane-ethyl acetate) to obtain 5.5 g of a compound.

When the thus obtained compound was measured by a nuclear magnetic resonance spectrometry ($^1$H-NMR), it was confirmed that the compound was 9,10-bis(4-bromophenyl)-2-tert-butyl-9,10-dihydroxy-9,10-dihydroanthracene.

The $^1$H-NMR of the compound is shown as follows. $^1$H-NMR (300 MHz, CDCl$_3$); δ=1.31 (s, 9H), 2.81 (s, 1H), 2.86 (s, 1H), 6.82-6.86 (m, 4H), 7.13-7.16 (m, 4H), 7.36-7.43 (m, 3H), 7.53-7.70 (m, 4H).

Moreover, a synthesis scheme (e-1) of the 9,10-bis(4-bromophenyl)-2-tert-butyl-9,10-dihydroxy-9,10-dihydroanthracene is shown below.

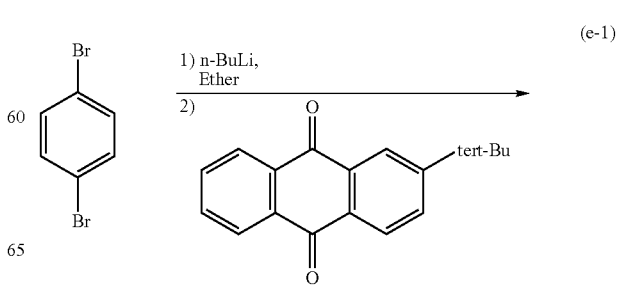

(e-1)

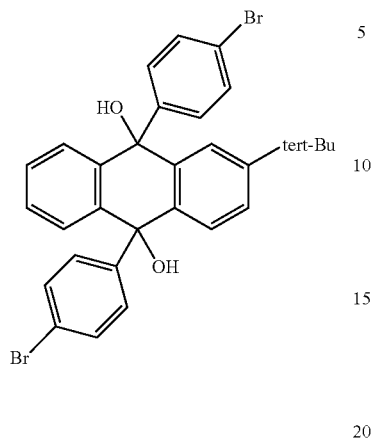

Under atmospheric air, 987 mg (1.55 mmol) of the thus obtained 9,10-bis(4-bromophenyl)-2-tert-butyl-9,10-dihydroxy-9,10-dihydroanthracene, 664 mg (4 mmol) potassium iodide, and 1.48 g (14 mmol) of sodium phosphate acid dihydrate were suspended with 12 mL of glacial acetic acid. The mixture was heated to reflux and stirred for two hours. The mixture was cooled down to room temperature and a generated precipitate was filtered and washed with about 50 mL of methanol to obtain a filtrate. The filtrate was dried to obtain 700 mg of a compound which was a light yellow powder. The yield was 82%. When this compound was measured by a nuclear magnetic resonance spectrometry ($^1$H-NMR, $^{13}$C-NMR), it was confirmed that the compound was 9,10-bis(4-bromophenyl)-2-tert-butylanthracene.

The $^1$H-NMR and the $^{13}$C-NMR of this compound are shown below.

$^1$H-NMR (300 MHz, CDCl$_3$); δ=1.28 (s, 9H), 7.25-7.37 (m, 6H), 7.44-7.48 (m, 1H), 7.56-7.65 (m, 4H), 7.71-7.76 (m, 4H).

$^{13}$C-NMR (74 MHz, CDCl$_3$); δ=30.8, 35.0, 120.8, 121.7, 121.7, 124.9, 125.0, 125.2, 126.4, 126.6, 126.6, 128.3, 129.4, 129.7, 129.9, 131.6, 133.0, 133.0, 135.5, 135.7, 138.0, 138.1, 147.8.

Further, a synthesis scheme (e-2) of 9,10-bis(4-bromophenyl)-2-tert-butylanthracene is shown below.

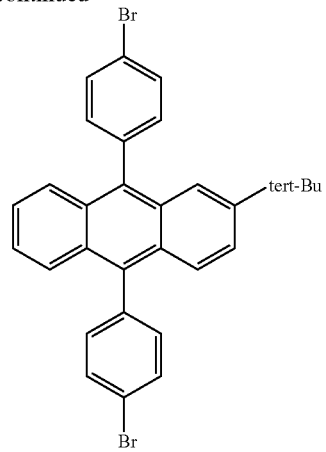

[Step 2: Synthesis of YGABPA]

Under nitrogen, 10 mL of dehydrated toluene was added to a mixture of 540 mg (1.0 mmol) of 9,10-bis(4-bromophenyl)-2-tert-butylanthracene, 670 mg (2.0 mmol) of 9-[4-(N-phenylamino)phenyl]carbazole (abbreviation: YGA), 12 mg (0.02 mmol) of bis(dibenzylideneacetone)palladium (0), 110 mg (0.2 mmol) of tri-tert-butylphosphine, and 600 mg (6.2 μmmol) of sodium-tert-butoxide. This mixture was heated and stirred at 90° C. for five hours under a nitrogen atmosphere. After the reaction, about 100 mL of toluene was added to the reaction mixture, and then the mixture was filtered through Florisil®, alumina and celite. A thus obtained filtrate was condensed and purified by silica gel column chromatography (toluene:hexane=1:1) and then recrystallized by dichloromethane-hexane to obtain 500 mg (the yield: 48%) of a yellow green powder. By using a nuclear magnetic resonance spectrometry ($^1$H-NMR), it was confirmed that this yellow green powder was 9,10-bis(4-{N-[4-(9-carbazolyl)phenyl]-N-phenylamino}phenyl)-2-tert-butylanthracene (abbreviation: YGABPA).

Figure 11A:
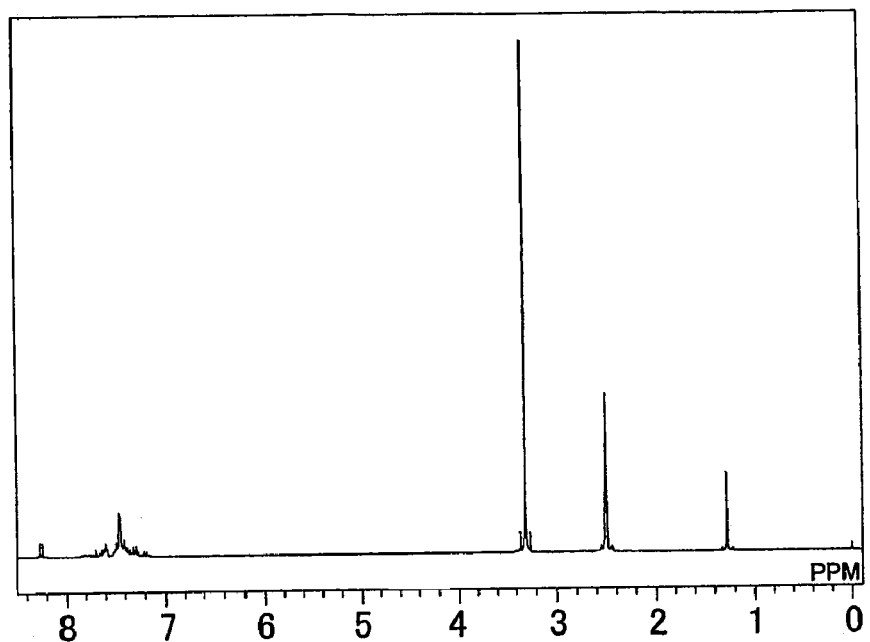
FIGS. 11A and 11B are each a $^1$H-NMR chart of a light emitting element material manufactured in Embodiment 2.
Figure 11B:
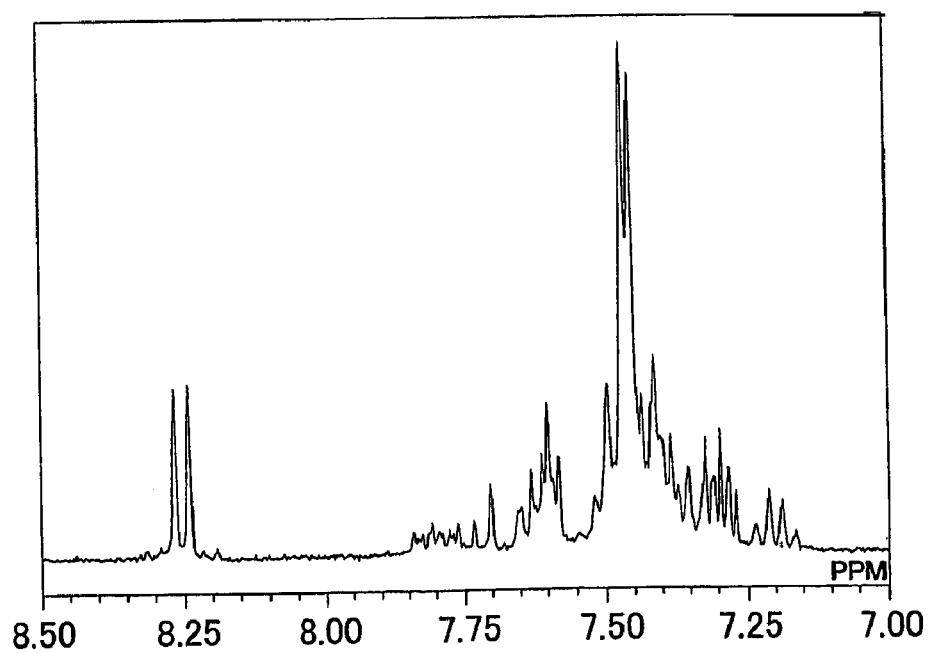

The $^1$H-NMR of the compound is shown below. A $^1$H-NMR chart is also shown in FIGS. 11A and 11B. Further, FIG. 11B is a chart showing an enlarged part in the range of 7 ppm to 8.5 ppm of FIG. 11A.

$^1$H-NMR (300 MHz, DMSO-d$_6$) δ ppm: 8.25 (s, 4H), 7.87-7.16 (m, 35H), and 1.28 (s, 9H).

Further, a synthesis scheme (e-3) of YGABPA is shown below.

(e-3)

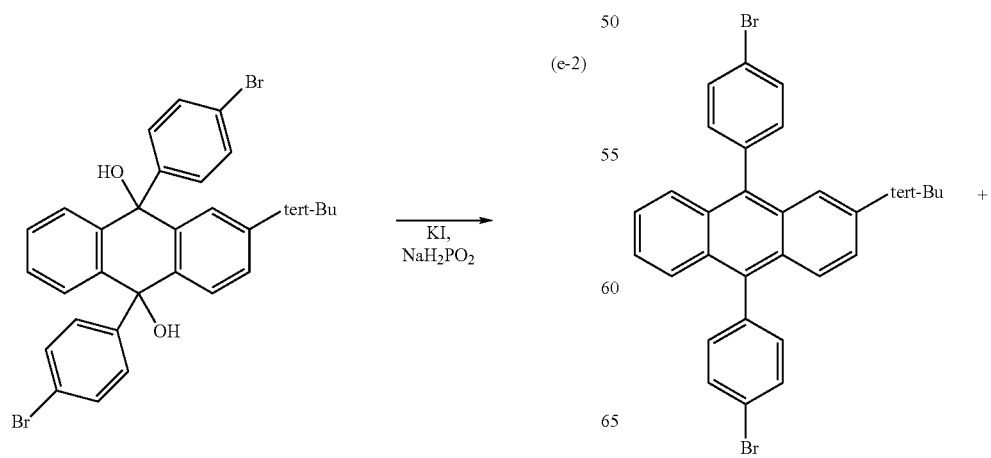

-continued

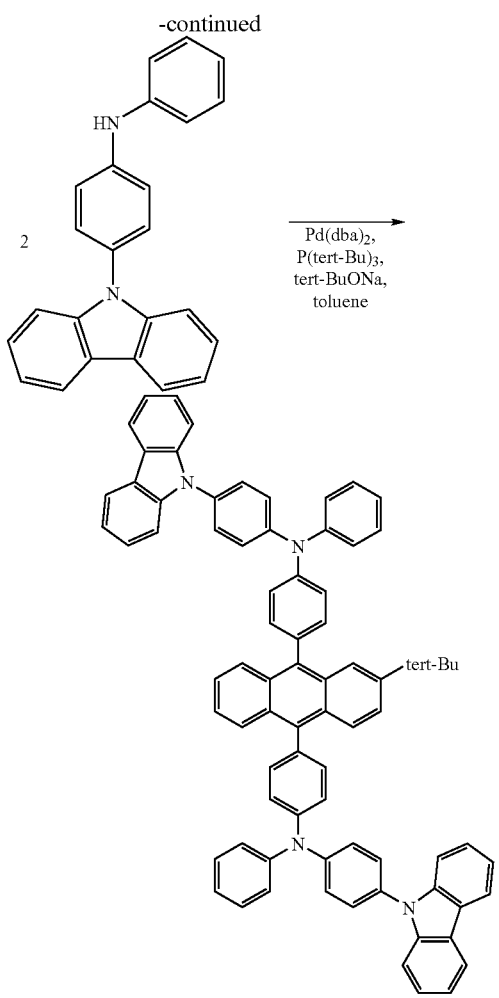

Figure 12:
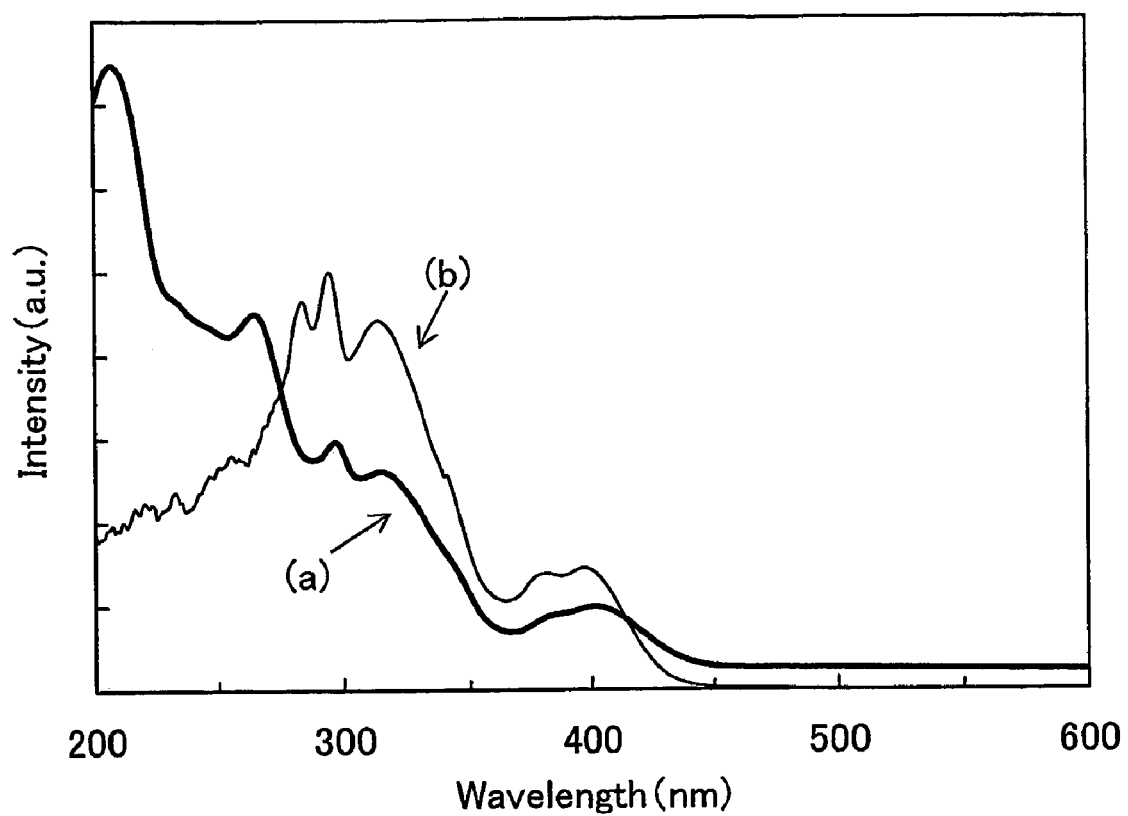
FIG. 12 is an absorption spectrum of a light emitting element material manufactured in Embodiment 2.
Figure 13:
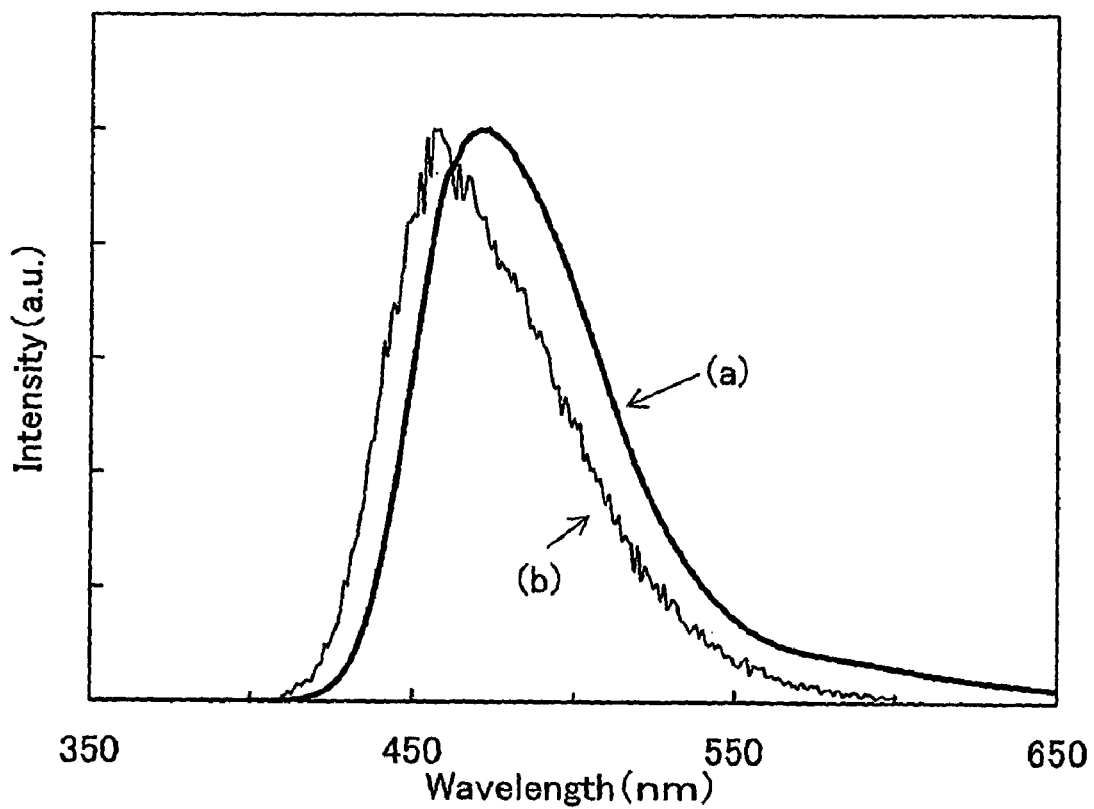
FIG. 13 is a light emission spectrum of a light emitting element material manufactured in Embodiment 2.

The absorption spectrum of the YGABPA is shown in FIG. 12. In FIG. 12, a horizontal axis represents a wavelength (nm) and a vertical axis represents intensity (arbitrary unit). Further, a line (a) indicates the absorption spectrum in a state where the YGABPA is a single film whereas a line (b) indicates the absorption spectrum in a state where the YGABPA is dissolved in a toluene solution. The light emission spectrum of the YGABPA is shown in FIG. 13. In FIG. 13, a horizontal axis represents a wavelength (nm) and a vertical axis represents light emission intensity (arbitrary unit). A line (a) indicates the light emission spectrum (an excited wavelength: 358 nm) in a state where the YGABPA is a single film and a line (b) indicates the light emission spectrum (an excited wavelength: 358 nm) in a state where the YGABPA is dissolved in a toluene solution. It is found from FIG. 13 that light emission from the YGABPA has a peak at 474 nm in the single film state and has a peak at 460 nm in the dissolved state in the toluene solution. Moreover, the light emission is recognized as blue light. Thus, it is found that the YGABPA is suitable as a light emitting substance which exhibits blue light.

When a film was formed with the thus obtained YGABPA by an evaporation method and the ionization potential of the YGABPA in the thin film state was measured by using a photoelectron spectrometer (AC-2, manufactured by RIKEN KEIKI CO., LTD.), the ionization potential was 5.44 eV. The absorption spectrum of the YGABPA in the thin film state was measured by using a UV and visible light spectrophotometer (V-550, manufactured by Japan Spectroscopy Corporation), and a wavelength of an absorption edge at a longer wavelength side of the absorption spectrum was set to be an energy gap (2.86 eV). Under these conditions, when a LUMO level was measured, it was −2.58 eV.

Further, when a decomposition temperature $T_d$ of the thus obtained YGABPA was measured by a thermo-gravimetric/differential thermal analyzer (TG/DTA 320, manufactured by Seiko Instruments Inc.), the $T_d$ was 500° C. or more, and therefore, it was found that the YGABPA has a favorable heat resistant property.

In addition, an oxidation reduction reaction characteristic of the YGABPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF) was used as a solvent. Tetra-n-butylammonium perchlorate (n-$Bu_4NClO_4$), which was a supporting electrolyte, was dissolved in the solvent such that the concentration of the tetra-n-butylammonium perchlorate was 100 mmol/L. Moreover, the YGABPA, which was an object to be measured, was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/$Ag^+$ electrode (an RE5 nonaqueous solvent reference electrode, manufactured by BAS Inc.) was used as a reference electrode.

The oxidation reaction characteristic was measured as follows. After the electric potential of the work electrode with respect to the reference electrode was changed from 0.20 V to 0.80 V, a scan for changing the electric potential from 0.80 V to 0.20 V was set as one cycle, and 100 cycles were measured. Further, the scanning speed of the CV measurement was set to be 0.1 V/s.

The reduction reaction characteristic was measured as follows. After the electric potential of the work electrode with respect to the reference electrode was changed from −0.90 V to −2.60 V, a scan for changing the electric potential from −2.60 V to −0.90 V was set as one cycle, and 100 cycles were measured. Note that, the scanning speed of the CV measurement was set to be 0.1 V/s.

Figure 14A:
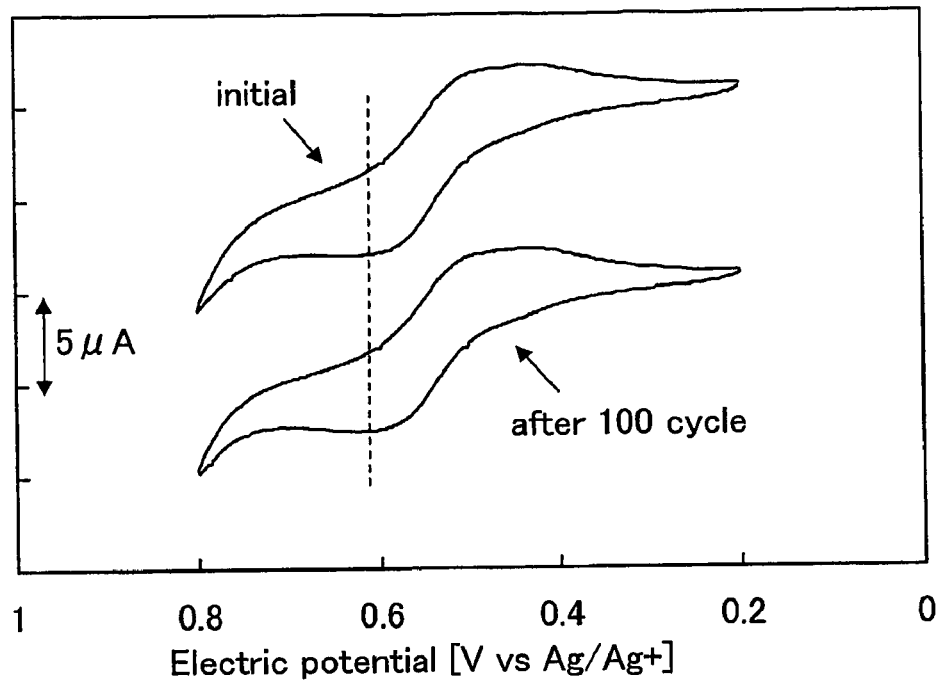
FIGS. 14A and 14B are each a CV measurement result of a light emitting element material manufactured in Embodiment 2.
Figure 14B:
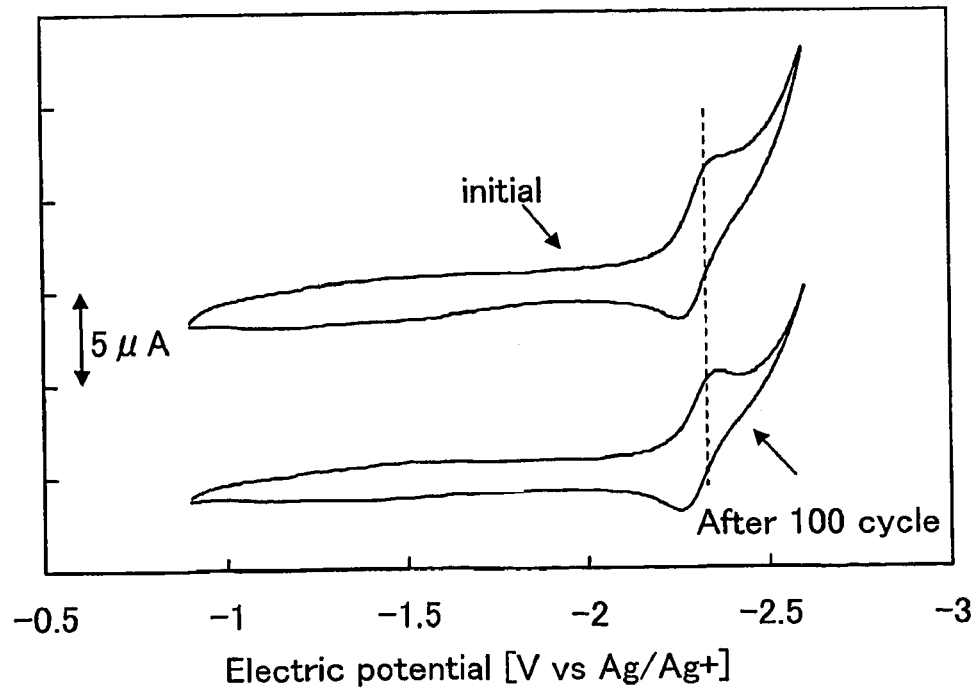

Results of measuring the oxidation reaction characteristic of the YGABPA are shown in FIG. 14A. Moreover, results of measuring the reduction reaction characteristic of the YGABPA are shown in FIG. 14B. In FIGS. 14A and 14B, a horizontal axis represents an electric potential (V) of the work electrode with respect to the reference electrode, while a vertical axis represents the amount of current flowing between the work electrode and the auxiliary electrode ($1×10^{-5}$ A).

It is found from FIG. 14A that an oxidation potential was 0.61 V (vs. Ag/$Ag^+$ electrode). It is found from FIG. 14B that a reduction potential was −2.36 V (vs. Ag/$Ag^+$ electrode). Although the scan was repeated for 100 cycles, a peak position and a peak intensity of a CV curve were hardly changed in each of the oxidation reaction and the reduction reaction. Thus, it was also known that the anthracene derivative of the present invention is extremely stable with respect to the repetition of the oxidation reduction reaction.

EMBODIMENT 3

A synthesis of an anthracene derivative using the carbazole derivative obtained by Embodiment 1 will be described.

[Step 1: Synthesis of 9-phenyl-10-(4-bromophenyl)anthracene (abbreviation: PA)]

(i) Synthesis of 9-phenylanthracene.

5.4 g (21.1 mmol) of 9-bromoanthracene, 2.6 g (21.1 mmol) of phenylboronic acid, 60 mg (0.21 mmol) of Pd(OAc)$_2$ (0), 10 mL (20 mmol) of an K$_2$CO$_3$ aqueous solution of 2M, 263 mg (0.84 mmol) of P(o-tolyl)$_3$, and 20 mL of 1,2-dimethoxyethane (abbreviation: DME) are mixed, and then stirred for 9 hours at 80° C. After reaction, a precipitated solid was collected by suction filtration. Subsequently, the solid was dissolved in toluene and then filtered through Florisil®, celite, and alumina. After a filtrate was washed with water and saturated saline, it was dried with magnesium sulfate. After natural filtration, when the filtrate is condensed, 21.5 g of 9-phenylanthracene which is a target substance was obtained as a light brown solid at a yield of 85% (Synthesis Scheme (f-1)).

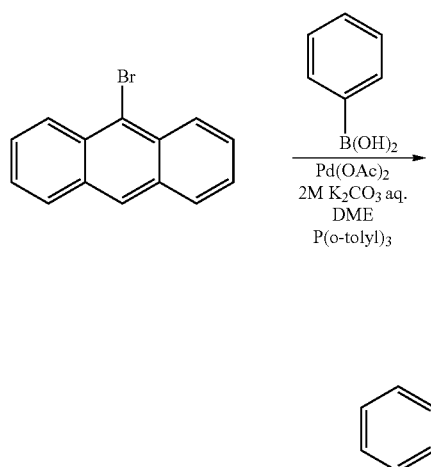

(f-1)

(ii) Synthesis of 9-bromo-10-phenylanthracene.

6.0 g (23.7 mmol) of 9-phenylanthracene was dissolved in 80 mL of carbon tetrachloride, and then in the reaction solution thereof, a solution in which 3.80 g (21.1 mmol) of bromine dissolved in 10 mL of carbon tetrachloride was dropped by a dropping funnel. After dropping, it was stirred for one hour at room temperature. After reaction, a sodium thiosulfate aqueous solution was added to stop the reaction. An organic layer was, washed with a NaOH aqueous solution and saturated saline, and then dried with magnesium sulfate. After natural filtration, a filtrate was condensed and dissolved in toluene, and then filtration was carried out using Florisil®, celite, and alumina. When the filtrate was condensed and then recrystallized with dichloromethane and hexane, 7.0 g of 9-bromo-10-phenylanthracene that is a target substance was obtained as a light yellow solid at a yield of 89% (Synthesis Scheme (f-2)).

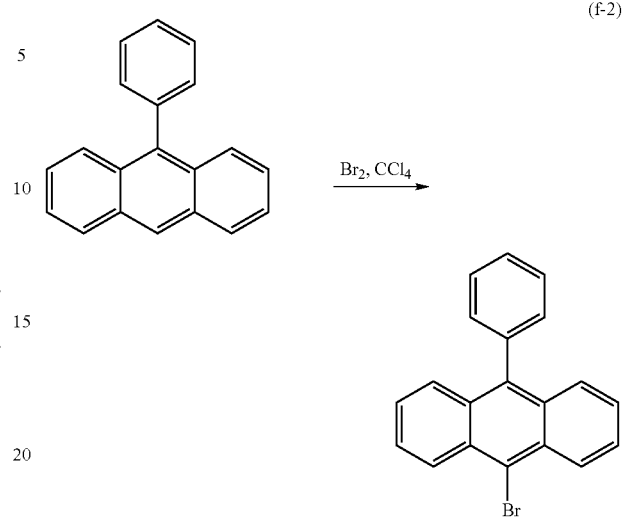

(f-2)

(iii) Synthesis of 9-iodo-10-phenylanthracene.

3.33 g (10 mmol) of 9-bromo-10-phenylanthracene was dissolved in 80 mL of tetrahydrofuran (abbreviation: THF), and cooled to −78° C. Then, in a reaction solution thereof, 7.5 mL (12.0 mmol) of n-BuLi (1.6 M) was dropped by a dropping funnel and then stirred for one hour. A solution in which 5 g (20.0 mmol) of iodine dissolved in 20 mL of THF was dropped therein, and the further stirred for 2 hours at −78° C. After reaction, a sodium thiosulfate aqueous solution was added to stop the reaction. An organic layer was washed with a sodium thiosulfate aqueous solution and saturated saline, and then dried with magnesium sulfate. When a filtrate was condensed after natural filtration and then recrystallized with ethanol, 3.1 g of 9-iodo-10-phenylanthracene that is a target substance was obtained as a light yellow solid at a yield of 83% (Synthesis Scheme (f-3)).

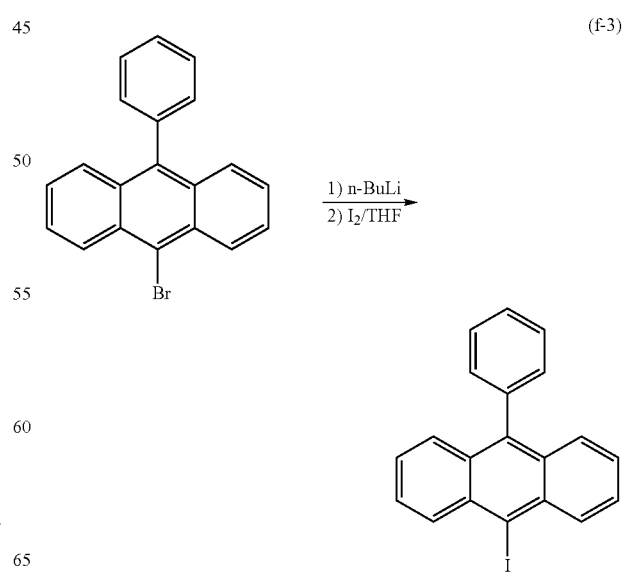

(f-3)

(iv) Synthesis of 9-phenyl-10-(4-bromophenyl)anthracene (abbreviation: PA).

A mixture of 1.0 g (2.63 mmol) of 9-iodo-10-phenylanthracene, 542 mg (2.70 mmol) of p-bromo phenylboronic acid, 46 mg (0.03 mmol) of Pd(PPh$_3$)$_4$ (O), 3 mL (6 mmol) of K$_2$CO$_3$ of 2M, and 10 mL of toluene was stirred for 9 hours at 80° C. After reaction, toluene was added and filtration was carried out using Florisil®, celite, and alumina. A filtrate was washed with water and saturated saline, and then dried with magnesium sulfate. After natural filtration, the filtrate was condensed, and when it was recrystallized with chloroform and hexane, 562 mg of 9-phenyl-10-(4-bromophenyl)anthracene that is a target substance is obtained as a light brown solid at a yield of 45% (Synthesis Scheme (f-4)).

[Step 2: Synthesis of YGAPA]

A mixture of 409 mg (1.0 mmol) of 9-phenyl-10-(4-bromophenyl)anthracene, 339 g (1.0 mmol) of YGA, 6 mg (0.01 mmol) of Pd (dba)$_2$ (0), 500 mg (5.2 mol) of tert-BuONa, 0.1 mL of P(tert-Bu)$_3$, and 10 mL of toluene were stirred for 4 hours at 80° C. After reaction, a solution was washed with water, an aqueous layer was extracted with toluene, and it was washed together with the organic layer using saturated saline, and then dried with magnesium sulfate. An oily product obtained by natural filtration and condensation was purified with silica gel column chromatography (hexane: toluene=7: 3), and recrystallized using dichloromethane and hexane to obtain 534 mg of YGAPA as a yellow powder-like solid that is a target substance at a yield of 81% (Synthesis Scheme (f-5)). When this compound was measured by a nuclear magnetic resonance spectrometry ($^1$H-NMR), it was confirmed that the compound was 9-(4-{N-[4-(9-carbazolyl)phenyl]-N-phenylamino}phenyl)-10-phenylanthracene.

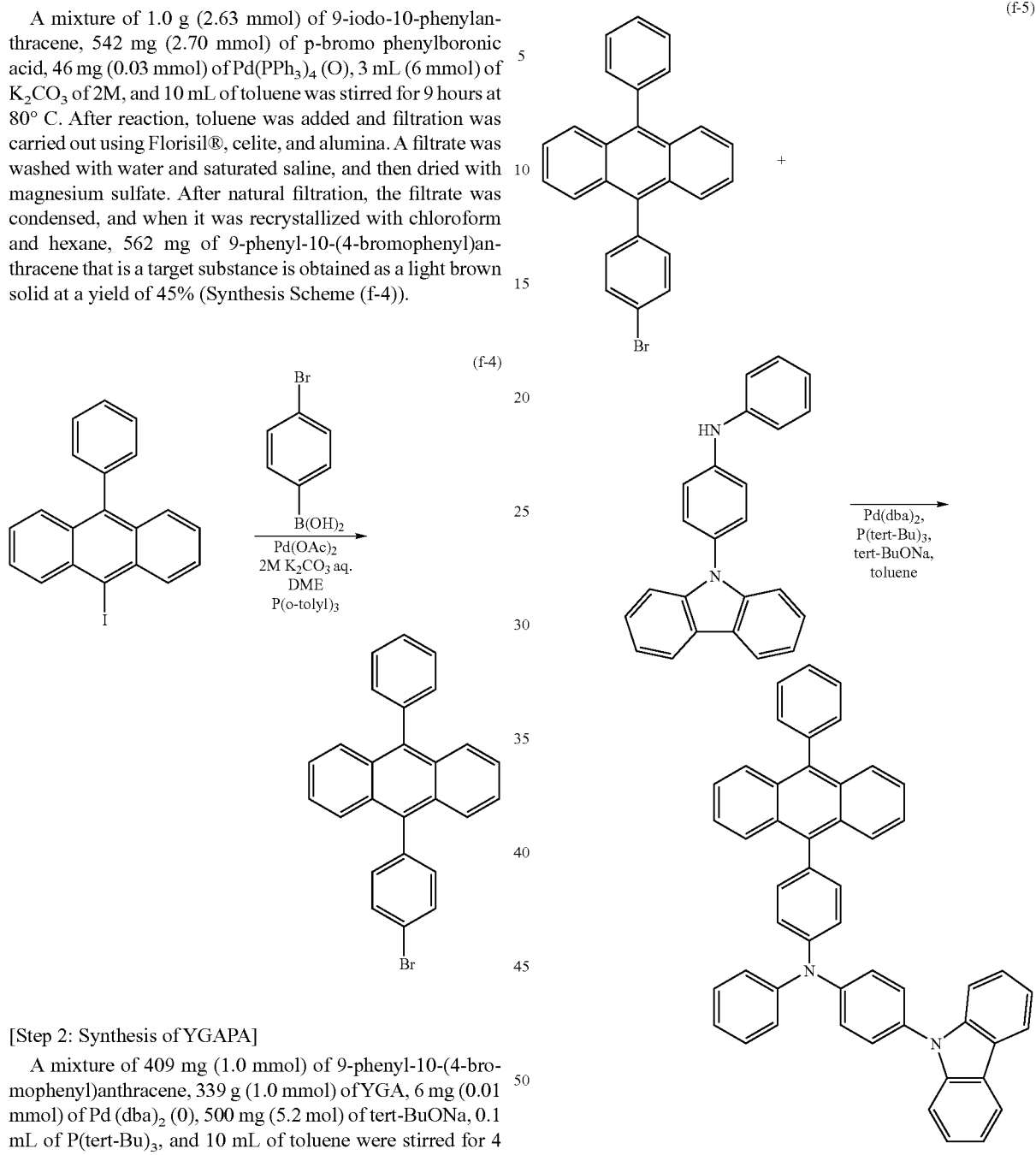

Figure 15A:
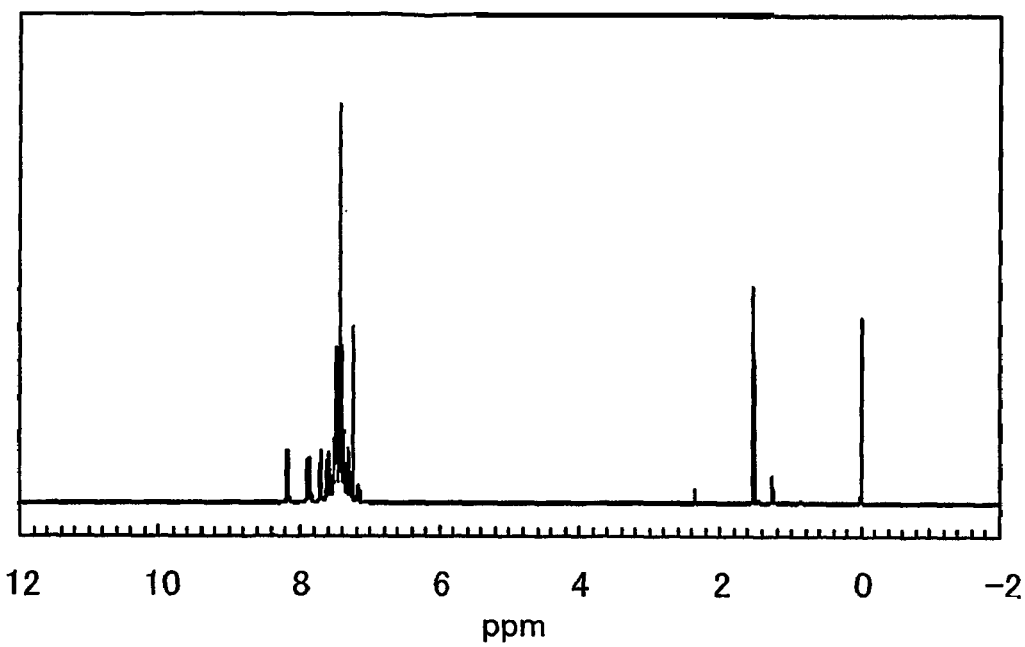
FIGS. 15A and 15B are each a $^1$H-NMR chart of a light emitting element material manufactured in Embodiment 3.
Figure 15B:
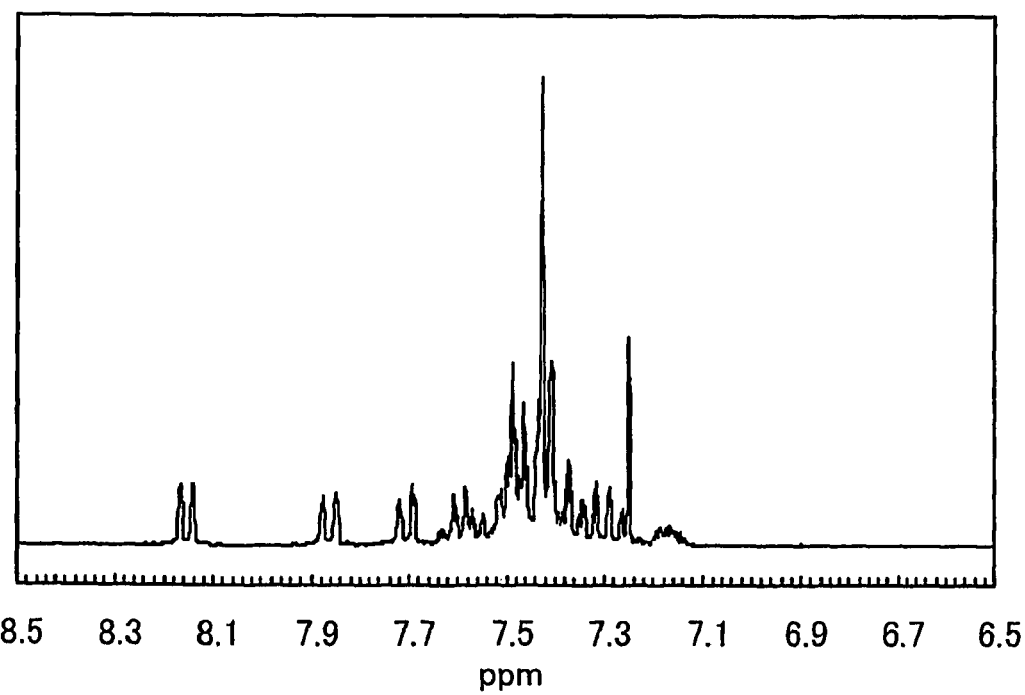

The $^1$H-NMR of the compound is shown below. A $^1$H-NMR chart is also shown in FIGS. 15A and 15B. Further, FIG. 15B is a chart showing an enlarged part in the range of 6.5 ppm to 8.5 ppm of FIG. 15A.

$^1$H-NMR (300 MHz, DMSO-d$_6$); δ=7.22-7.30 (m, 4H), 7.39-7.47 (m, 21H), 7.58-7.68 (m, 7H), 7.78 (d, J=8.1 Hz, 2H), 8.26 (d, J=7.2 Hz, 2H).

Figure 17:
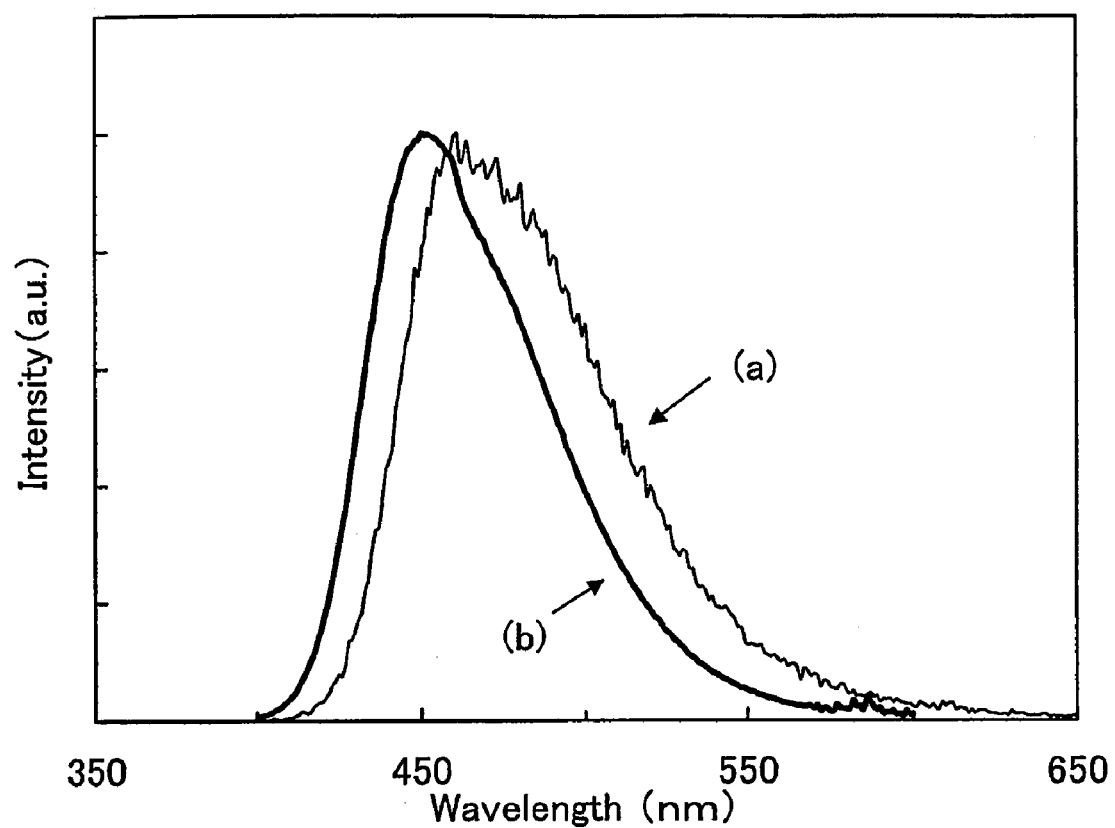
FIG. 17 is a light emission spectrum of a light emitting element material manufactured in Embodiment 3.

The absorption spectrum of the YGAPA is shown in FIG. 16. In FIG. 16, a horizontal axis represents a wavelength (nm) and a vertical axis represents intensity (arbitrary unit). Further, in FIG. 16, a line (a) indicates the absorption spectrum in a state where the YGAPA is a single film whereas a line (b) indicates the absorption spectrum in a state where the YGAPA is dissolved in a toluene solution. The light emission spectrum of, the YGAPA is shown in FIG. 17. In FIG. 17, a horizontal axis represents a wavelength (nm) and a vertical axis represents light emission intensity (arbitrary unit). A line (a) indicates the light emission spectrum (an excited wavelength: 390 nm) in a state where the YGAPA is a single film and a line (b) indicates the light emission spectrum (an excited wavelength: 370 nm) in a state where the YGAPA is dissolved in a toluene solution. It is apparent from FIG. 17 that light emission from the YGAPA has a peak at 461 nm in the single film state and has a peak at 454 nm in the dissolved state in the toluene solution. Moreover, the light emission was recognized as blue light. Thus, it is found that the YGAPA is suitable as a light emitting substance which exhibits blue light.

When a film was formed with the thus obtained YGAPA by an evaporation method and the ionization potential of the YGAPA in the thin film state was measured by using a photoelectron spectrometer (AC-2, manufactured by RIKEN KEIKI CO., LTD.), the ionization potential was 5.55 eV. The absorption spectrum of the YGAPA in the thin film state was measured by using a UV and visible light spectrophotometer (V-550, manufactured by Japan Spectroscopy Corporation), and a wavelength of an absorption edge at a longer wavelength side of the absorption spectrum was set to be an energy gap (2.95 eV). Under these conditions, when the LUMO level was measured, it was −2.60 eV.

Further, when a decomposition temperature $T_d$ of the thus obtained YGAPA was measured by a thermo-gravimetric/differential thermal analyzer (TG/DTA 320, manufactured by Seiko Instruments Inc.), the $T_d$ was 402° C. or more, and therefore, it was understood that the YGAPA has a favorable heat resistant property.

In addition, an oxidation reduction reaction characteristic of the YGAPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF) was used as a solvent. Tetra-n-butylammonium perchlorate (n-Bu$_4$NClO$_4$), which was a supporting electrolyte, was dissolved in the solvent such that the concentration of the tetra-n-butylammonium perchlorate was 100 mmol/L. Moreover, the YGAPA, which was an object to be measured, was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode.

The oxidation reaction characteristic was measured as follows. After the electric potential of the work electrode with respect to the reference electrode was changed from −0.35 V to 0.75 V, a scan for changing the electric potential from 0.75 V to −0.35 V was set as one cycle, and 100 cycles were measured. Further, the scanning speed of the CV measurement was set to be 0.1 V/s.

The reduction reaction characteristic was measured as follows. After the electric potential of the work electrode with respect to the reference electrode was changed from −0.55 V to −2.4 V, a scan for changing the electric potential from −2.4 V to −0.05 V was set as one cycle, and 100 cycles were measured. Note that, the scanning speed of the CV measurement was set to be 0.1 V/s.

Figure 18A:
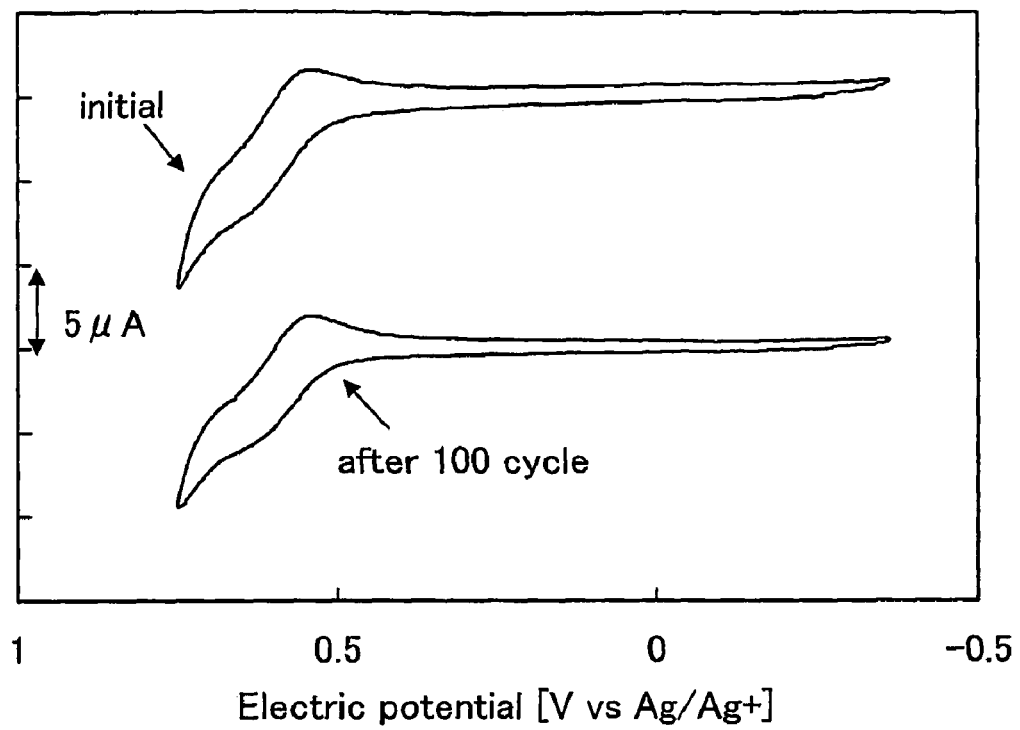
FIGS. 18A and 18B are each a CV measurement result of a light emitting element material manufactured in Embodiment 3.
Figure 18B:
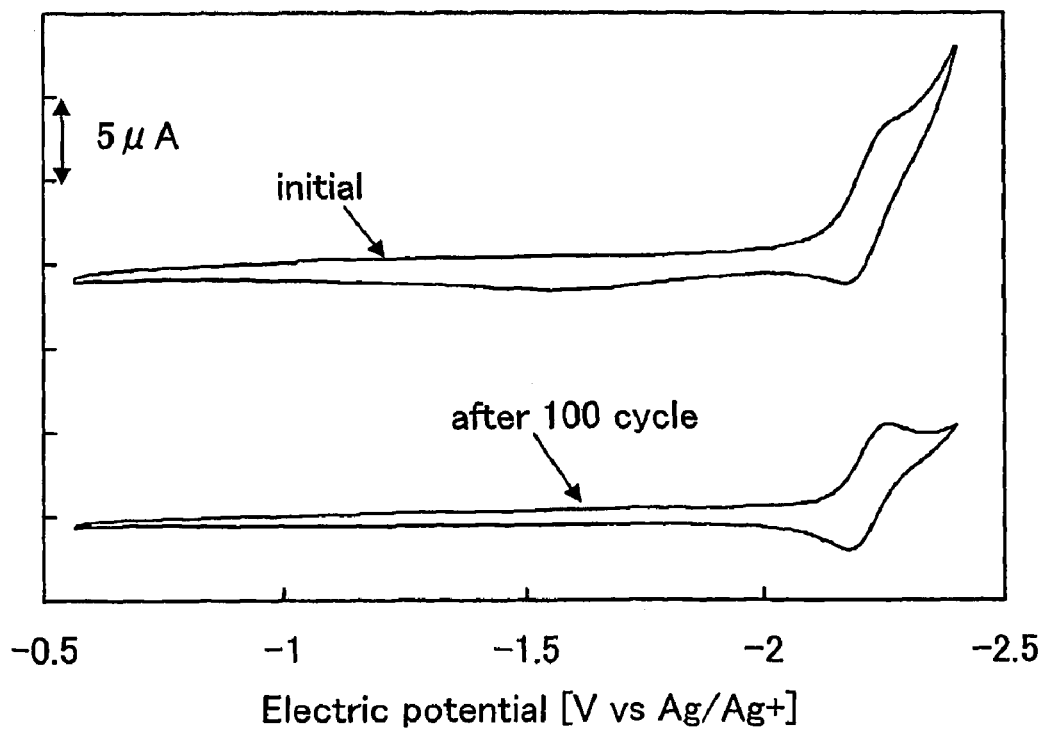

Results of measuring the oxidation reaction characteristic of the YGAPA are shown in FIG. 18A. Moreover, results of measuring the reduction reaction characteristic of the YGAPA are shown in FIG. 18B. In FIGS. 18A and 18B, a horizontal axis represents an electric potential (V) of the work electrode with respect to the reference electrode, while a vertical axis represents the amount of current flowing between the work electrode and the auxiliary electrode ($1 \times 10^{-5}$ A).

It is found from FIG. 18A that an oxidation potential was 0.6 V (vs. Ag/Ag$^+$ electrode). It is found from FIG. 18B that a reduction potential was −2.29 V (vs. Ag/Ag$^+$ electrode). Although the scan was repeated for 100 cycles, a peak of a CV curve was clearly observed in each of the oxidation reaction and the reduction reaction. Thus, it was found that an anthracene derivative of the present invention is a substance showing favorable reversibility with respect to an oxidation reduction reaction, and particularly shows excellent reversibility with respect to an oxidation reaction because it contains a carbazole derivative of the present invention. In other words, it was found that the anthracene derivative of the present invention has resistance to repetition of an oxidation reaction, and that a change in the substance does not occur easily.

EMBODIMENT 4

A method for manufacturing a light emitting element that uses the YGABPA synthesized in Embodiment 2 as a light emitting substance and an operational characteristic of the light emitting element will be described in this embodiment.

Figure 19:
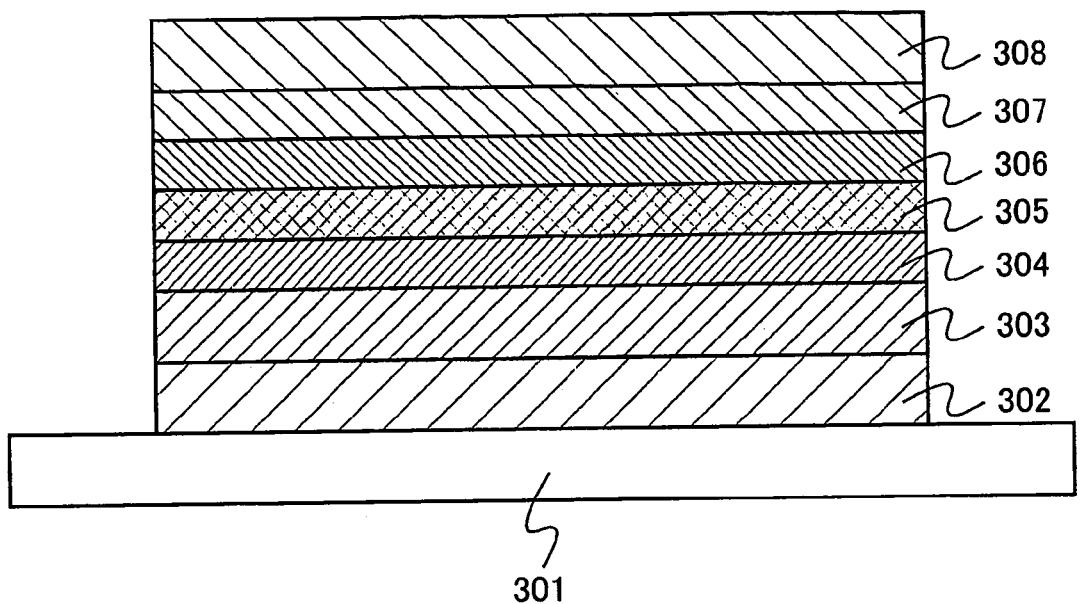
FIG. 19 is a view describing a light emitting element manufactured in embodiments.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

Subsequently, the inside of the vacuum evaporation apparatus was evacuated so that the pressure was reduced to $10^{-4}$ Pa. Then, a first layer 303 including copper phthalocyanine was formed over the first electrode 302 by an evaporation method. A thickness of the first layer 303 was set to be 20 nm. The first layer 303 serves as a hole injecting layer when operating the light emitting element.

Subsequently, a second layer 304 including NPB was formed over the first layer 303 by an evaporation method. A thickness of the second layer 304 was set to be 40 nm. The second layer 304 serves as a hole transporting layer when operating the light emitting element.

A third layer 305 containing t-BuDNA and YGABPA was formed over the second layer 304 by a co-evaporation method. A thickness of the third layer 305 was set to be 40 nm. The t-BuDNA-YGABPA mass ratio was adjusted to be 1:0.05. Thus, the YGABPA was in such a state of being dispersed in a layer including t-BuDNA. The third layer 305 serves as a light emitting layer when operating the light emitting element. Further, the YGABPA serves as a light emitting substance.

Next, a fourth layer 306 including Alq$_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 20:
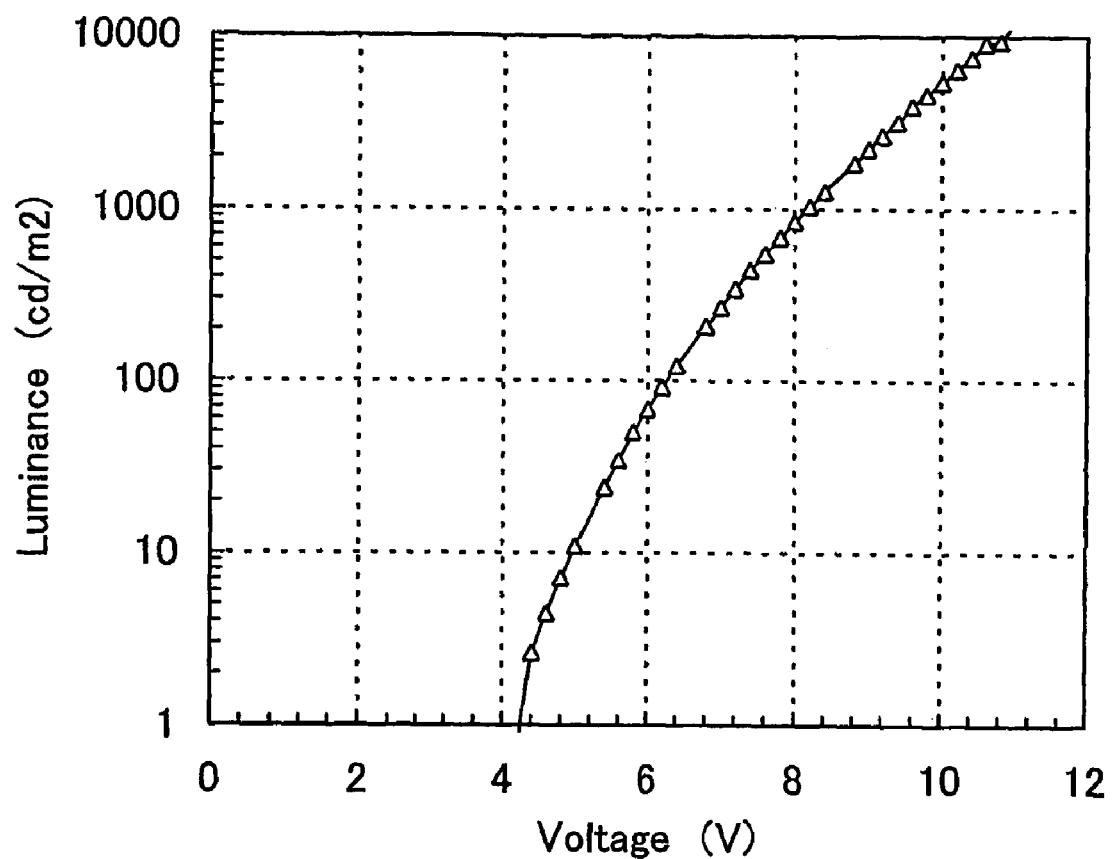
FIG. 20 is a voltage-luminance characteristic of a light emitting element manufactured in Embodiment 4.
Figure 21:
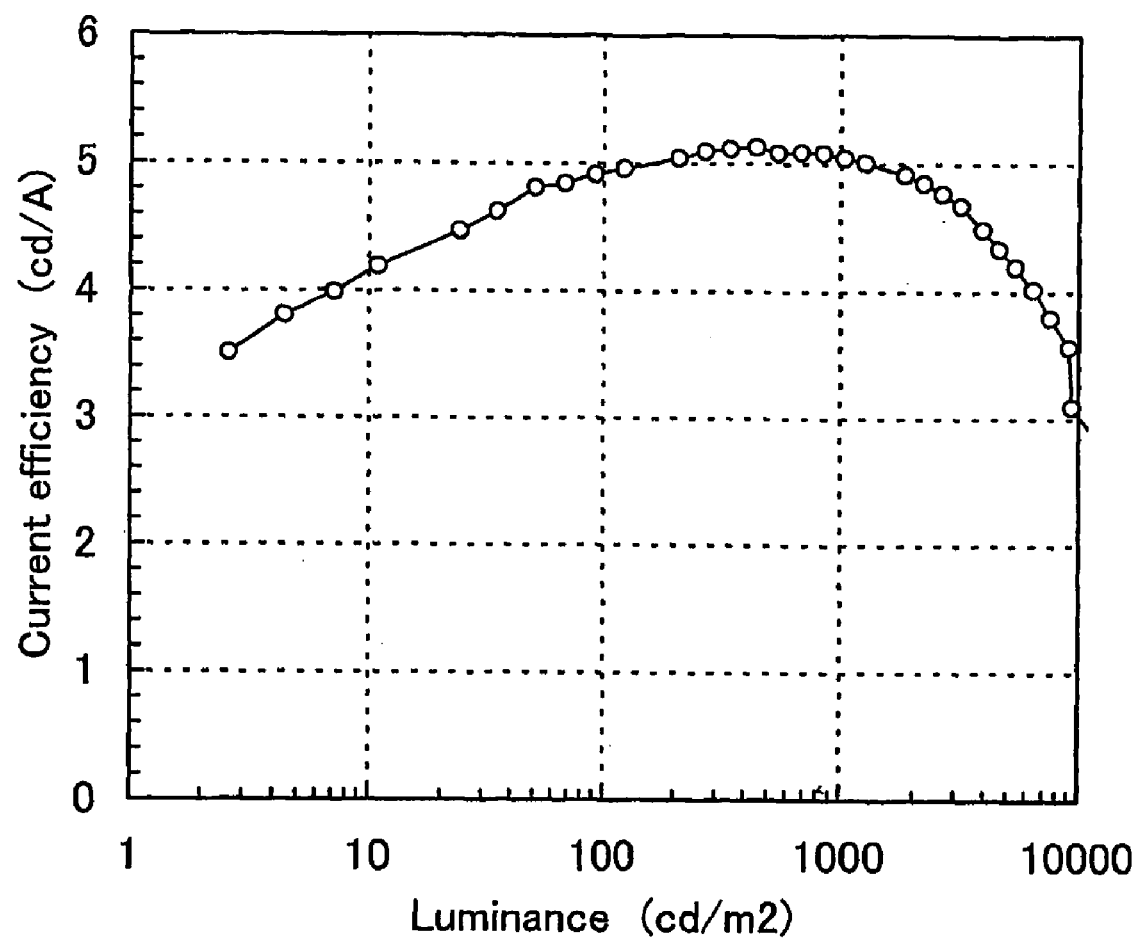
FIG. 21 is a luminance-current efficiency characteristic of a light emitting element manufactured in Embodiment 4.

Measurement results are shown in FIG. 20 and FIG. 21. FIG. 20 shows a measurement result of a voltage-luminance characteristic whereas FIG. 21 shows a measurement result of a luminance-current efficiency characteristic. In FIG. 20, a horizontal axis represents the voltage (V) and a vertical axis represents the luminance ($cd/m^2$). In FIG. 21, a horizontal axis represents the luminance ($cd/m^2$) and a vertical axis represents the current efficiency (cd/A).

Figure 22:
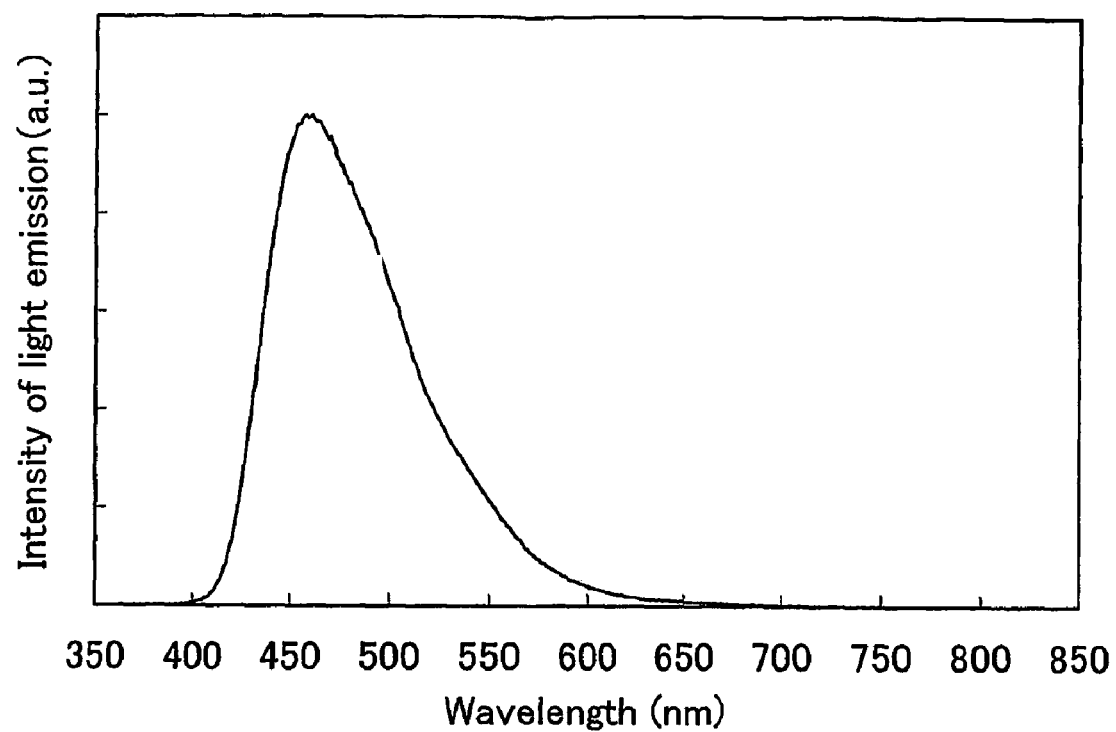
FIG. 22 is a light emission spectrum of a light emitting element manufactured in Embodiment 4.

A light emission spectrum of the light emitting element manufactured in this embodiment is shown in FIG. 22. In FIG. 22, a horizontal axis represents a wavelength (nm) and a vertical axis represents intensity (arbitrary unit). According to FIG. 22, it was found that the light emitting element of this embodiment has a peak of light emission spectrum at 462 nm and exhibits blue light. Moreover, the CIE chromaticity coordinates were x=0.16, y=0.20. Consequently, it was found that the light emitting element of this embodiment exhibits blue light with good color purity.

EMBODIMENT 5

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

Subsequently, the inside of the vacuum evaporation apparatus was evacuated so that the pressure was reduced to $10^{-4}$ Pa. Then, a first layer 303 including copper phthalocyanine was formed over the first electrode 302 by an evaporation method. A thickness of the first layer 303 was set to be 20 nm. The first layer 303 serves as a hole injecting layer when operating the light emitting element.

Subsequently, a second layer 304 including 4,4'-bis[N-(4-biphenylyl)-N-phenylamino]biphenyl (abbreviation: BBPB) was formed over the first layer 303 by an evaporation method. A thickness of the second layer 304 was set to be 40 nm. The second layer 304 serves as a hole transporting layer when operating the light emitting element.

A third layer 305 containing t-BuDNA and YGABPA was formed over the second layer 304 by a co-evaporation method. A thickness of the third layer 305 was set to be 40 nm. The t-BuDNA-YGABPA mass ratio was adjusted to be 1:0.05. Thus, the YGABPA was in such a state of being dispersed in a layer including t-BuDNA. The third layer 305 serves as a light emitting layer when operating the light emitting element. Further, the YGABPA serves as a light emitting substance.

Next, a fourth layer 306 including $Alq_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 23:
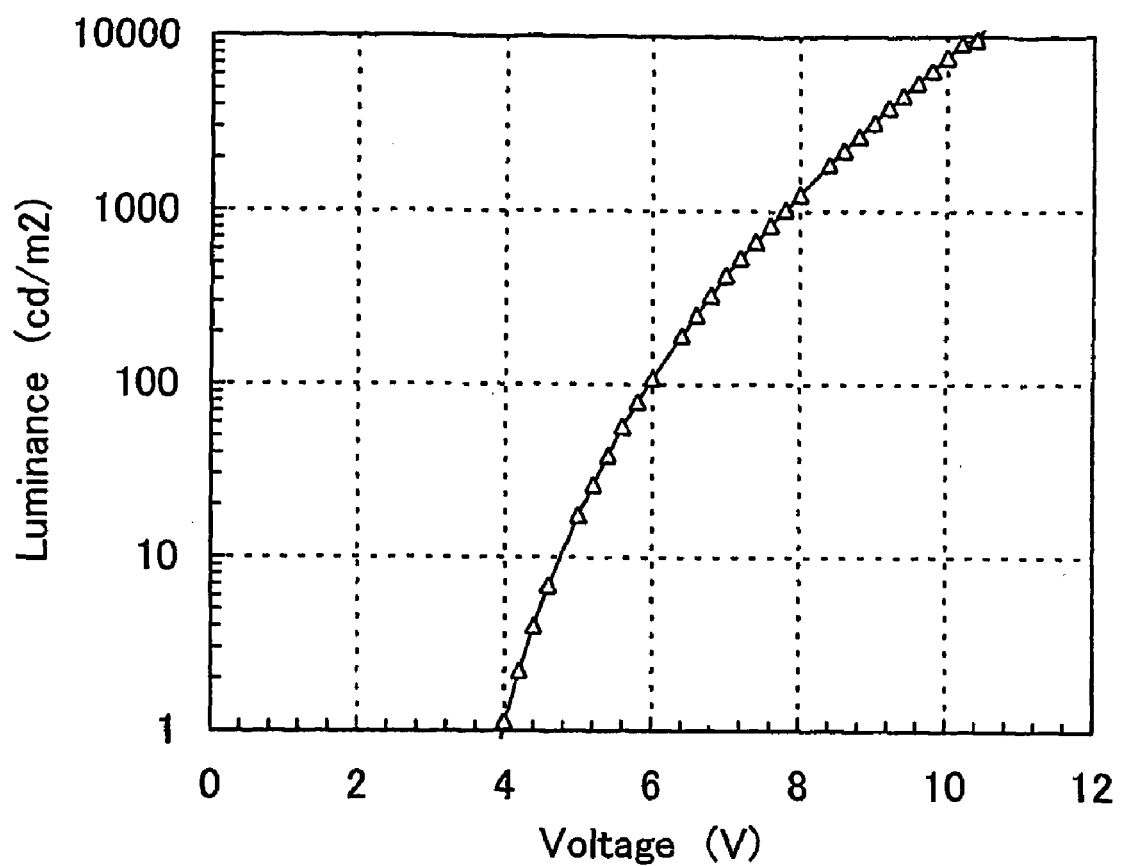
FIG. 23 is a voltage-luminance characteristic of a light emitting element manufactured in Embodiment 5.
Figure 24:
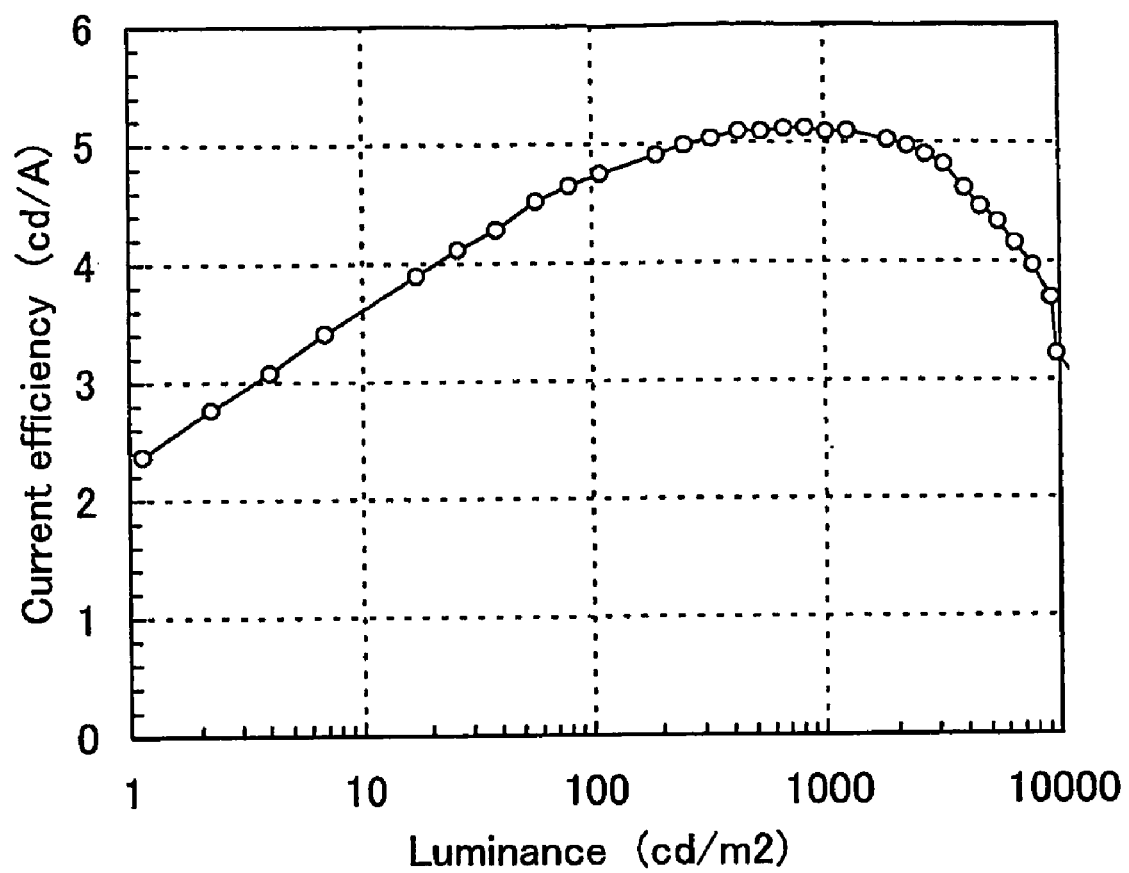
FIG. 24 is a luminance-current efficiency characteristic of a light emitting element manufactured in Embodiment 5.

Measurement results are shown in FIG. 23 and FIG. 24. FIG. 23 shows a measurement result of a voltage-luminance characteristic whereas FIG. 24 shows a measurement result of a luminance-current efficiency characteristic. In FIG. 23, a horizontal axis represents the voltage (V) and a vertical axis represents the luminance ($cd/m^2$). In FIG. 24, a horizontal axis represents the luminance ($cd/m^2$) and a vertical axis represents the current efficiency (cd/A).

Figure 25:
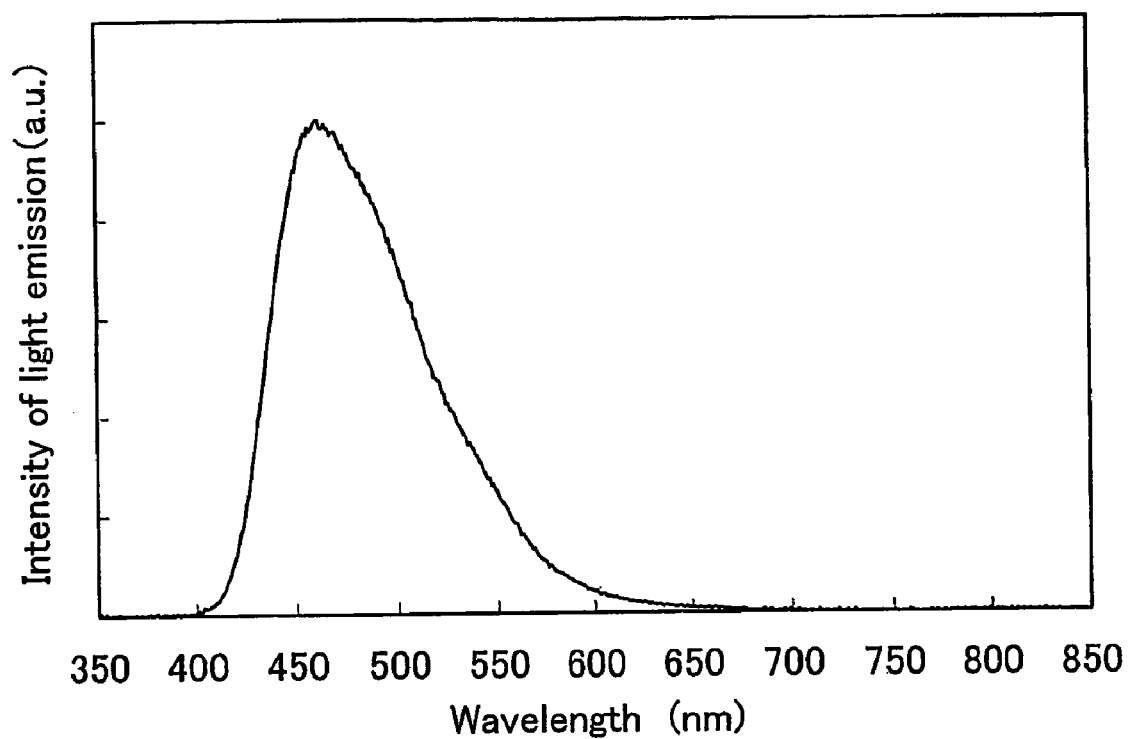
FIG. 25 is a light emission spectrum of a light emitting element manufactured in Embodiment 5.

A light emission spectrum of the light emitting element manufactured in this embodiment is shown in FIG. 25. In FIG. 25, a horizontal axis represents a wavelength (nm) and a vertical axis represents intensity (arbitrary unit). According to FIG. 25, it is found that the light emitting element of this embodiment has a peak of light emission spectrum at 465 nm and exhibits blue light. Moreover, the CIE chromaticity coordinates were x=0.16, y=0.22. Consequently, it was found that the light emitting element of this embodiment exhibits blue light with good color purity.

EMBODIMENT 6

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 including DNTPD was formed over the first electrode 302 by an evaporation method. A thickness of the first layer 303 was set to be 50 nm. The first layer 303 serves as a hole injecting layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing t-BuDNA and YGABPA was formed over the second layer 304 by a co-evaporation method. A thickness of the third layer 305 was set to be 40 nm. The t-BuDNA-YGABPA mass ratio was adjusted to be 1:0.1. Thus, the YGABPA was in such a state of being dispersed in a layer including t-BuDNA. The third layer 305 serves as a light emitting layer when operating the light emitting element. Further, the YGABPA serves as a light emitting substance.

Next, a fourth layer 306 including $Alq_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 26:
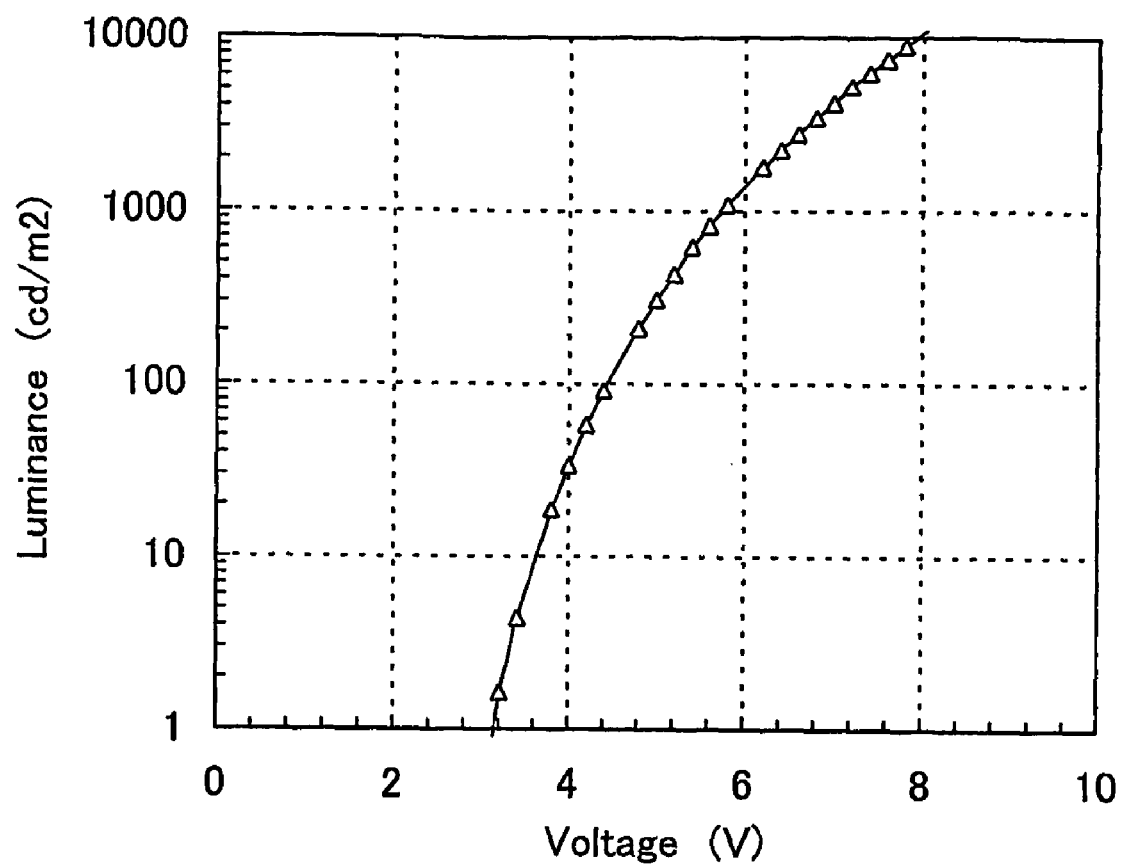
FIG. 26 is a voltage-luminance characteristic of a light emitting element manufactured in Embodiment 6.
Figure 27:
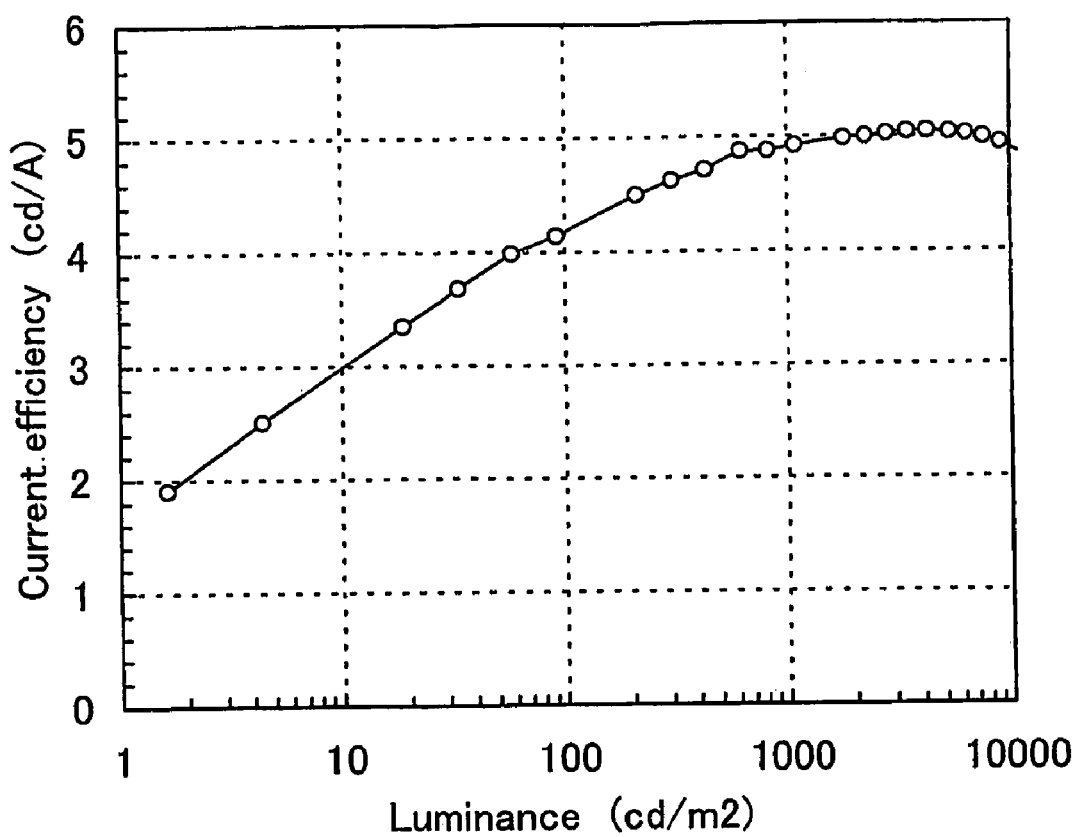
FIG. 27 is a luminance-current efficiency characteristic of a light emitting element manufactured in Embodiment 6.

Measurement results are shown in FIG. 26 and FIG. 27. FIG. 26 shows a measurement result of a voltage-luminance characteristic whereas FIG. 27 shows a measurement result of a luminance-current efficiency characteristic. In FIG. 26, a horizontal axis represents the voltage (V) and a vertical axis represents the luminance ($cd/m^2$). In FIG. 27, a horizontal axis represents the luminance ($cd/m^2$) and a vertical axis represents the current efficiency (cd/A).

Figure 28:
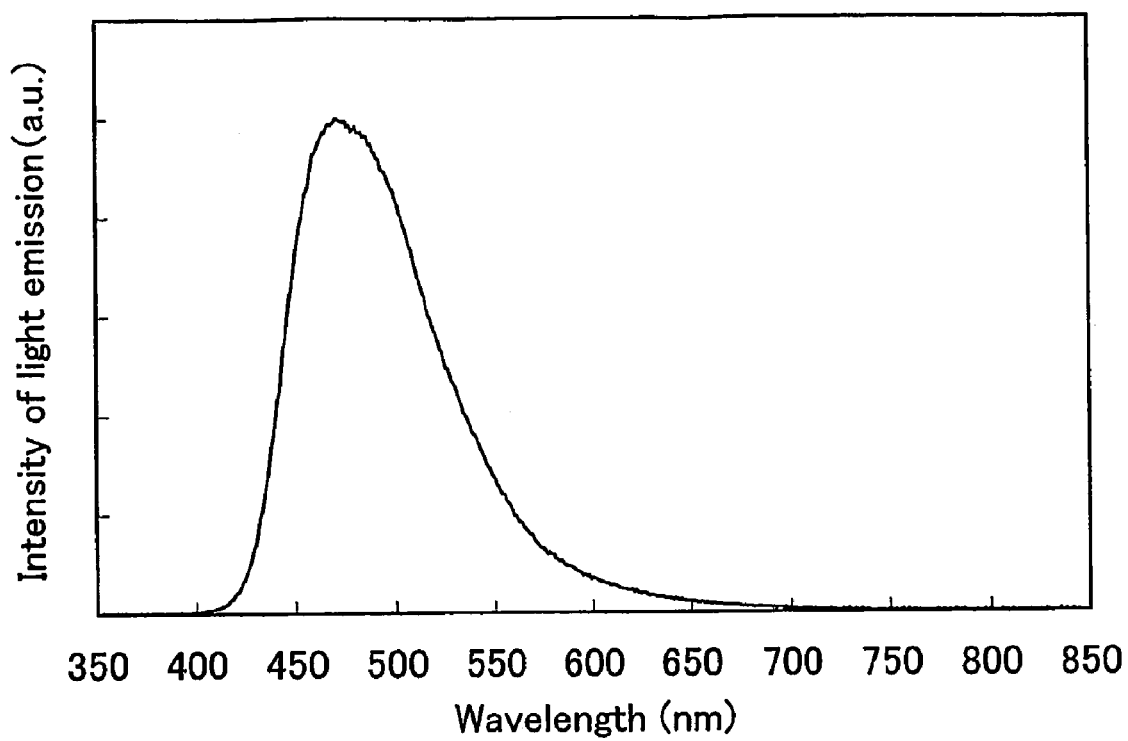
FIG. 28 is a light emission spectrum of a light emitting element manufactured in Embodiment 6.

A light emission spectrum of the light emitting element manufactured in this embodiment is shown in FIG. 28. In FIG. 28, a horizontal axis represents a wavelength (nm) and a vertical axis represents intensity (arbitrary unit). According to FIG. 28, it is found that the light emitting element of this embodiment has a peak of light emission spectrum at 475 nm and exhibits blue light. Moreover, the CIE chromaticity coordinates were x=0.18, y=0.27. Consequently, it was found that the light emitting element of this embodiment exhibits blue light with good color purity.

EMBODIMENT 7

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 containing NPB and molybdenum oxide was formed over the first electrode 302 by a co-evaporation method. A thickness of the first layer 303 was set to be 50 nm. The NPB-molybdenum oxide mass ratio was adjusted to be 4:2. It is to be noted that molybdenum trioxide was particularly used as an evaporation material. The first layer 303 serves as a hole generating layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing t-BuDNA and YGABPA was formed over the second layer 304 by a co-evaporation method. A thickness of the third layer 305 was set to be 40 nm. The t-BuDNA-YGABPA mass ratio was adjusted to be 1:0.1. Thus, the YGABPA was in such a state of being dispersed in a layer including t-BuDNA. The third layer 305 serves as a light emitting layer when operating the light emitting element. Further, the YGABPA serves as a light emitting substance.

Next, a fourth layer 306 including Alq$_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 29:
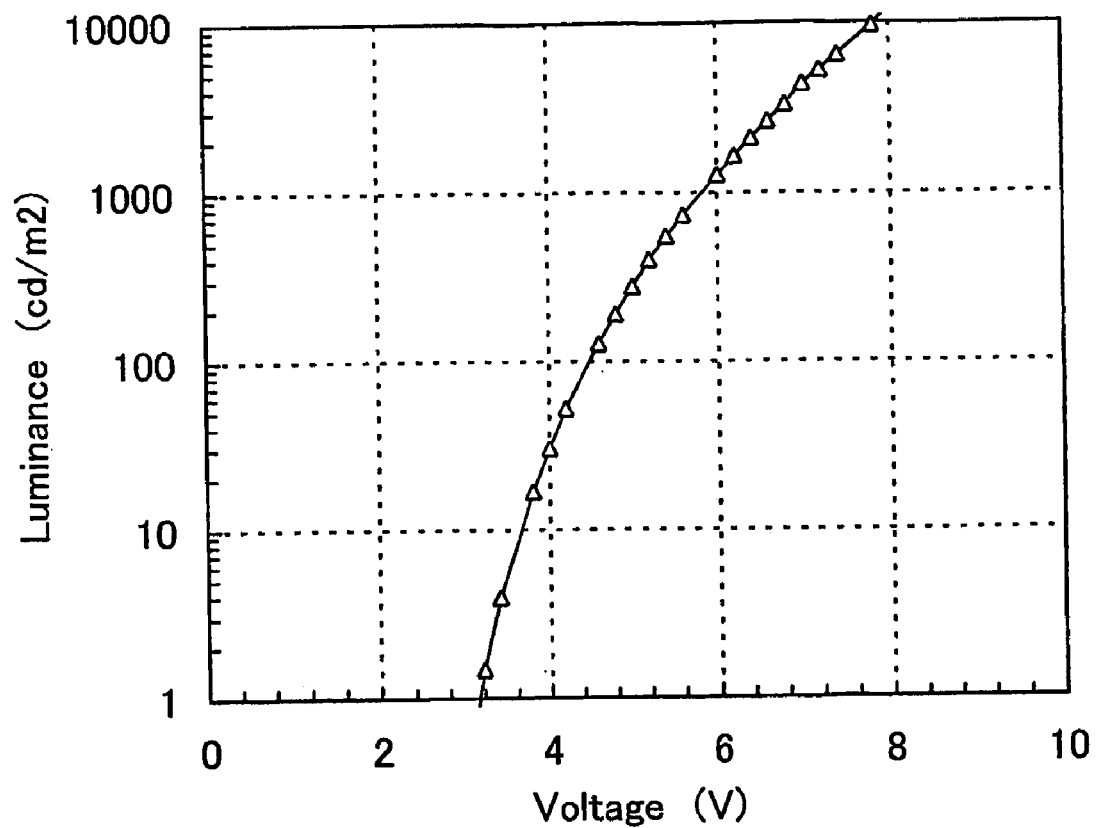
FIG. 29 is a voltage-luminance characteristic of a light emitting element manufactured in Embodiment 7.
Figure 30:
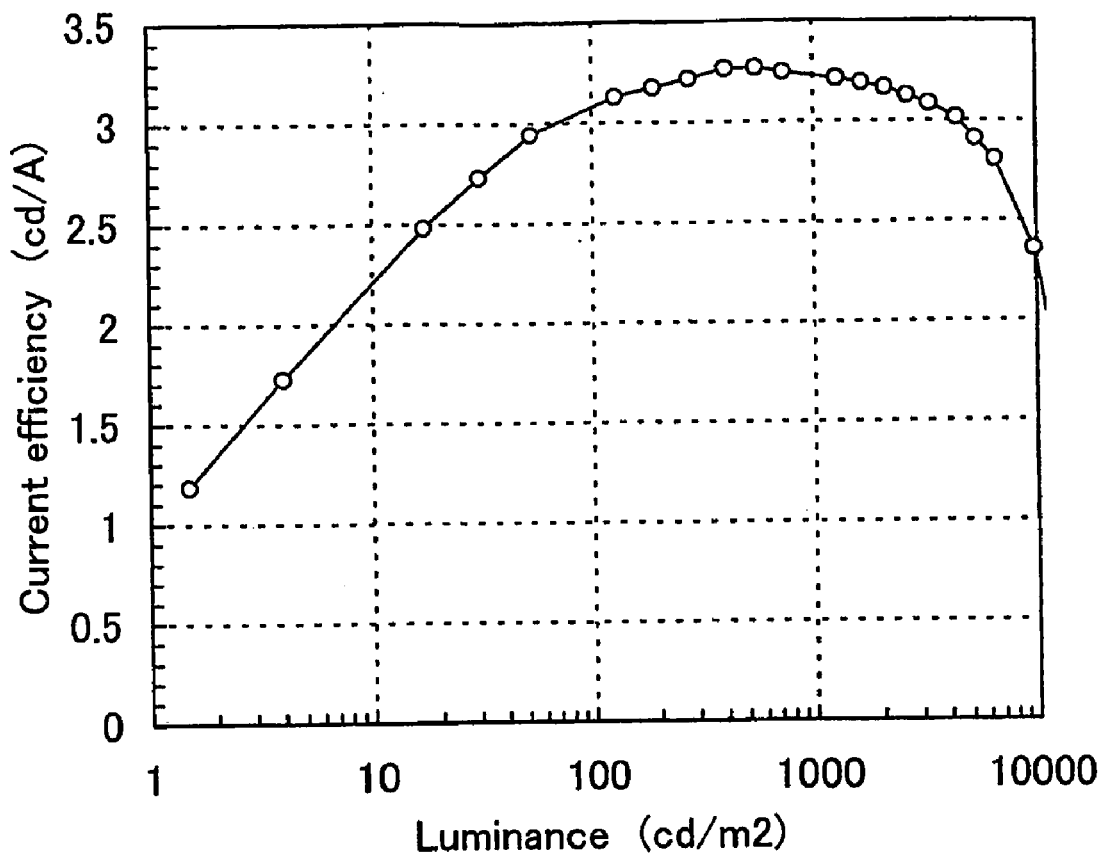
FIG. 30 is a luminance-current efficiency characteristic of a light emitting element manufactured in Embodiment 7.

Measurement results are shown in FIG. 29 and FIG. 30. FIG. 29 shows a measurement result of a voltage-luminance characteristic whereas FIG. 30 shows a measurement result of a luminance-current efficiency characteristic. In FIG. 29, a horizontal axis represents the voltage (V) and a vertical axis represents the luminance (cd/m$^2$). In FIG. 30, a horizontal axis represents the luminance (cd/m$^2$) and a vertical axis represents the current efficiency (cd/A).

Figure 31:
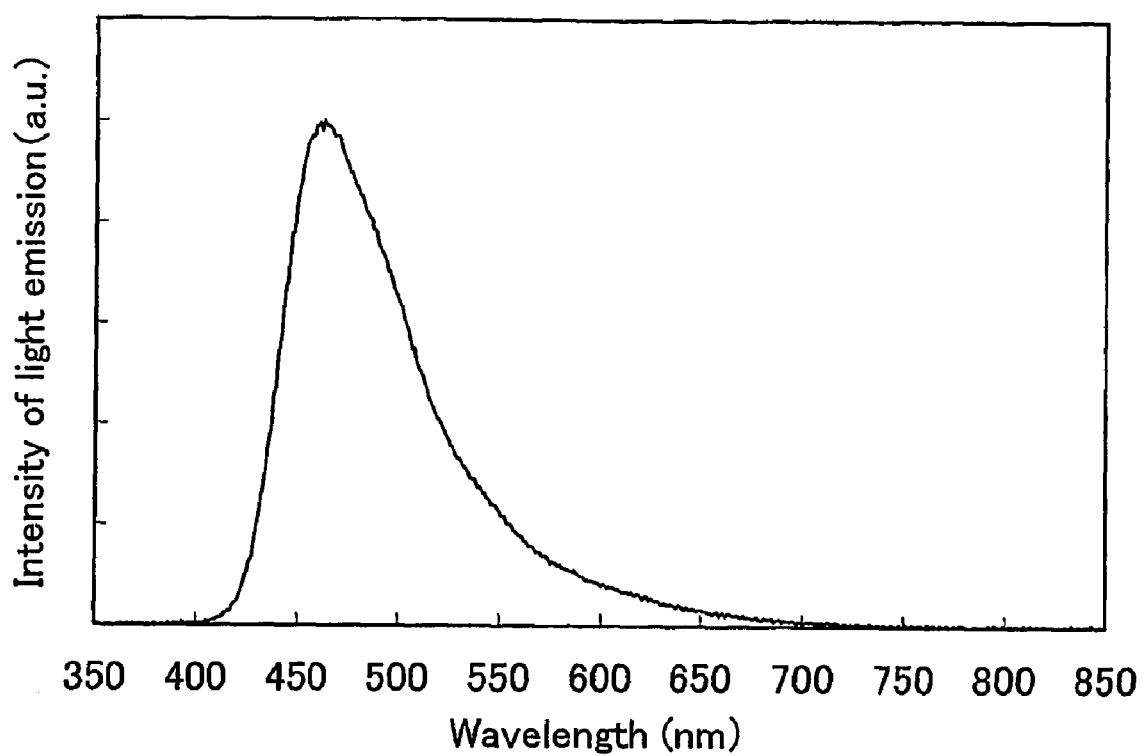
FIG. 31 is a light emission spectrum of a light emitting element manufactured in Embodiment 7.

A light emission spectrum of the light emitting element manufactured in this embodiment is shown in FIG. 31. In FIG. 31, a horizontal axis represents a wavelength (nm) and a vertical axis represents intensity (arbitrary unit). According to FIG. 31, it is found that the light emitting element of this embodiment has a peak of light emission spectrum at 465 nm and exhibits blue light. Moreover, the CIE chromaticity coordinates were x=0.18, y=0.22. Consequently, it was found that the light emitting element of this embodiment exhibits blue light with good color purity.

EMBODIMENT 8

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

Subsequently, the inside of the vacuum evaporation apparatus was evacuated so that the pressure was reduced to 10$^{-4}$ Pa. Then, a first layer 303 including copper phthalocyanine was formed over the first electrode 302 by an evaporation method. A thickness of the first layer 303 was set to be 20 nm. The first layer 303 serves as a hole injecting layer when operating the light emitting element.

Subsequently, a second layer 304 including BSPB was formed over the first layer 303 by an evaporation method. A thickness of the second layer 304 was set to be 40 nm. The second layer 304 serves as a hole transporting layer when operating the light emitting element.

A third layer 305 containing t-BuDNA and YGABPA was formed over the second layer 304 by a co-evaporation method. A thickness of the third layer 305 was set to be 40 nm. The t-BuDNA-YGABPA mass ratio was adjusted to be 1:0.1. Thus, the YGABPA was in such a state of being dispersed in a layer including t-BuDNA. The third layer 305 serves as a light emitting layer when operating the light emitting element. Further, the YGABPA serves as a light emitting substance.

Next, a fourth layer 306 including Alq$_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 32:
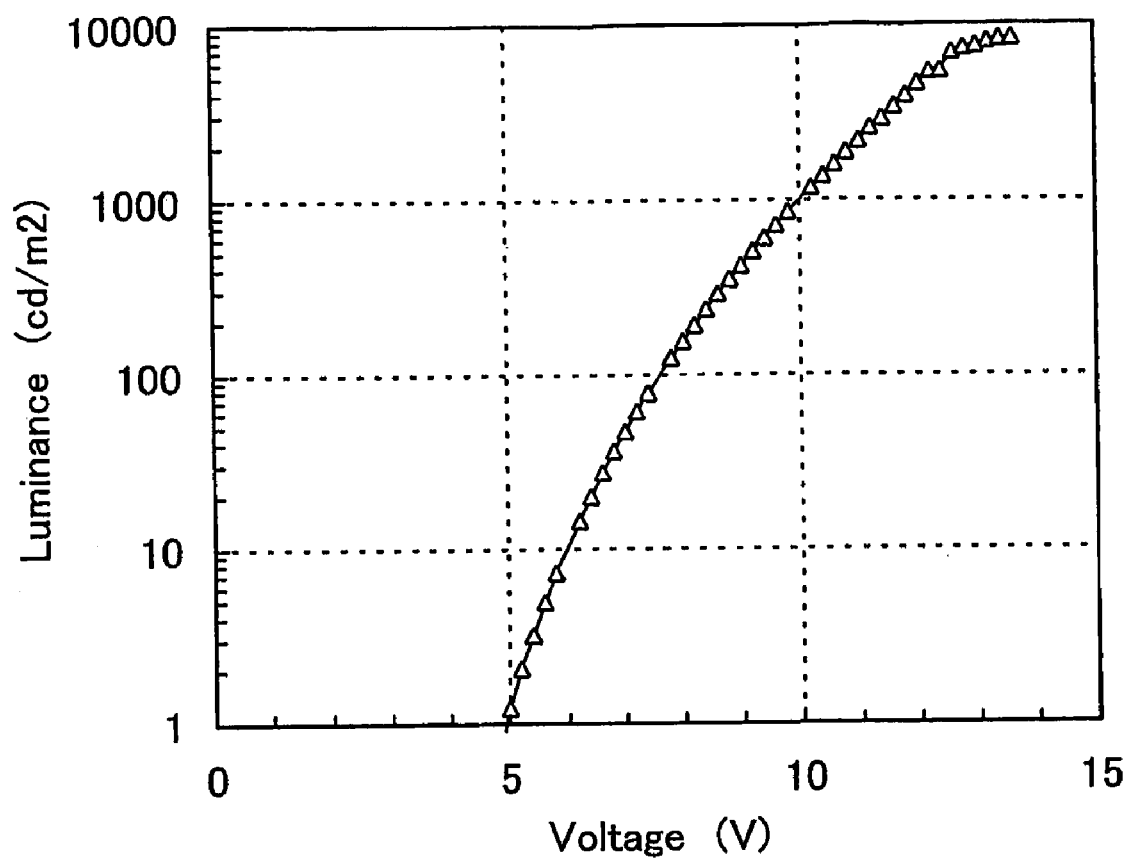
FIG. 32 is a voltage-luminance characteristic of a light emitting element manufactured in Embodiment 8.
Figure 33:
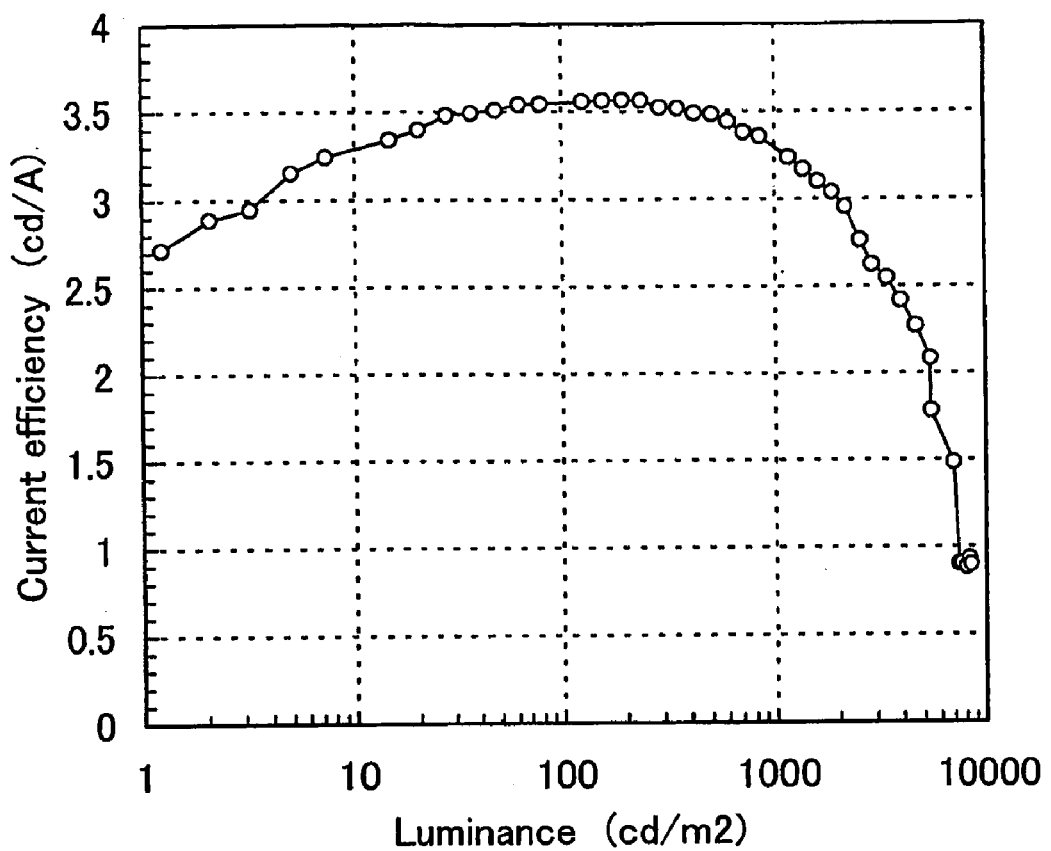
FIG. 33 is a luminance-current efficiency characteristic of a light emitting element manufactured in Embodiment 8.

Measurement results are shown in FIG. 32 and FIG. 33. FIG. 32 shows a measurement result of a voltage-luminance characteristic whereas FIG. 33 shows a measurement result of a luminance-current efficiency characteristic. In FIG. 32, a horizontal axis represents the voltage (V) and a vertical axis represents the luminance (cd/m$^2$). In FIG. 33, a horizontal axis represents the luminance (cd/m$^2$) and a vertical axis represents the current efficiency (cd/A).

Figure 34:
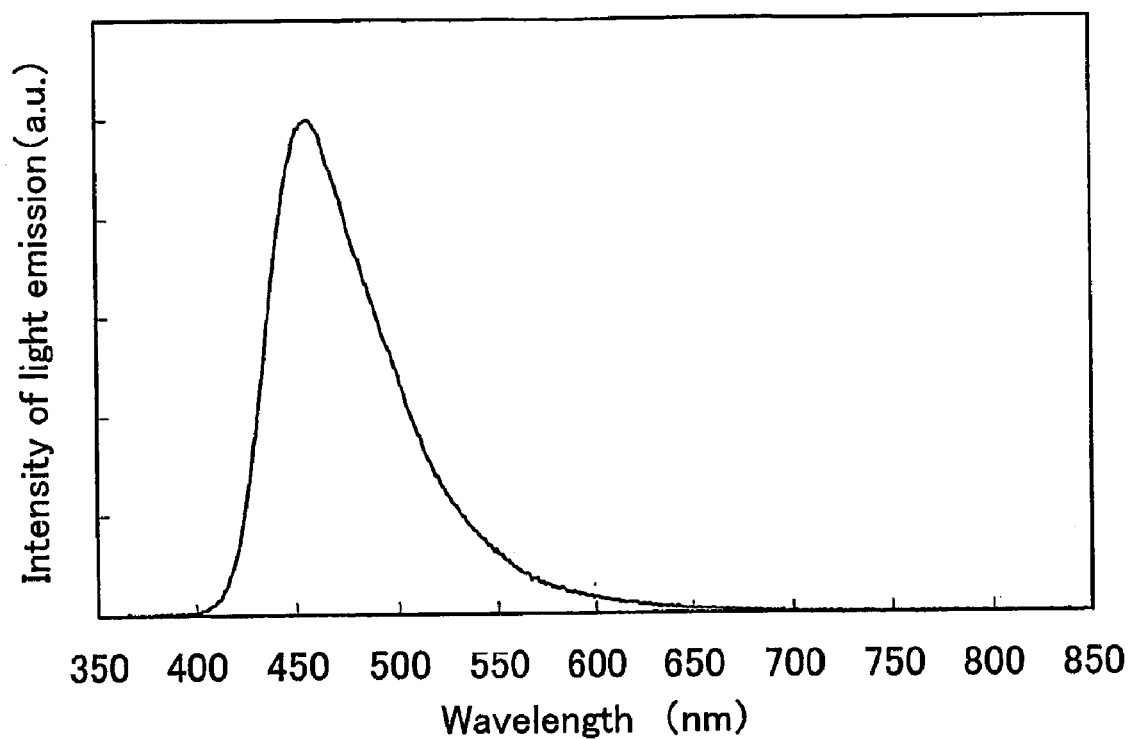
FIG. 34 is a light emission spectrum of a light emitting element manufactured in Embodiment 8.

A light emission spectrum of the light emitting element manufactured in this embodiment is shown in FIG. 34. In FIG. 34, a horizontal axis represents a wavelength (nm) and a vertical axis represents intensity (arbitrary unit). According to FIG. 34, it is found that the light emitting element of this embodiment has a peak of light emission spectrum at 459 nm and exhibits blue light. Moreover, the CIE chromaticity coordinates were x=0.15, y=0.15. Consequently, it was found that the light emitting element of this embodiment exhibits blue light with good color purity.

EMBODIMENT 9

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to 10$^{-4}$ Pa. Then, a first layer 303 including DNTPD was formed over the first electrode 302 by an evaporation method. A thickness of the first layer 303 was set to be 50 nm. The first layer 303 serves as a hole injecting layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing CzPA and YGABPA was formed over the second layer 304 by a co-evaporation method. A thickness of the third layer 305 was set to be 40 nm. The CzPA-YGABPA mass ratio was adjusted to be 1:0.1. Thus, the YGABPA was in such a state of being dispersed in a layer including the CzPA. The third layer 305 serves as a light emitting layer when operating the light emitting element. The YGABPA serves as a light emitting substance. The CzPA is a substance represented by the following structural formula (10).

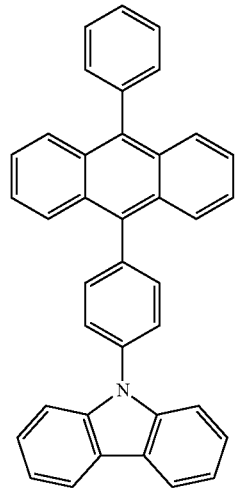

(10)

Next, a fourth layer 306 including Alq$_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 35:
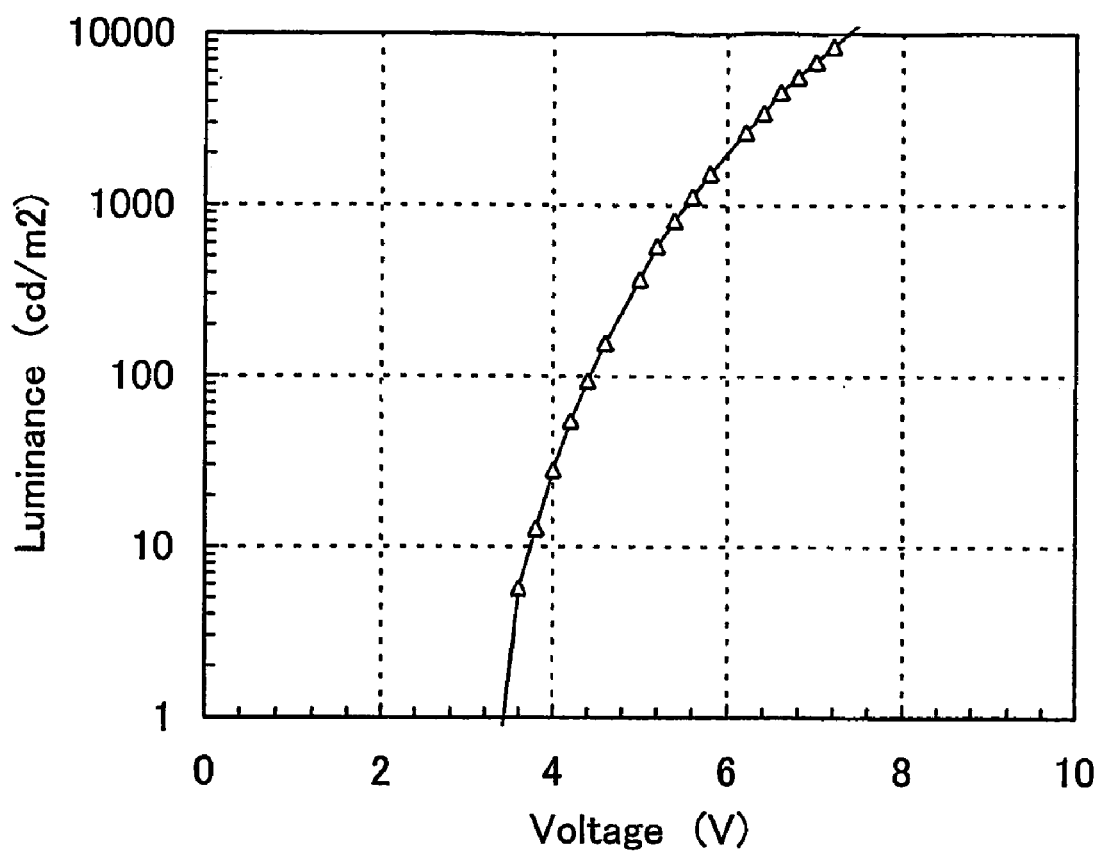
FIG. 35 is a voltage-luminance characteristic of a light emitting element manufactured in Embodiment 9.
Figure 36:
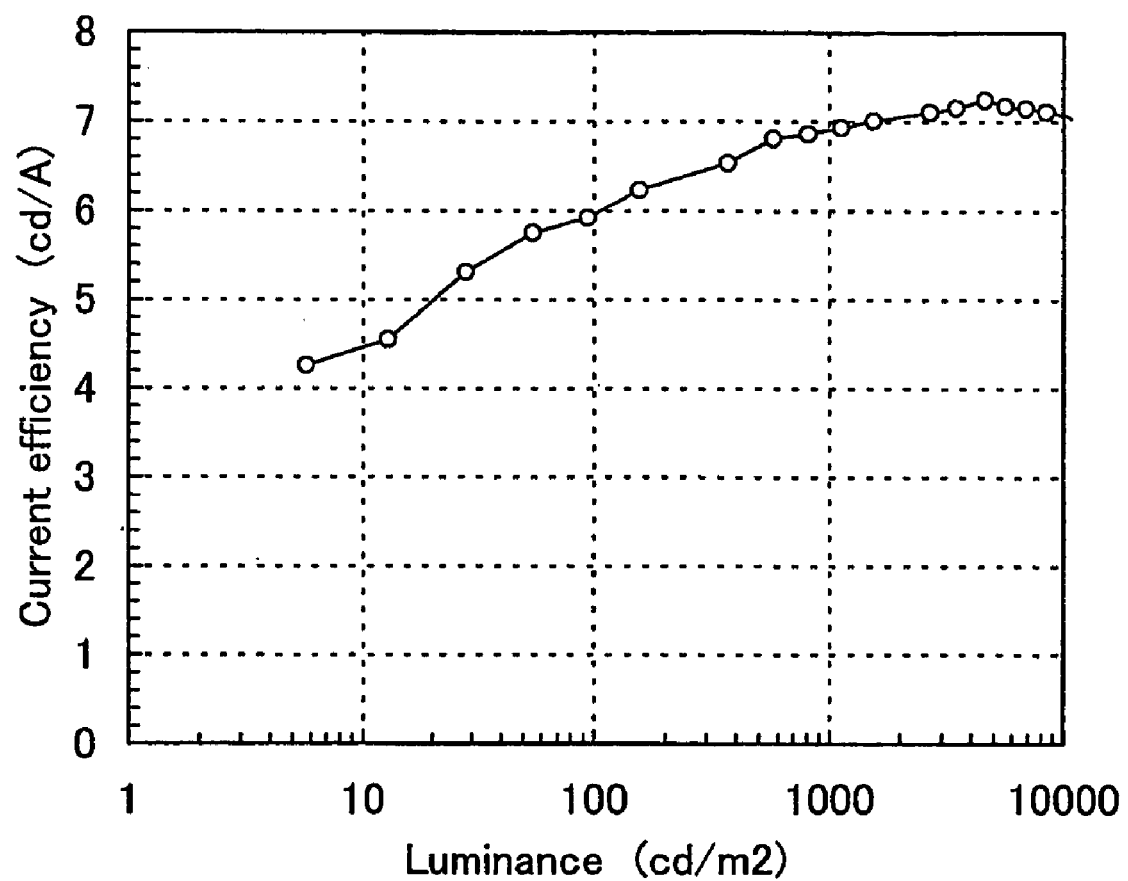
FIG. 36 is a luminance-current efficiency characteristic of a light emitting element manufactured in Embodiment 9.

Measurement results are shown in FIG. 35 and FIG. 36. FIG. 35 shows a measurement result of a voltage-luminance characteristic whereas FIG. 36 shows a measurement result of a luminance-current efficiency characteristic. In FIG. 35, a horizontal axis represents the voltage (V) and a vertical axis represents the luminance (cd/m$^2$). In FIG. 36, a horizontal axis represents the luminance (cd/m$^2$) and a vertical axis represents the current efficiency (cd/A).

Figure 37:
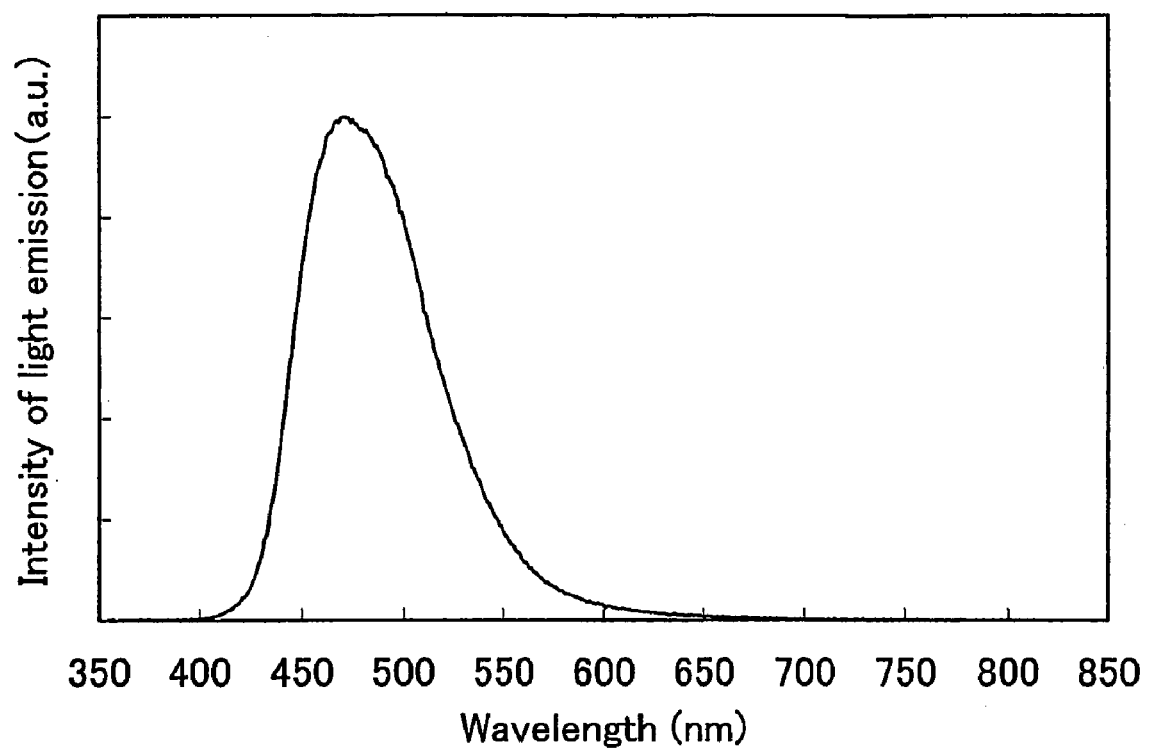
FIG. 37 is a light emission spectrum of a light emitting element manufactured in Embodiment 9.

A light emission spectrum of the light emitting element manufactured in this embodiment is shown in FIG. 37. In FIG. 37, a horizontal axis represents a wavelength (nm) and a vertical axis represents intensity (arbitrary unit). According to FIG. 37, it is found that the light emitting element of this embodiment has a peak of light emission spectrum at 474 nm and exhibits blue light. Moreover, the CIE chromaticity coordinates were x=0.15, y=0.24. Consequently, it was found that the light emitting element of this embodiment exhibits blue light with good color purity.

EMBODIMENT 10

A method for manufacturing a light emitting element that uses the YGABPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 containing NPB and molybdenum oxide was formed over the first electrode 302 by an evaporation method. A thickness of the first layer 303 was set to be 50 nm. The NPB-molybdenum oxide mass ratio was adjusted to be 4:2. It is to be noted that molybdenum trioxide was particularly used as the evaporation material. The first layer 303 serves as a hole generating layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing CzPA and YGABPA was formed over the second layer 304 by a co-evaporation method. A thickness of the third layer 305 was set to be 40 nm. The CzPA-YGABPA mass ratio was adjusted to be 1:0.1. Thus, the YGABPA was in such a state of being dispersed in a layer including the CzPA. The third layer 305 serves as a light emitting layer when operating the light emitting element. The YGABPA serves as a light emitting substance.

Next, a fourth layer 306 including Alq$_3$ was formed over the third layer 305 by an evaporation method. A thickness of the fourth layer 306 was set to be 20 nm. The fourth layer 306 serves as an electron transporting layer when operating the light emitting element.

A fifth layer 307 including calcium fluoride was formed over the fourth layer 306 by an evaporation method. A thickness of the fifth layer 307 was set to be 1 nm. The fifth layer 307 serves as an electron injecting layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGABPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 38:
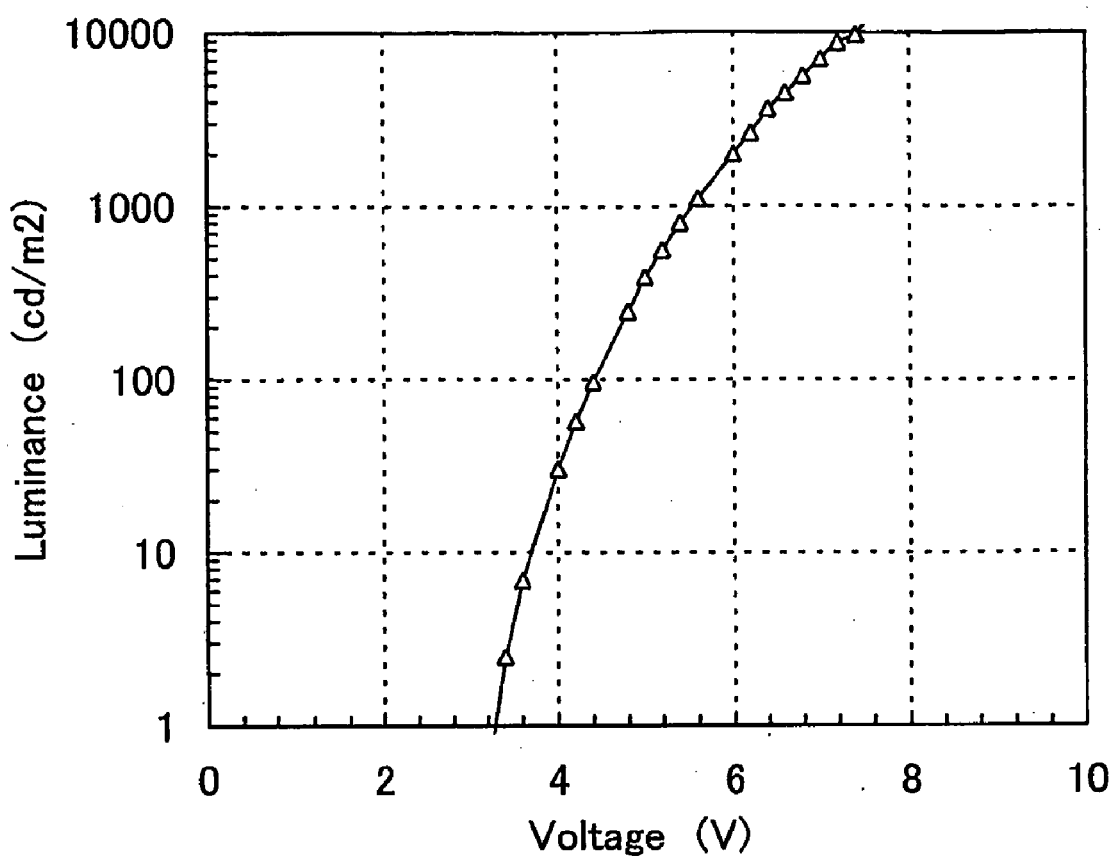
FIG. 38 is a voltage-luminance characteristic of a light emitting element manufactured in Embodiment 10.
Figure 39:
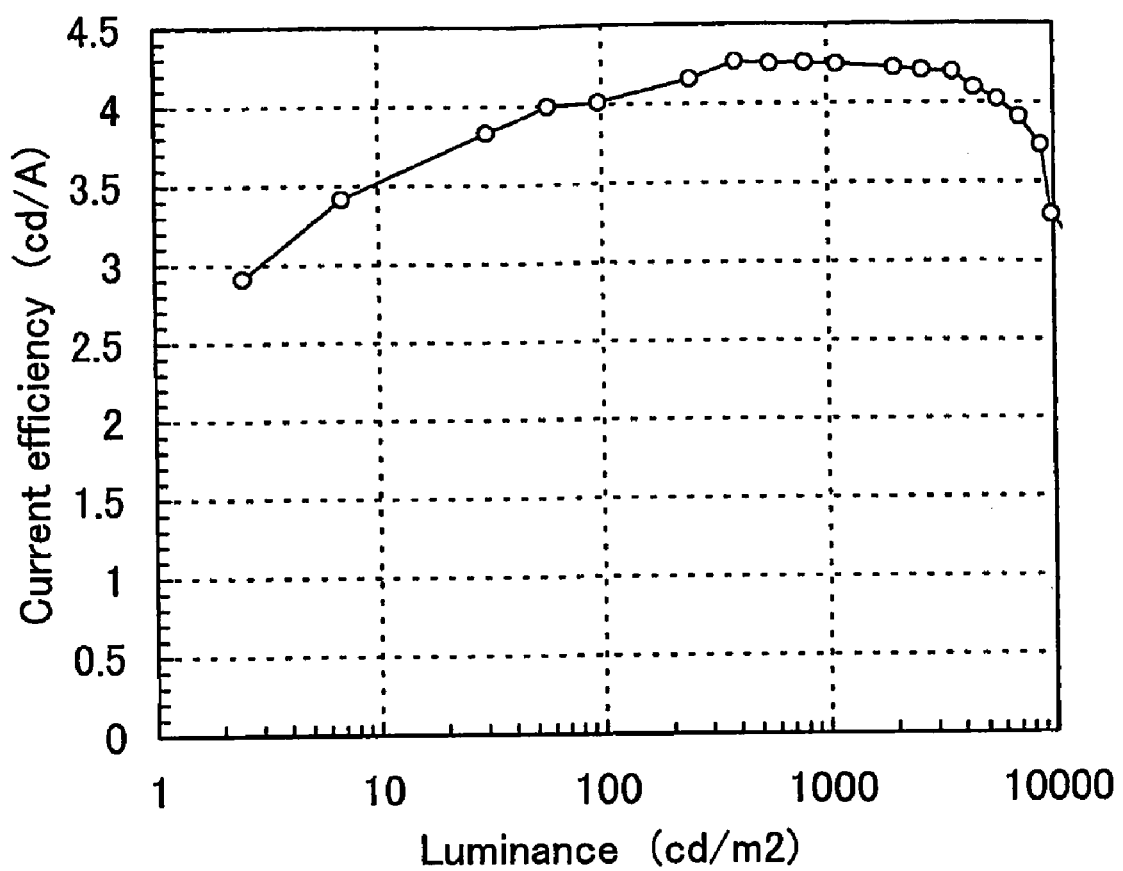
FIG. 39 is a luminance-current efficiency characteristic of a light emitting element manufactured in Embodiment 10.

Measurement results are shown in FIG. 38 and FIG. 39. FIG. 38 shows a measurement result of a voltage-luminance characteristic whereas FIG. 39 shows a measurement result of a luminance-current efficiency characteristic. In FIG. 38, a horizontal axis represents the voltage (V) and a vertical axis represents the luminance (cd/m$^2$). In FIG. 39, a horizontal axis represents the luminance (cd/m$^2$) and a vertical axis represents the current efficiency (cd/A).

Figure 40:
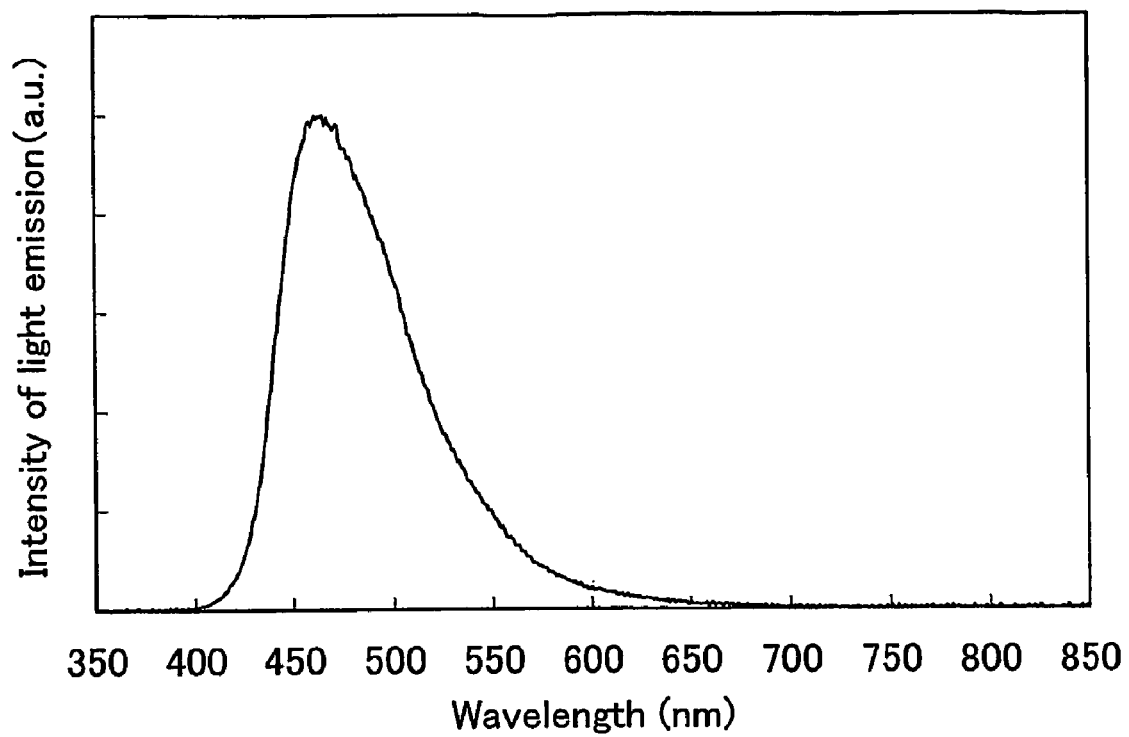
FIG. 40 is a light emission spectrum of a light emitting element manufactured in Embodiment 10.

The light emission spectrum of the light emitting element manufactured in this embodiment is shown in FIG. 40. In FIG. 40, a horizontal axis represents a wavelength (nm) and a vertical axis represents the intensity (arbitrary unit). According to FIG. 40, it is found that the light emitting element of this embodiment has a peak of light emission spectrum at 466 nm, and exhibits blue light. Moreover, the CIE chromaticity coordinates were x=0.16, y=0.21. Consequently, it is found that the light emitting element of this embodiment exhibits blue light with good color purity.

EMBODIMENT 11

A method for manufacturing a light emitting element that uses the YGAPA synthesized in Embodiment 3 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 including DNTPD was formed over the first electrode 302 by an evaporation method. A thickness of the first layer 303 was set to be 50 nm. The first layer 303 serves as a hole injecting layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing CzPA and YGAPA was formed over the second layer 304 by a co-evaporation method. A thickness of the third layer 305 was set to be 40 nm. The CzPA-YGAPA mass ratio was adjusted to be 1:0.04. Thus, the YGAPA was in such a state of being dispersed in a layer including CzPA. The third layer 305 serves as a light emitting layer when operating the light emitting element. Further, the YGAPA serves as a light emitting substance.

Next, a fourth layer 306 including $Alq_3$ was formed over the third layer 305 by an evaporation method. A thickness of the fourth layer 306 was set to be 10 nm. The fourth layer 306 serves as an electron transporting layer when operating the light emitting element.

Next, a fifth layer 307 containing $Alq_3$ and lithium (Li) was formed over the fourth layer 306 by a co-evaporation method. A thickness of the fifth layer 307 was set to be 10 nm. The $Alq_3$-Li mass ratio was adjusted to be 1:0.01. The fifth layer 307 serves as an electron generating layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGAPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 41:
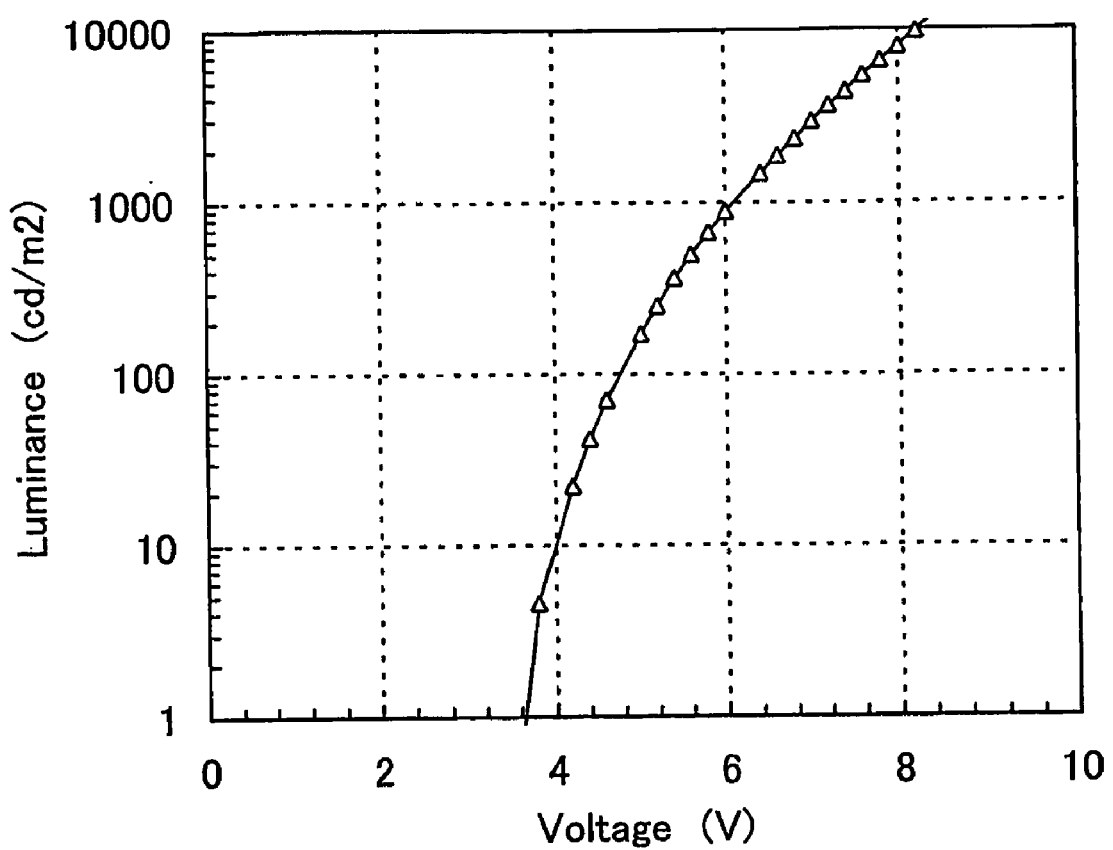
FIG. 41 is a voltage-luminance characteristic of a light emitting element manufactured in Embodiment 11.
Figure 42:
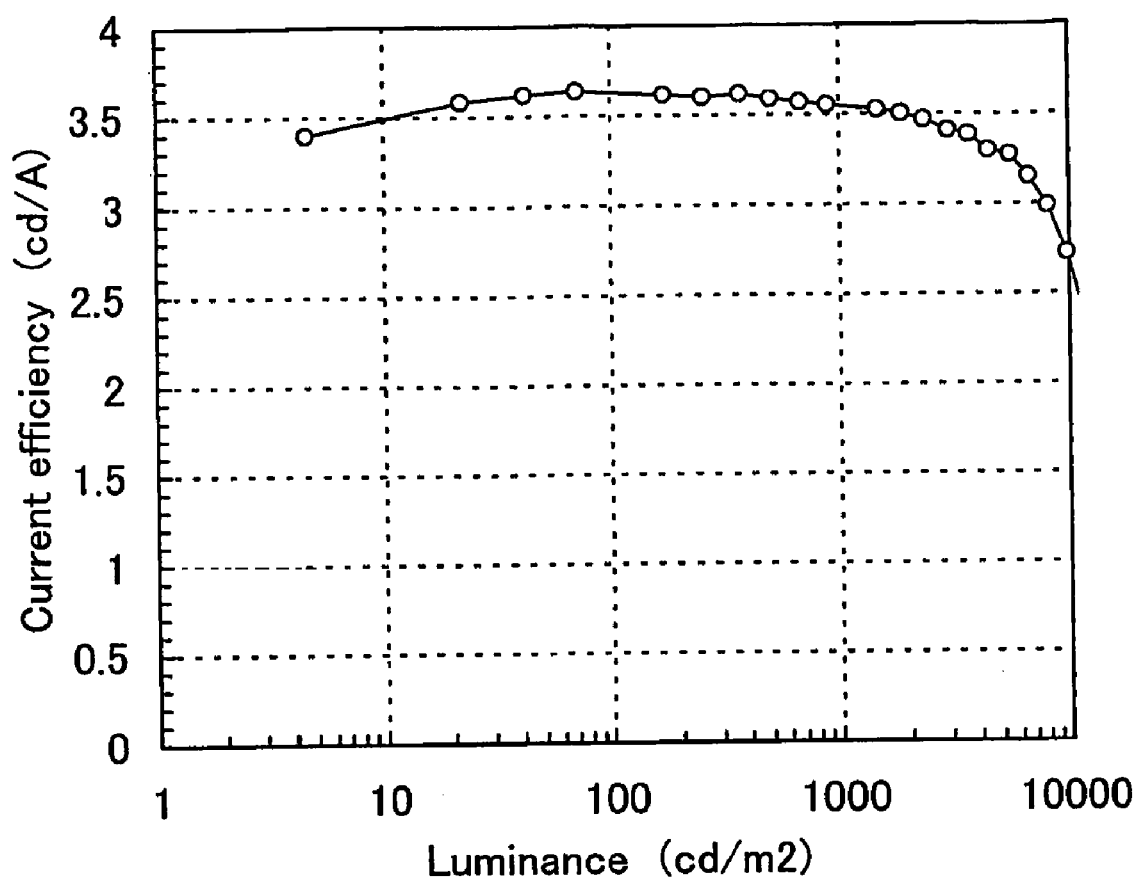
FIG. 42 is a luminance-current efficiency characteristic of a light emitting element manufactured in Embodiment 11.

Measurement results are shown in FIG. 41 and FIG. 42. FIG. 41 shows a measurement result of a voltage-luminance characteristic whereas FIG. 42 shows a measurement result of a luminance-current efficiency characteristic. In FIG. 41, a horizontal axis represents the voltage (V) and a vertical axis represents the luminance ($cd/m^2$). In FIG. 42, a horizontal axis represents the luminance ($cd/m^2$) and a vertical axis represents the current efficiency (cd/A).

Figure 43:
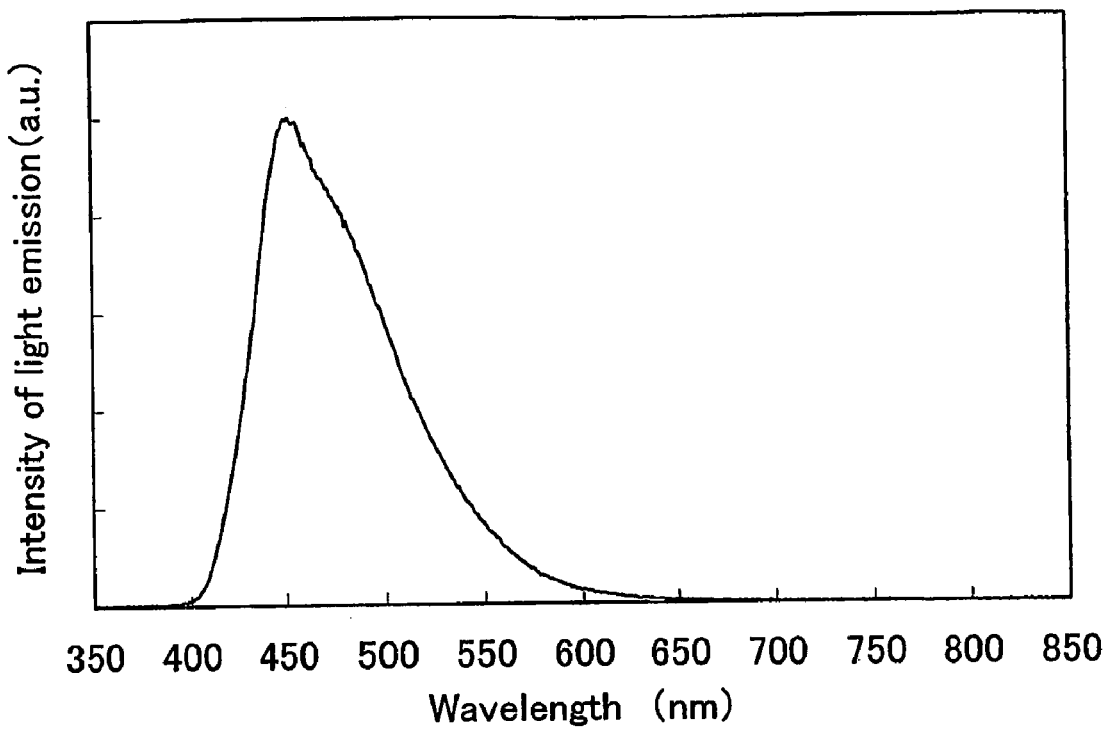
FIG. 43 is a light emission spectrum of a light emitting element manufactured in Embodiment 11.

A light emission spectrum of the light emitting element manufactured in this embodiment is shown in FIG. 43. In FIG. 43, a horizontal axis represents a wavelength (nm) and a vertical axis represents intensity (arbitrary unit). According to FIG. 43, it is found that the light emitting element of this embodiment has a peak of light emission spectrum at 456 nm and exhibits blue light. Moreover, the CIE chromaticity coordinates were x=0.16, y=0.17. Consequently, it was found that the light emitting element of this embodiment exhibits blue light with good color purity.

EMBODIMENT 12

A method for manufacturing a light emitting element that uses the YGAPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 containing NPB and molybdenum oxide was formed over the first electrode 302 by an evaporation method. A thickness of the first layer 303 was set to be 50 nm. The NPB-molybdenum oxide mass ratio was adjusted to be 4:2. It is to be noted that molybdenum trioxide was particularly used as the evaporation material. The first layer 303 serves as a hole generating layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing CzPA and YGAPA was formed over the second layer 304 by a co-evaporation method. A thickness of the third layer 305 was set to be 40 nm. The CzPA-YGAPA mass ratio was adjusted to be 1:0.04. Thus, the YGAPA was in such a state of being dispersed in a layer including CzPA. The third layer 305 serves as a light emitting layer when operating the light emitting element. Further, the YGAPA serves as a light emitting substance.

Next, a fourth layer 306 including $Alq_3$ was formed over the third layer 305 by an evaporation method. A thickness of the fourth layer 306 was set to be 10 nm. The fourth layer 306 serves as an electron transporting layer when operating the light emitting element.

Next, a fifth layer 307 containing $Alq_3$ and lithium (Li) was formed over the fourth layer 306 by a co-evaporation method. A thickness of the fifth layer 307 was set to be 10 nm. The $Alq_3$-Li mass ratio was adjusted to be 1:0.01. The fifth layer 307 serves as an electron generating layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGAPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 44:
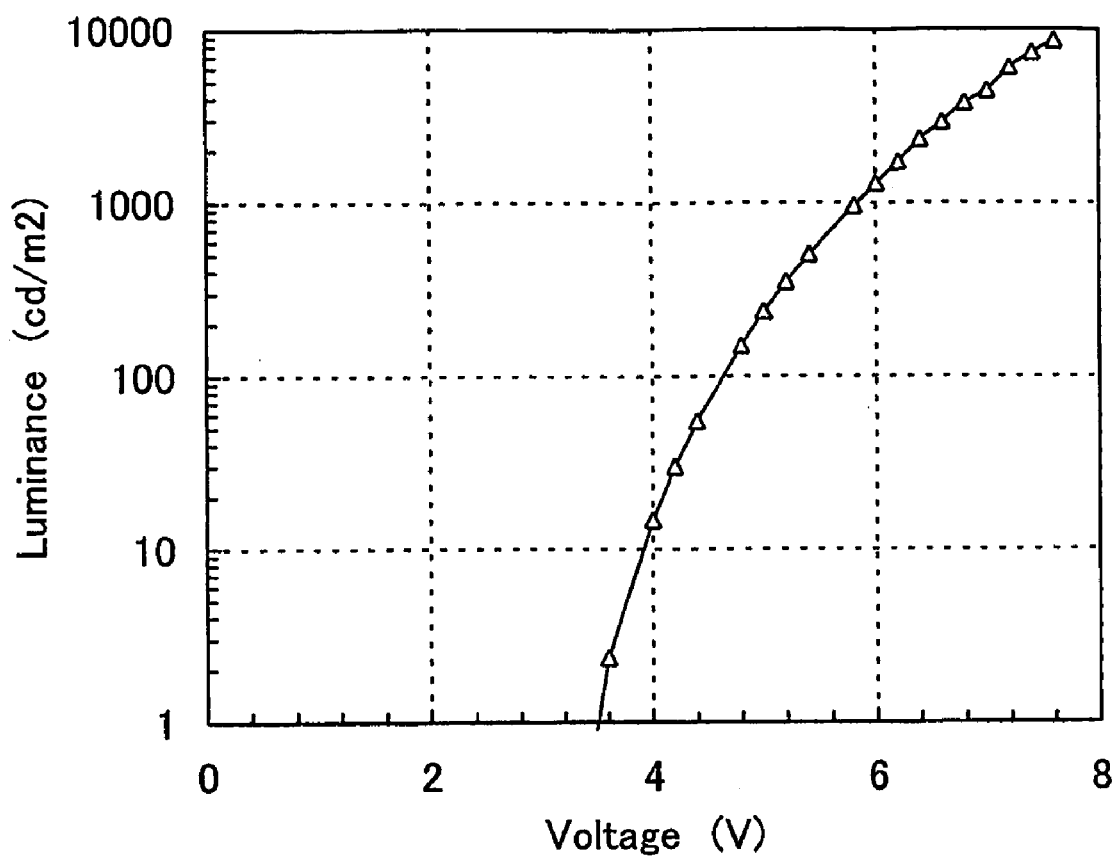
FIG. 44 is a voltage-luminance characteristic of a light emitting element manufactured in Embodiment 12.
Figure 45:
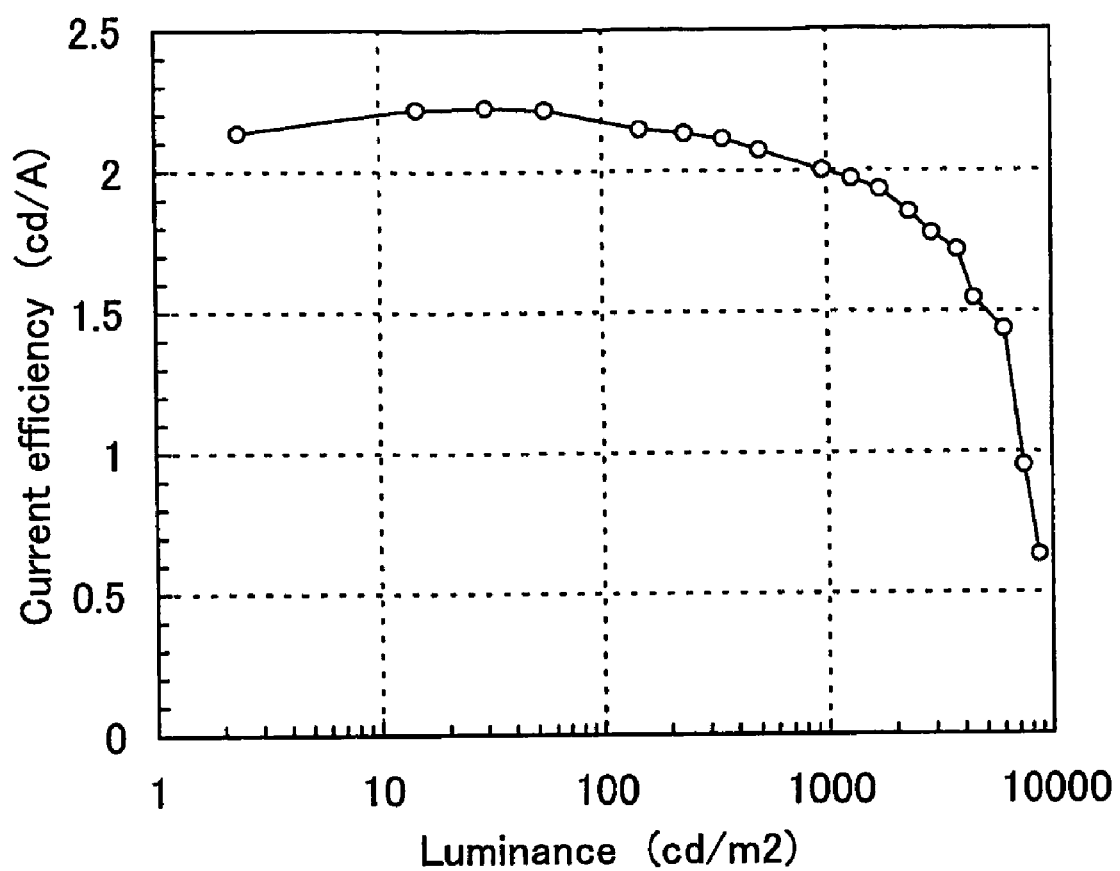
FIG. 45 is a luminance-current efficiency characteristic of a light emitting element manufactured in Embodiment 12.

Measurement results are shown in FIG. 44 and FIG. 45. FIG. 44 shows a measurement result of a voltage-luminance characteristic whereas FIG. 45 shows a measurement result of a luminance-current efficiency characteristic. In FIG. 44, a horizontal axis represents the voltage (V) and a vertical axis represents the luminance ($cd/m^2$). In FIG. 45, a horizontal axis represents the luminance ($cd/m^2$) and a vertical axis represents the current efficiency (cd/A).

Figure 46:
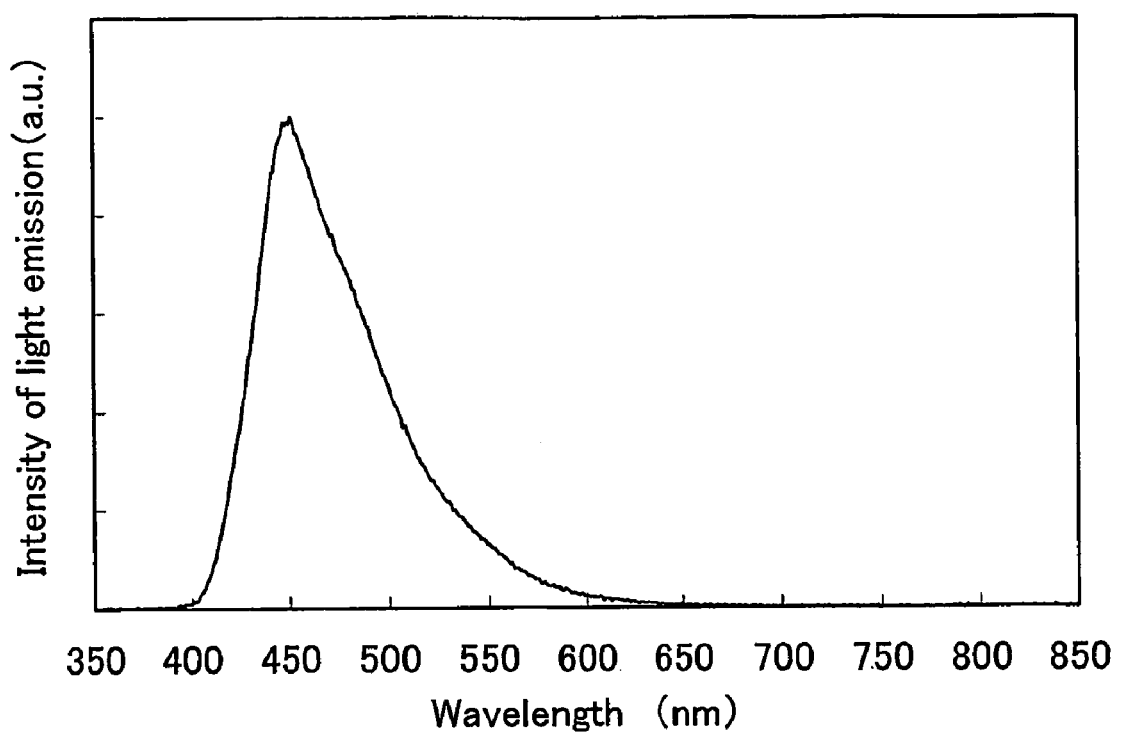
FIG. 46 is a light emission spectrum of a light emitting element manufactured in Embodiment 12.

A light emission spectrum of the light emitting element manufactured in this embodiment is shown in FIG. 46. In FIG. 46, a horizontal axis represents a wavelength (nm) and a vertical axis represents intensity (arbitrary unit). According to FIG. 46, it is found that the light emitting element of this embodiment has a peak of light emission spectrum at 452 nm and exhibits blue light. Moreover, the CIE chromaticity coordinates were x=0.16, y=0.14. Consequently, it was found that the light emitting element of this embodiment exhibits blue light with good color purity.

EMBODIMENT 13

A method for manufacturing a light emitting element that uses the YGAPA synthesized in Embodiment 2 as a light emitting substance and an operational characteristic of the light emitting element will be described in this embodiment. Further, a light emitting element of this embodiment is the same as the light emitting element of Embodiment 4 in point of having a structure in which five layers each having different substances and layer thicknesses are stacked between a first electrode and a second electrode. Therefore, this embodiment will be described with reference to FIG. 19 also used in the description of Embodiment 4.

As shown in FIG. 19, indium tin oxide containing silicon oxide was formed over a glass substrate 301 by a sputtering method to form a first electrode 302. A thickness of the first electrode 302 was set to be 110 nm. Further, the first electrode was formed to have a square shape with a size of 2 mm×2 mm.

Next, the glass substrate 301 over which the first electrode 302 was formed was fixed to a holder provided in a vacuum evaporation apparatus, so that a surface over which the first electrode 302 was formed is a lower side.

The inside of the vacuum evaporation apparatus was evacuated so that the pressure was reduced to $10^{-4}$ Pa. Then, a first layer 303 containing DNTPD and molybdenum oxide was formed over the first electrode 302 by a co-evaporation method. A thickness of the first layer 303 was set to be 50 nm. The DNTPS-molybdenum oxide mass ratio was adjusted to be 4:2. It is to be noted that molybdenum trioxide was particularly used as an evaporation material. The first layer 303 serves as a hole generating layer when operating the light emitting element.

Subsequently, a second layer 304 including NPB was formed over the first layer 303 by an evaporation method. A thickness of the second layer 304 was set to be 10 nm. The second layer 304 serves as a hole transporting layer when operating the light emitting element.

A third layer 305 containing CzPA and YGAPA was formed over the second layer 304 by a co-evaporation method. A thickness of the third layer 305 was set to be 40 nm. The CzPA-YGAPA mass ratio was adjusted to be 1:0.04. Thus, the YGAPA was in such a state of being dispersed in a layer including CzPA. The third layer 305 serves as a light emitting layer when operating the light emitting element. Further, the YGAPA serves as a light emitting substance.

Next, a fourth layer 306 including $Alq_3$ was formed over the third layer 305 by an evaporation method. A thickness of the fourth layer 306 was set to be 10 nm. The fourth layer 306 serves as an electron transporting layer when operating the light emitting element.

Next, a fifth layer 307 containing $Alq_3$ and lithium (Li) was formed over the fourth layer 306 by a co-evaporation method. A thickness of the fifth layer 307 was set to be 10 nm. The $Alq_3$-Li mass ratio was adjusted to be 1:0.01. The fifth layer 307 serves as an electron generating layer when operating the light emitting element.

Next, a second electrode 308 including aluminum was formed over the fifth layer 307. A thickness of the second electrode 308 was set to be 200 nm.

When voltage is applied to the light emitting element manufactured as above such that an electric potential of the first electrode 302 is higher than that of the second electrode 308, current flows through the light emitting element. Electrons and holes are recombined in the third layer 305 serving as a light emitting layer to generate excitation energy. The excited YGAPA emits light when returning to a ground state.

This light emitting element was sealed in a glove box under a nitrogen atmosphere without being exposed to atmospheric air. Subsequently, an operational characteristic of the light emitting element was measured. The measurement was carried out at room temperature (under an atmosphere maintaining 25° C.).

Figure 47:
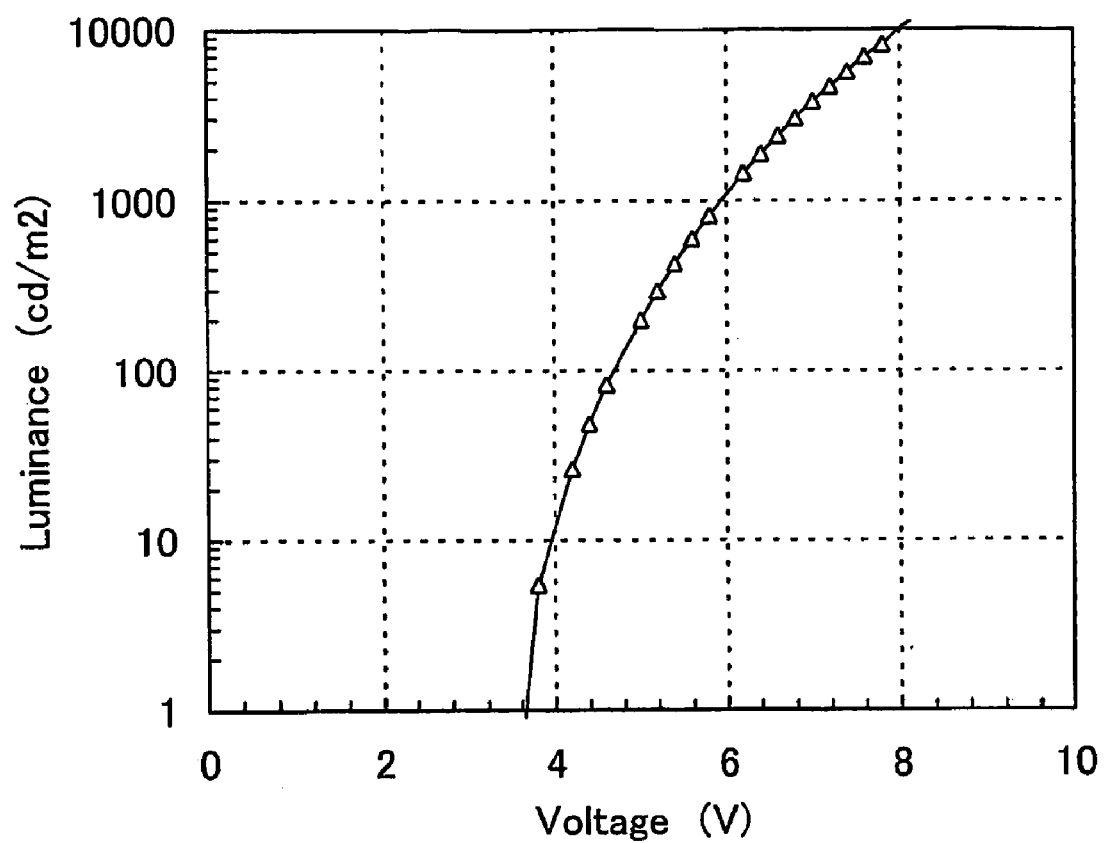
FIG. 47 is a voltage-luminance characteristic of a light emitting element manufactured in Embodiment 13.
Figure 48:
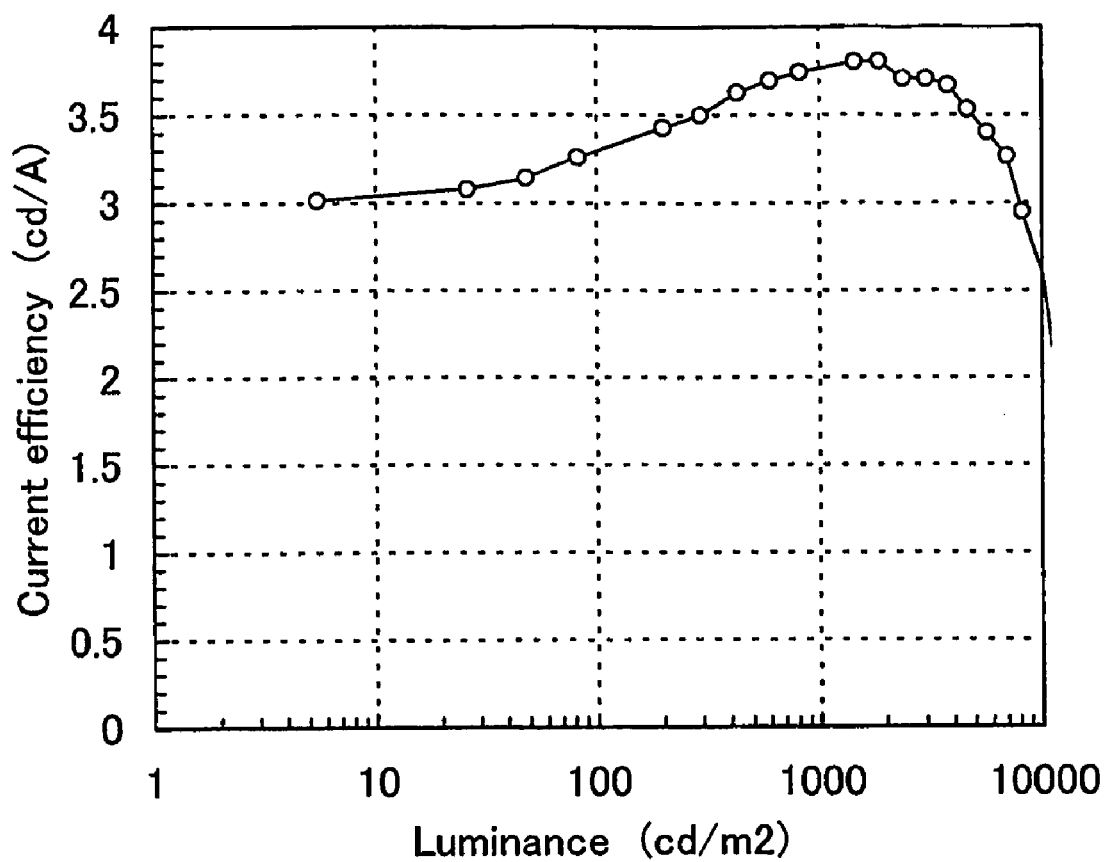
FIG. 48 is a luminance-current efficiency characteristic of a light emitting element manufactured in Embodiment 13.

Measurement results are shown in FIG. 47 and FIG. 48. FIG. 47 shows a measurement result of a voltage-luminance characteristic whereas FIG. 48 shows a measurement result of a luminance-current efficiency characteristic. In FIG. 47, a horizontal axis represents the voltage (V) and a vertical axis represents the luminance ($cd/m^2$). In FIG. 48, a horizontal axis represents the luminance ($cd/m^2$) and a vertical axis represents the current efficiency (cd/A).

Figure 49:
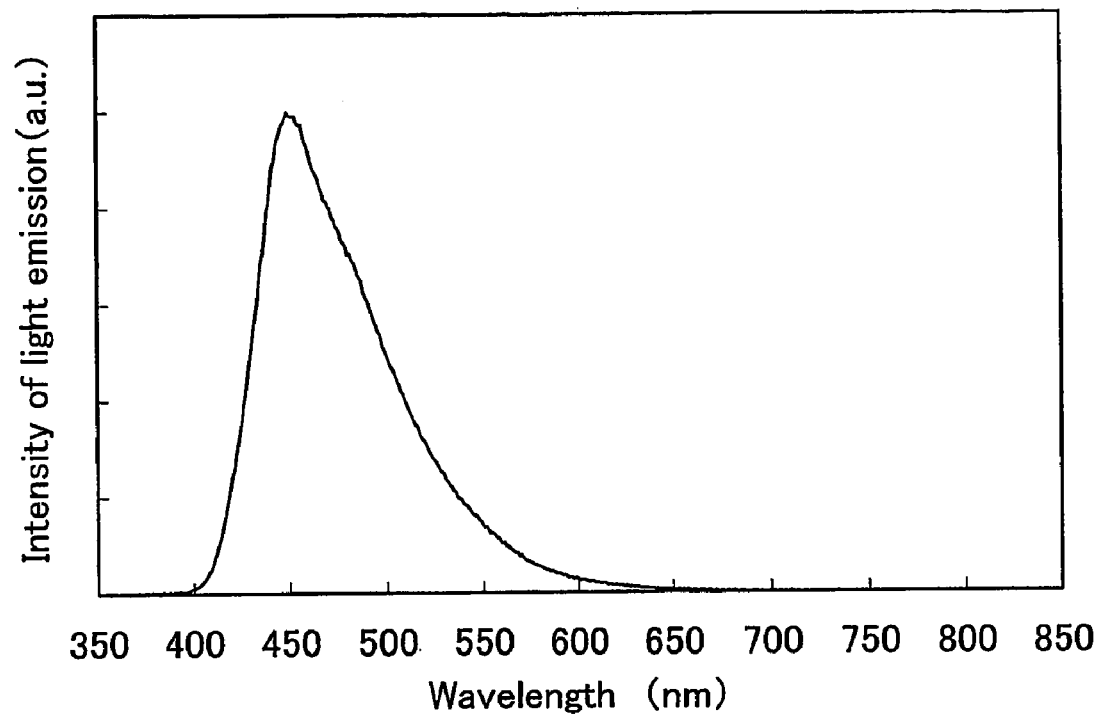
FIG. 49 is a light emission spectrum of a light emitting element manufactured in Embodiment 13.

A light emission spectrum of the light emitting element manufactured in this embodiment is shown in FIG. 49. In FIG. 49, a horizontal axis represents a wavelength (nm) and a vertical axis represents intensity (arbitrary unit). According to FIG. 49, it is found that the light emitting element of this embodiment has a peak of light emission spectrum at 453 nm and exhibits blue light. Moreover, the CIE chromaticity coordinates were x=0.16, y=0.16. Consequently, it was found that the light emitting element of this embodiment exhibits blue light with good color purity.

What is claimed is:
1. A light emitting element material represented by Structural Formula:

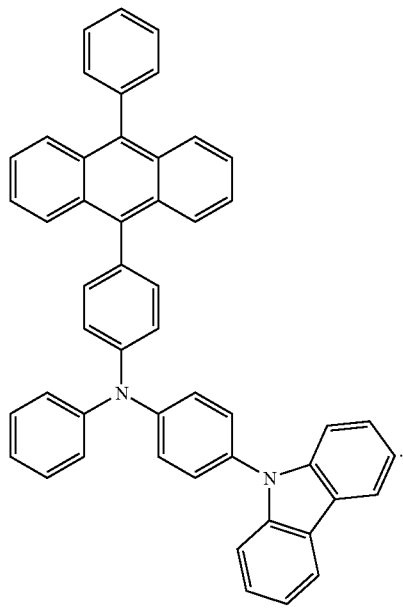

2. A light emitting element comprising:
a light emitting layer including a light emitting substance between electrodes,
wherein the light emitting substance is represented by the following Structural Formula:

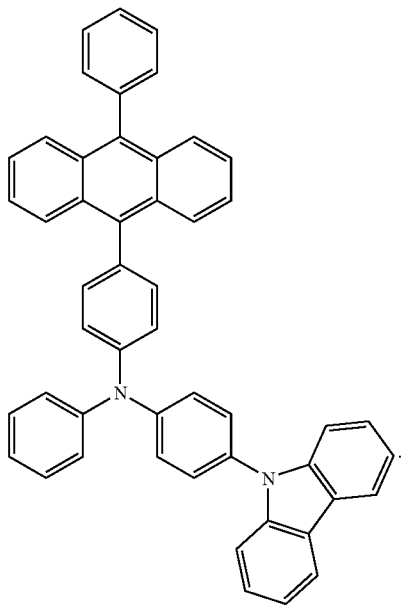

3. The light emitting element according to claim 2,
wherein the light emitting layer includes a host between the electrodes, and
wherein the host is a substance having a higher electron transporting property than a hole transporting property.

4. The light emitting element according to claim 2,
wherein the light emitting layer includes a host between the electrodes, and
wherein the host is one of 2-tent-butyl-9,10-di(2-naphthyl) anthracene, 9-[4-(N-carbazolyl)]phenyl-10-phenylanthracene, and diphenyl anthracene.

5. A light emitting device including the light emitting element according to claim 2.

6. An electronic appliance including the light emitting device according to claim 5 in a display portion or a lighting portion.

7. A light emitting element material represented by the following General Formula:

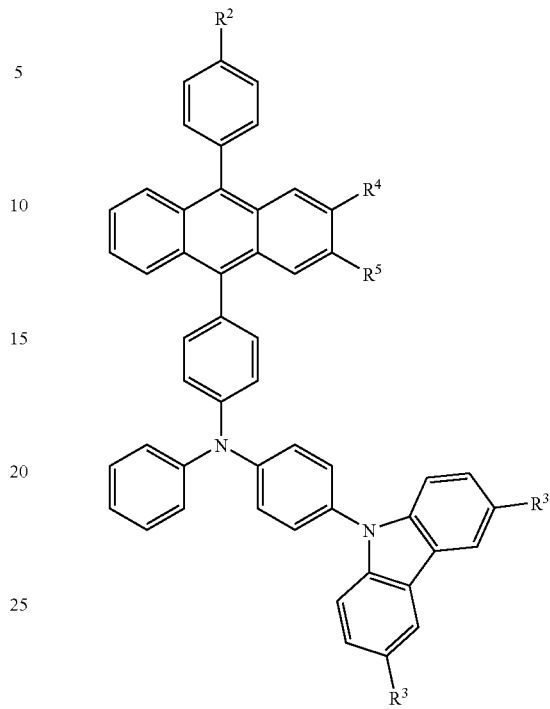

wherein $R^2$ represents hydrogen,
wherein $R^4$ and $R^5$ represent any of hydrogen, methyl, or tent-butyl, and at least one of $R^4$ and $R^5$ represents hydrogen, and
wherein $R^3$ represents any one selected from hydrogen, an alkyl group having 1 to 4 carbon atoms, and an aryl group having 1 to 12 carbon atoms.

8. A light emitting element comprising:
a light emitting layer including the light emitting element material according to claim 7, and a host between electrodes,
wherein the host is a substance having a higher ionization potential and a larger energy gap than those of the light emitting element material.

9. The light emitting element according to claim 8, wherein the host is a substance having a higher electron transporting property than a hole transporting property.

10. The light emitting element according to claim 8, wherein the host is one of 2-tert-butyl-9,10-di(2-naphthyl) anthracene, 9-[4-(N-carbazolyl)]phenyl-10-phenylanthracene, and diphenyl anthracene.

11. A light emitting device including the light emitting element according to claim 8.

12. An electronic appliance including the light emitting device according to claim 11 in a display portion or a lighting portion.

* * * * *

UNITED STATES PATENT AND TRADEMARK OFFICE
CERTIFICATE OF CORRECTION

PATENT NO. : 7,838,128 B2  
APPLICATION NO. : 11/574117  
DATED : November 23, 2010  
INVENTOR(S) : Sachiko Kawakami et al.

Page 1 of 1

It is certified that error appears in the above-identified patent and that said Letters Patent is hereby corrected as shown below:

Column 8, line 38, replace "BU" with --Bu--;

Column 50, line 67, replace";" with --,--;

Column 57, line 48, in claim 4 replace "tent" with --tert--;

Column 58, line 33, in claim 7 replace "tent" with --tert--.

Signed and Sealed this
First Day of March, 2011

David J. Kappos
*Director of the United States Patent and Trademark Office*